US012570631B2

(12) United States Patent
Ma et al.

(10) Patent No.: US 12,570,631 B2
(45) Date of Patent: Mar. 10, 2026

(54) SUBSTITUTED N-(4-(PYRIMIDIN AND PYRIDIN-4-YL)BENZYLCARBOXAMIDES AND ITS USE FOR TREATING DISORDERS RESPONSIVE TO INHIBITION OF Btk

(71) Applicant: BIOGEN MA INC., Cambridge, MA (US)

(72) Inventors: Bin Ma, Cambridge, MA (US); Brian T. Hopkins, Newton, MA (US); Isaac Marx, Arlington, MA (US); Jürgen Schulz, Boston, MA (US); George Vandeveer, Stoneham, MA (US); Robin Prince, Sharon, MA (US); Marta Nevalainen, Holliston, MA (US); TeYu Chen, Charlestown, MA (US); Zain Yousaf, Boston, MA (US); Andrew George Capacci, Cambridge, MA (US)

(73) Assignee: BIOGEN MA INC., Cambridge, MA (US)

( * ) Notice: Subject to any disclaimer, the term of this patent is extended or adjusted under 35 U.S.C. 154(b) by 917 days.

(21) Appl. No.: 17/788,127

(22) PCT Filed: Dec. 23, 2020

(86) PCT No.: PCT/US2020/066808

§ 371 (c)(1),
(2) Date: Jun. 22, 2022

(87) PCT Pub. No.: WO2021/133894

PCT Pub. Date: Jul. 1, 2021

(65) Prior Publication Data

US 2023/0121818 A1 Apr. 20, 2023

Related U.S. Application Data

(60) Provisional application No. 63/047,616, filed on Jul. 2, 2020, provisional application No. 62/952,587, filed on Dec. 23, 2019.

(51) Int. Cl.

| | |
|---|---|
| ***C07D 401/14*** | (2006.01) |
| ***C07D 401/12*** | (2006.01) |
| ***C07D 403/10*** | (2006.01) |
| ***C07D 403/12*** | (2006.01) |
| ***C07D 413/12*** | (2006.01) |
| ***C07D 413/14*** | (2006.01) |
| ***C07D 471/04*** | (2006.01) |
| ***C07D 495/04*** | (2006.01) |

(52) U.S. Cl.
CPC ......... *C07D 401/14* (2013.01); *C07D 401/12* (2013.01); *C07D 403/10* (2013.01); *C07D 403/12* (2013.01); *C07D 413/12* (2013.01); *C07D 413/14* (2013.01); *C07D 471/04* (2013.01); *C07D 495/04* (2013.01)

(58) Field of Classification Search
None
See application file for complete search history.

(56) References Cited

FOREIGN PATENT DOCUMENTS

| | | | |
|---|---|---|---|
| WO | 2015/079417 | A1 | 6/2015 |
| WO | 2019/222101 | A1 | 11/2019 |

OTHER PUBLICATIONS

Liang et al. "The development of Bruton's tyrosine kinase (BTK) inhibitors from 2012 to 2017: A mini-review" European Journal of Medicinal Chemistry, 2018, 151, 315-326. (Year: 2018).*

International Search Report and Written Opinion for Application No. PCT/US2020/066808, dated Feb. 19, 2021, 10 pages.

* cited by examiner

*Primary Examiner* — Jennifer A Berrios
*Assistant Examiner* — Sophia Reilly
(74) *Attorney, Agent, or Firm* — McCarter & English, LLP; Xin Zhang

(57) ABSTRACT

Provided are compounds of Formula (I') or pharmaceutically acceptable salts thereof, wherein $R^1$, $R^2$, $R^3$, $R^4$, $R^5$, $R^8$, $R^9$, $R^{11A}$, $R^{11B}$, $R^{12}$, $R^i$, $R^{ii}$, $A^1$, $A^2$, $Q^1$, $Q^2$, $Q^3$, X, W, and n are as defined herein; pharmaceutical compositions comprising said compounds or pharmaceutically acceptable salts thereof, and pharmaceutically acceptable excipients; and methods of treating a disorder responsive to inhibition of Bruton's tyrosine kinase using said compounds, or pharmaceutically acceptable salts thereof, or said pharmaceutical compositions.

(I')

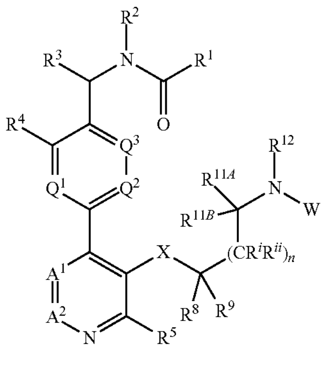

22 Claims, No Drawings

SUBSTITUTED N-(4-(PYRIMIDIN AND PYRIDIN-4-YL)BENZYLCARBOXAMIDES AND ITS USE FOR TREATING DISORDERS RESPONSIVE TO INHIBITION OF Btk

CROSS REFERENCE TO RELATED APPLICATIONS

This application is a 35 U.S.C. § 371 national stage filing of International Application No. PCT/US2020/066808, filed on Dec. 23, 2020, which in turn claims the benefit of the filing date, under 35 U.S.C. § 119 (e), of U.S. Provisional Application No. 62/952,587, filed on Dec. 23, 2019 and U.S. Provisional Application No. 63/047,616, filed on Jul. 2, 2020. The entire contents of each of these applications are incorporated heren by reference.

TECHNICAL FIELD

Provided are certain agents that inhibit Bruton's tyrosine kinase (Btk), and methods of making and using such agents.

BACKGROUND

Protein kinases are a large multigene family consisting of more than 500 proteins which play a critical role in the development and treatment of a number of human diseases in oncology, neurology and immunology. The Tec kinases are non-receptor tyrosine kinases which consists of five members (Tec (tyrosine kinase expressed in hepatocellular carcinoma), Btk (Bruton's tyrosine kinase), Itk (interleukin-2 (IL-2)-inducible T-cell kinase; also known as Emt or Tsk), Rlk (resting lymphocyte kinase; also known as Txk) and Bmx (bone-marrow tyrosine kinase gene on chromosome X; also known as Etk)) and are primarily expressed in haematopoietic cells, although expression of Bmx and Tec has been detected in endothelial and liver cells. Tec kinases (Itk, Rlk and Tec) are expressed in T cell and are all activated downstream of the T-cell receptor (TCR). Btk is a downstream mediator of B cell receptor (BCR) signaling which is involved in regulating B cell activation, proliferation, and differentiation. More specifically, Btk contains a PH domain that binds phosphatidylinositol (3,4,5)-trisphosphate (PIP3). PIP3 binding induces Btk to phosphorylate phospholipase C (PLCy), which in turn hydrolyzes PIP2 to produce two secondary messengers, inositol triphosphate (IP3) and diacylglycerol (DAG), which activate protein kinase PKC, which then induces additional B-cell signaling. Mutations that disable Btk enzymatic activity result in XLA syndrome (X-linked agammaglobulinemia), a primary immunodeficiency. Given the critical roles which Tec kinases play in both B-cell and T-cell signaling, Tec kinases are targets of interest for autoimmune disorders.

Consequently, there is a great need in the art for effective inhibitors of Btk.

SUMMARY

A first embodiment of the invention is a compound of Formula (I') or Formula (I):

(I')

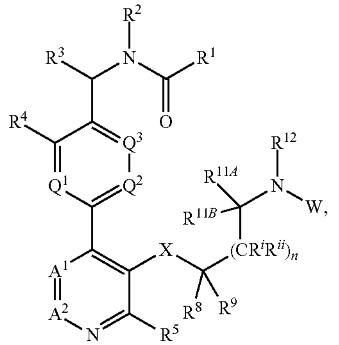

(I)

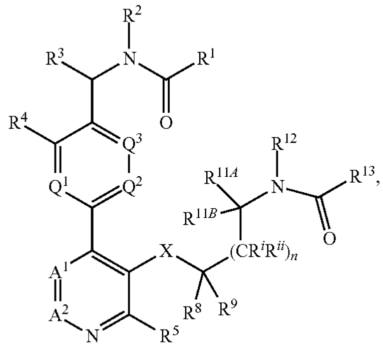

or a pharmaceutically acceptable salt thereof, wherein:

one of $A^1$ and $A^2$ is C—$R^6$, and the other of $A^1$ and $A^2$ is C—$R^6$ or N;

$Q^1$ is selected from C—$R^6$ and N;

$Q^2$ is selected from C—$R^6$ and N;

$Q^3$ is selected from C—$R^6$ and N;

wherein at most one of $Q^1$, $Q^2$, and $Q^3$ is N;

$R^1$ is selected from —$N(R^{1a})_2$, phenyl, 3- to 7-membered saturated or partially unsaturated monocyclic carbocyclyl, 3- to 7-membered saturated or partially unsaturated monocyclic heterocyclyl, 5- to 6-membered heteroaryl, 7- to 10-membered saturated or partially unsaturated bicyclic carbocyclyl, 7- to 10-membered saturated or partially unsaturated bicyclic heterocyclyl, 7- to 10-membered bicyclic heteroaryl, and 8- to 10-membered bicyclic aryl, wherein the phenyl, 3- to 7-membered saturated or partially unsaturated monocyclic carbocyclyl, 3- to 7-membered saturated or partially unsaturated monocyclic heterocyclyl, 5- to 6-membered heteroaryl, 7- to 10-membered saturated or partially unsaturated bicyclic carbocyclyl, 7- to 10-membered saturated or partially unsaturated bicyclic heterocyclyl, and 8- to 10-membered bicyclic aryl represented by $R^1$ are each optionally substituted with one or more $R^{10}$;

$R^{1a}$, for each occurrence, is independently selected from H, $C_{1-6}$ alkyl, $C_{2-6}$ alkenyl, $C_{2-6}$ alkynyl, phenyl, 3- to 7-membered saturated or partially unsaturated carbocyclyl ring, 3- to 7-membered saturated or partially unsaturated monocyclic heterocyclyl, and 5- to 6-membered heteroaryl, wherein the $C_{1-6}$ alkyl, $C_{2-6}$ alkenyl, $C_{2-6}$ alkynyl, phenyl, 3- to 7-membered saturated or partially unsaturated carbocyclyl ring, 3- to 7-membered saturated or partially unsaturated monocyclic heterocyclyl, and 5- to 6-membered heteroaryl represented by $R^{1a}$ are each optionally substituted with one or more $R^{10}$;

or two $R^{1a}$ groups on the same nitrogen are taken together with their intervening atoms to form a ring selected from 3- to 7-membered saturated or partially unsaturated monocyclic heterocyclyl and 5- to 6-membered heteroaryl, wherein the ring is optionally substituted with one or more $R^{10}$;

$R^{10}$, for each occurrence, is independently selected from halogen, —$OR^{10a}$, —$S(O)_2R^{10a}$, —CN, $C_{1-6}$ alkyl, $C_{2-6}$ alkenyl, $C_{2-6}$ alkynyl, 3- to 7-membered saturated or partially unsaturated monocyclic carbocyclyl, and 4- to 6-membered saturated or partially unsaturated monocyclic heterocyclyl; wherein the $C_{1-6}$ alkyl, $C_{2-6}$ alkenyl, $C_{2-6}$ alkynyl, 3- to 7-membered saturated or partially unsaturated monocyclic carbocyclyl, and 4- to 6-membered saturated or partially unsaturated monocyclic heterocyclyl represented by $R^{10}$ are each optionally substituted with one or more $R^{15}$;

$R^{10a}$ is $C_{1-6}$ alkyl optionally substituted with one ore more halogen;

$R^{15}$, for each occurrence, is independently selected from halogen and —$OR^{15a}$;

$R^{15a}$ is $C_{1-6}$ alkyl;

$R^2$ is H, $C_{1-6}$ alkyl, $C_{2-6}$ alkenyl, and $C_{2-6}$ alkynyl, or $R^1$ and $R^2$, together with their intervening atoms, form a Ring B selected from 3- to 7-membered saturated or partially unsaturated monocyclic heterocyclyl, 7- to 10-membered saturated or partially unsaturated bicyclic heterocyclyl, and 7- to 10-membered bicyclic heteroaryl, wherein Ring B is optionally substituted with one or more $R^{100}$;

$R^{100}$, for each occurrence, is independently selected from $C_{1-6}$ alkyl, $C_{2-6}$ alkenyl, $C_{2-6}$ alkynyl, 3- to 7-membered saturated or partially unsaturated monocyclic carbocyclyl, 4- to 6-membered saturated or partially unsaturated monocyclic heterocyclyl and halogen; wherein the $C_{1-6}$ alkyl, $C_{2-6}$ alkenyl, $C_{2-6}$ alkynyl, 3- to 7-membered saturated or partially unsaturated monocyclic carbocyclyl, and saturated or partially unsaturated 4- to 6-membered monocyclic heterocyclyl represented by $R^{100}$ are each optionally substituted with one or more $R^{150}$;

$R^{150}$, for each occurrence, is independently selected from halogen and —$OR^{150a}$;

$R^{150a}$ is $C_{1-6}$ alkyl;

$R^3$ is selected from H, halogen, —$C(O)N(R^{3a})_2$, —$C(O)OR^{3a}$, —$C(O)R^{3a}$, $C_{1-6}$ alkyl, $C_{2-6}$ alkenyl, and $C_{2-6}$ alkynyl, wherein the $C_{1-6}$ alkyl, $C_{2-6}$ alkenyl, and $C_{2-6}$ alkynyl represented by $R^3$ are each optionally substituted with one or more substituents selected from halogen and hydroxyl;

$R^{3a}$, for each occurrence, is independently selected from H, $C_{1-6}$ alkyl, $C_{2-6}$ alkenyl, $C_{2-6}$ alkynyl, phenyl, 3- to 7-membered saturated or partially unsaturated carbocyclyl ring, 3- to 7-membered saturated or partially unsaturated monocyclic heterocyclyl, or 5- to 6-membered heteroaryl, wherein $C_{1-6}$ alkyl, $C_{2-6}$ alkenyl, $C_{2-6}$ alkynyl, phenyl, 3- to 7-membered saturated or partially unsaturated carbocyclyl ring, 3- to 7-membered saturated or partially unsaturated monocyclic heterocyclyl, and 5- to 6-membered heteroaryl are optionally substituted with one or more $R^{30}$;

or two $R^{3a}$ groups on the same nitrogen are taken together with their intervening atoms to form a ring selected from 3- to 7-membered saturated or partially unsaturated monocyclic heterocyclyl and 5- to 6-membered heteroaryl, wherein said ring is optionally substituted with one or more $R^{30}$;

$R^{30}$, for each occurrence, is independently selected from halogen, —$OR^{30a}$, —$N(R^{30a})_2$, —C(O)N($R^{30a}$), —$C(O)_2R^{30a}$, oxo, $C_{1-6}$ alkyl, $C_{2-6}$ alkenyl, $C_{2-6}$ alkynyl, 3- to 7-membered saturated or partially unsaturated monocyclic carbocyclyl, and 4- to 6-membered saturated or partially unsaturated monocyclic heterocyclyl;

$R^{30a}$ is H or $C_{1-6}$ alkyl;

$R^4$ is selected from H, halogen, —$NO_2$, —CN, —$OR^{4a}$, —$SR^{4a}$, —$N(R^{4a})_2$, —$C(O)R^{4a}$, —$C(O)OR^{4a}$, —$S(O)R^{4a}$, —$S(O)_2R^{4a}$, —$C(O)N(R^{4a})_2$, —$SO_2N(R^{4a})_2$, —$OC(O)R^{4a}$, —$N(R^{4a})C(O)R^{4a}$, —$N(R^{4a})C(O)OR^{4a}$, —$N(R^{4a})SO_2R^{4a}$, —$OC(O)N(R^{4a})_2$, $C_{1-6}$ alkyl, $C_{2-6}$ alkenyl and $C_{2-6}$ alkynyl, wherein the $C_{1-6}$ alkyl, $C_{2-6}$ alkenyl and $C_{2-6}$ alkynyl are each optionally substituted with one ore more $R^{40}$.

$R^{4a}$ is H, $C_{1-6}$ alkyl, $C_{2-6}$ alkenyl, $C_{2-6}$alkynyl, phenyl, 3- to 8-membered saturated or partially unsaturated carbocyclyl ring, 3- to 7-membered saturated or partially unsaturated monocyclic heterocyclyl, and 5- to 6-membered heteroaryl, wherein the $C_{1-6}$ alkyl, $C_{2-6}$ alkenyl, $C_{2-6}$ alkynyl, phenyl, 3- to 8-membered saturated or partially unsaturated carbocyclyl ring, 3- to 7-membered saturated or partially unsaturated monocyclic heterocyclyl, and 5- to 6-membered heteroaryl represented by $R^{4a}$ are each optionally substituted with one or more $R^{40}$;

or two $R^{4a}$ groups on the same nitrogen are taken together with their intervening atoms to form a ring selected from 3- to 7-membered saturated or partially unsaturated monocyclic heterocyclyl and 5- to 6-membered heteroaryl, wherein said ring is optionally substituted with one or more $R^{40}$.

$R^{40}$, for each occurrence, is independently selected from halogen, —$OR^{40a}$, —$N(R^{40a})_2$, —$C(O)N(R^{40a})_2$, —$C(O)_2R^{40a}$, oxo, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl; wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{40}$ are each optionally substituted with one or more $R^{45}$;

$R^{40a}$ is H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl are each optionally substituted with one or more $R^{45}$;

$R^{45}$, for each occurrence, is independently selected from $C_{1-6}$ alkyl, halogen and —$OR^{45a}$;

$R^{45a}$ is H or $C_{1-6}$ alkyl;

or $R^3$ and $R^4$, together with their intervening atoms, form a Ring A, wherein Ring A is selected from 5- to 7-membered monocyclic carbocycle and 5- to 7-membered monocyclic heterocycle, wherein Ring A is optionally substituted with $R^{300}$;

$R^{300}$, for each occurrence, is independently selected from $C_{1-6}$ alkyl, $C_{2-6}$ alkenyl, $C_{2-6}$ alkynyl, 3- to 7-membered monocyclic carbocyclyl, 4- to 6-membered monocyclic heterocyclyl, halogen, —$C(O)R^{300a}$, —$OR^{300a}$, and —$S(O)_2R^{300a}$; wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{300}$ are each optionally substituted with one or more $R^{350}$;

$R^{300a}$ is selected from H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{300a}$ are each optionally substituted with one or more $R^{350}$;

$R^{350}$, for each occurrence, is independently selected from $C_{1-6}$ alkyl, halogen, —CN, —C(O)$R^{350a}$, —C(O)N($R^{350a}$)$_2$, —C($R^{350a}$)$_2$N($R^{350a}$)$_2$, and —O$R^{350a}$ $R^{350a}$, for each occurrence, is independently H or $C_{1-6}$ alkyl optionally substituted with one to three halogen;

$R^5$ is selected from H, —NH$R^7$, or —NHC(O)$R^7$;

$R^6$, for each occurrence, is independently selected from H, $C_{1-6}$ alkyl, $C_{2-6}$ alkenyl, $C_{2-6}$ alkynyl, halogen, —$NO_2$, —CN, —O$R^{6a}$, —S$R^{6a}$, —N($R^{6a}$)$_2$, —C(O)$R^{6a}$, —C(O)O$R^{6a}$, —S(O)$R^{6a}$, —S(O)$_2R^{6a}$, —C(O)N($R^{6a}$)$_2$, —SO$_2$N($R^{6a}$)$_2$, —OC(O)$R^{6a}$, —N($R^{6a}$)C(O)$R^{6a}$, —N($R^{6a}$)C(O)O$R^{6a}$, —N($R^{6a}$)SO$_2R^{6a}$, and —OC(O)N($R^{6a}$);

$R^{6a}$ is H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 6-membered monocyclic carbocyclyl and 4- to 6-membered monocyclic heterocyclyl represented by $R^{6a}$ are each optionally substituted with one or more $R^{60}$;

$R^{60}$, for each occurrence, is independently selected from halogen, —O$R^{60a}$, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl; wherein the $C_{1-6}$ alkyl, $C_{2-6}$ alkenyl, $C_{2-6}$ alkynyl, 3- to 7-membered monocyclic carbocyclyl and 4- to 6-membered monocyclic heterocyclyl represented by $R^{60}$ are optionally substituted with one or more $R^{65}$;

$R^{60a}$ is H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{60a}$ are each optionally substituted with one or more $R^{65}$;

$R^{65}$, for each occurrence, is independently selected from $C_{1-6}$ alkyl, halogen and —O$R^{65a}$.

$R^{65a}$ is H or $C_{1-6}$ alkyl;

$R^7$ is H or $C_{1-6}$ alkyl;

X is $CR^{15}R^{16}$, O, $NR^{14}$, S, SO or $SO_2$;

$R^8$, $R^9$, $R^i$, $R^{ii}$, $R^{11A}$ and $R^{11B}$ are each independently H or $C_{1-6}$ alkyl optionally substituted with one or more substituents independently selected from halogen and $C_{1-6}$ alkoxy; or any two of $R^8$, $R^9$, $R^i$, $R^{ii}$, $R^{11A}$ and $R^{11B}$ together with the carbon atom to which they are bound form a 3-8 membered saturated carbocyclic ring;

or alternatively, $R^8$ and $R^9$ together with the carbon atom from which they are attached form a carbonyl —C(═O)— group;

$R^{12}$ is H or $C_{1-6}$ alkyl optionally substituted with one or more substituents independently selected from halogen and $C_{1-6}$ alkoxy;

or $R^{12}$ and any one of $R^8$, $R^9$, $R^i$, $R^{ii}$, $R^{11A}$ and $R^{11B}$ together with the atoms to which they are bound form a 4 to 8-membered azacyclic ring, which ring is optionally substituted with one or more substituents independently selected from halogen, —CN, —OH, $C_{1-6}$ alkyl and $C_{1-6}$ alkoxy;

n is 0 or 1;

W is —C(═O)—$R^{13}$, —SO$_2$—$R^{13}$, or —CN;

$R^{13}$ is $C_{2-6}$ alkenyl, $C_{2-6}$ alkynyl or $C_{2-6}$ alkylenyl oxide, wherein the $C_{2-6}$ alkenyl represented by $R^{13}$ is optionally substituted with one or more substituents independently selected from $C_{1-6}$ alkyl, $C_{1-6}$ alkoxy and —$NR^{13a}R^{13b}$, the $C_{2-6}$ alkynyl represented by $R^{13}$ is optionally substituted by one or more substituents independently selected from $C_{1-6}$ alkyl and $C_{1-6}$ alkoxy, and the $C_{2-6}$ alkylenyl oxide represented by $R^{13}$ is optionally substituted by one or more $C_{1-6}$ alkyl;

$R^{13a}$ and $R^{13b}$ are each independently H or $C_{1-3}$ alkyl;

$R^{14}$ is H or $C_1$-$C_6$ alkyl; and $R^{15}$ and $R^{16}$ are each independently H, $C_{1-6}$alkyl, halogen, or $C_{1-6}$alkoxy, wherein the $C_{1-6}$alkyl and $C_{1-6}$alkoxy are each optionally substituted with one or more halogen.

Alternatively for the first embodiment, $R^8$, $R^9$, $R^i$, $R^{ii}$, $R^{11A}$ and $R^{11B}$ are each independently H or $C_{1-6}$ alkyl optionally substituted with one or more substituents independently selected from halogen and $C_{1-6}$ alkoxy; or any two of $R^8$, $R^9$, $R^i$, $R^{ii}$, $R^{11A}$ and $R^{11B}$ together with the carbon atom to which they are bound form a 3-6 membered saturated carbocyclic ring; and $R^{12}$ is H or $C_{1-6}$ alkyl optionally substituted with one or more substituents independently selected from halogen and $C_{1-6}$ alkoxy;

or $R^{12}$ and any one of $R^8$, $R^9$, $R^i$, $R^1$, $R^{11A}$ and $R^{11B}$ together with the atoms to which they are bound form a 4 to 7-membered azacyclic ring, which ring is optionally substituted with one or more substituents independently selected from halogen, —CN, —OH, $C_{1-6}$ alkyl and $C_{1-6}$ alkoxy; and the remainder of the variables are as described above.

The present invention also provides a pharmaceutical composition comprising at least one compound described herein, or a pharmaceutically acceptable salt thereof, and at least one pharmaceutically acceptable excipient.

In one embodiment, the invention is a method of treating a disorder responsive to inhibition of Btk in a subject comprising administering to the subject an effective amount of at least one compound described herein, or a pharmaceutically acceptable salt thereof, or a pharmaceutical composition described herein.

The present invention also includes the use of at least one compound described herein, or a pharmaceutically acceptable salt thereof, for the manufacture of a medicament for the treatment of a disorder responsive to inhibition of Btk. Also provided is a compound described herein, or a pharmaceutically acceptable salt thereof, or a pharmaceutical composition described herein for use in treating a disorder responsive to inhibition of Btk.

Other features or advantages will be apparent from the following detailed description of several embodiments, and also from the appended claims.

DETAILED DESCRIPTION

The compounds or pharmaceutically acceptable salts thereof as described herein, can have activity as Btk modulators. In particular, compounds or pharmaceutically acceptable salts thereof as described herein, can be Btk inhibitors.

In a second embodiment, a compound of the present invention is represented by Formula (I') or Formula (I), or a pharmaceutically acceptable salt thereof, wherein $Q^1$, $Q^2$ and $Q^3$ are C—$R^6$; and the definitions for the other variables are as defined in the first embodiment.

In a third embodiment, a compound of the present invention is represented by Formula (I') or Formula (I), or a pharmaceutically acceptable salt thereof, wherein $A^1$ is N and $A^2$ is C—$R^6$; and the definitions for the other variables are as defined in the first or second embodiment.

In a fourth embodiment, a compound of the present invention is represented by Formula (I') or Formula (I), or a pharmaceutically acceptable salt thereof, wherein $A^1$ and $A^2$ are both C—$R^6$; and the definitions for the other variables are as defined in the first or second embodiment.

In a fifth embodiment, a compound of the present invention is represented by Formula (II) or Formula (III):

(II)

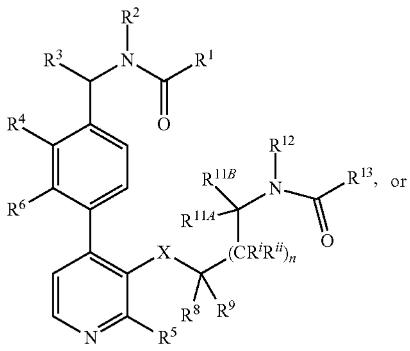

or (III)

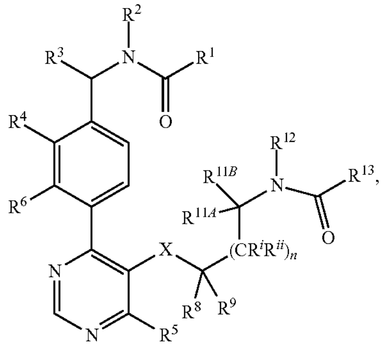

or a pharmaceutically acceptable salt thereof; and the definitions for the variables are as defined in the first, second, third, or fourth embodiment.

In a sixth embodiment, a compound of the present invention is represented by Formula (I'), (I), (II), or (III), or a pharmaceutically acceptable salt thereof, wherein $R^1$ is a 3- to 7-membered saturated or partially unsaturated monocyclic heterocyclyl having 1-2 heteroatoms independently selected from O, N and S, or a 5- to 6-membered heteroaryl having 1-4 heteroatoms independently selected from O, N and S, wherein the 3- to 7-membered saturated or partially unsaturated monocyclic heterocyclyl and 5- to 6-membered heteroaryl represented by $R^1$ are optionally substituted with one or two $R^{10}$; and the definitions for the other variables are as defined in the first, second, third, fourth, or fifth embodiment.

In a seventh embodiment, a compound of the present invention is represented by Formula (I'), (I), (II), or (III), or a pharmaceutically acceptable salt thereof, wherein $R^1$ is a 5-membered heteroaryl optionally substituted with one or two $R^{10}$; and the definitions for the other variables are as defined in the first, second, third, fourth, fifth, or sixth embodiment.

In an eighth embodiment, a compound of the present invention is represented by Formula (I'), (I), (II), or (III), or a pharmaceutically acceptable salt thereof, wherein $R^1$ is a 5-membered heteroaryl selected from pyrazolyl, oxazolyl, isoxazolyl, 1,2,3-oxadiazolyl, 1,3,4-oxadiazolyl, 1,2,4-oxadizolyl, 1,2,3-thiadiazolyl, 1,3,4-thiadiazolyl, 1,2,4-thiadiazolyl, 1,2,3-triazolyl, 1,2,4-triazolyl, and tetrazolyl, each of which is optionally substituted with one or two $R^{10}$; and the definitions for the other variables are as defined in the first, second, third, fourth, fifth, or sixth embodiment.

In a ninth embodiment, a compound of the present invention is represented by Formula (I'), (I), (II), or (III), or a pharmaceutically acceptable salt thereof, wherein $R^1$ is represented by the following formula:

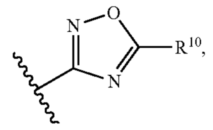 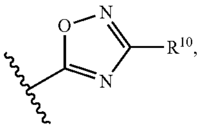

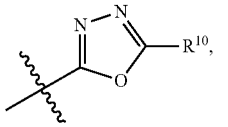 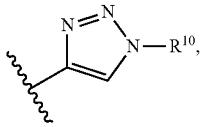

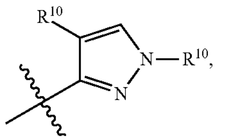 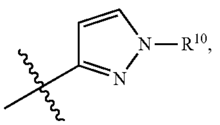

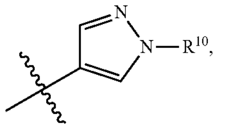 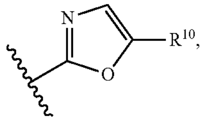

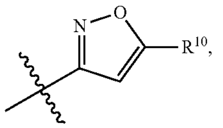 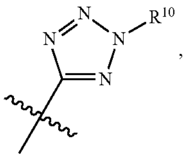 ,

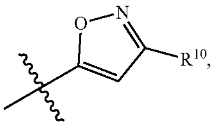 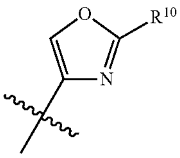 or

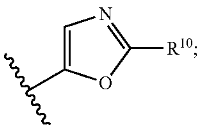

and the definitions for the other variables are as defined in the first, second, third, fourth, fifth, or sixth embodiment.

In a tenth embodiment, a compound of the present invention is represented by Formula (I'), (I), (II), or (III), or a pharmaceutically acceptable salt thereof, wherein $R^{10}$, for each occurrence, is independently selected from halogen, —$OR^{10a}$, —$S(O)_2R^{10a}$, —CN, $C_{1-6}$ alkyl, $C_{3-6}$ cycloalkyl, and phenyl; wherein the $C_{1-6}$ alkyl, $C_{3-6}$ cycloalkyl, and phenyl represented by $R^{10}$ are each optionally substituted with one to three $R^{15}$; $R^{10a}$, for each occurrence, is independently selected from H and $C_{1-3}$ alkyl; $R^{15}$, for each occurrence, is independently selected from $C_{1-6}$alkyl, halogen, —CN and —$OR^{15a}$; $R^{15a}$ is H or $C_{1-3}$ alkyl; and the definitions for the other variables are as defined in the first, second, third, fourth, fifth, sixth, seventh, eighth, or ninth embodiment.

In an eleventh embodiment, a compound of the present invention is represented by Formula (I'), (I), (II), or (III), or a pharmaceutically acceptable salt thereof, wherein $R^{10}$, for each occurrence, is independently $C_{1-6}$ alkyl optionally substituted with one to three halogen; and the definitions for the other variables are as defined in the first, second, third, fourth, fifth, sixth, seventh, eighth, ninth, or tenth embodiment.

In a twelfth embodiment, a compound of the present invention is represented by Formula (I'), (I), (II), or (III), or a pharmaceutically acceptable salt thereof, wherein $R^{10}$, for each occurrence, is independently —$C(CH_3)_3$ or —$C(CH_3)_2CH_2F$; and the definitions for the other variables are as defined in the first, second, third, fourth, fifth, sixth, seventh, eighth, ninth, tenth, or eleventh embodiment.

In a thirteenth embodiment, a compound of the present invention is represented by Formula (I'), (I), (II), or (III), or a pharmaceutically acceptable salt thereof, wherein $R^2$ is H or $C_{1-3}$ alkyl; and the definitions for the other variables are as defined in the first, second, third, fourth, fifth, sixth, seventh, eighth, ninth, tenth, eleventh, or twelfth embodiment.

In a fourteenth embodiment, a compound of the present invention is represented by Formula (I'), (I), (II), or (III), or a pharmaceutically acceptable salt thereof, wherein $R^2$ is H or methyl; and the definitions for the other variables are as defined in the first, second, third, fourth, fifth, sixth, seventh, eighth, ninth, tenth, eleventh, twelfth, or thirteenth embodiment.

In a fifteenth embodiment, a compound of the present invention is represented by Formula (I'), (I), (II), or (III), or a pharmaceutically acceptable salt thereof, wherein $R^1$ and $R^2$, together with their intervening atoms, form a Ring B selected from 3- to 7-membered saturated or partially unsaturated monocyclic heterocyclyl having 1-2 heteroatoms independently selected from O, N and S, 5- to 6-membered heteroaryl having 1-4 heteroatoms independently selected from O, N and S, 7- to 10-membered bicyclic heterocyclyl having 1-4 heteroatoms independently selected from O, N and S, and 7- to 10-membered bicyclic heteroaryl having 1-4 heteroatoms independently selected from O, N and S, wherein Ring B is optionally substituted with one or two $R^{100}$; and the definitions for the other variables are as defined in the first, second, third, fourth, fifth, sixth, seventh, eighth, ninth, tenth, eleventh, twelfth, thirteenth, or fourteenth embodiment.

In a sixteenth embodiment, a compound of the present invention is represented by Formula (I'), (I), (II), or (III), or a pharmaceutically acceptable salt thereof, wherein $R^1$ and $R^2$, together with their intervening atoms, form Ring B as defined in the fifteenth embodiment, wherein Ring B is represented by one of following formulae:

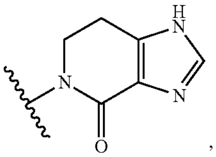,
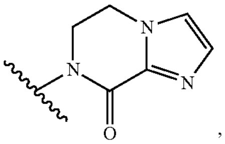,
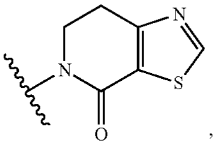,
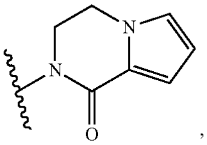,
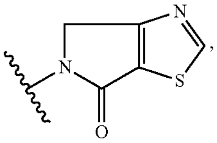,
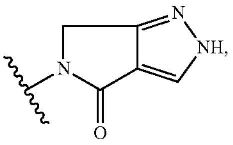
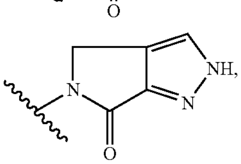
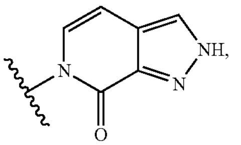
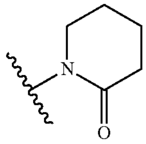,
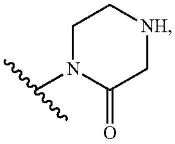
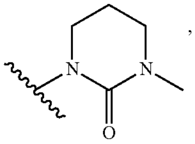,
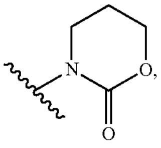
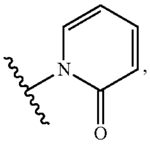,
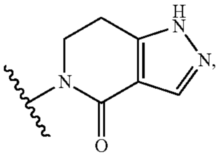
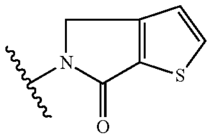,
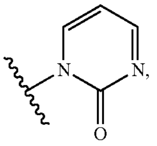 or
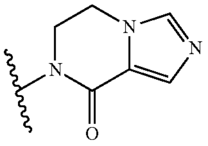 [SMILES: *N1CCn2cncc2C1=O]

wherein Ring B is optionally substituted with one or two $R^{100}$; and the definitions for the other variables are as defined in the first, second, third, fourth, fifth, sixth, seventh, eighth, ninth, tenth, eleventh, twelfth, thirteenth, fourteenth, or fifteenth embodiment.

In a seventeenth embodiment, a compound of the present invention is represented by Formula (I'), (I), (II), or (III), or a pharmaceutically acceptable salt thereof, wherein $R^1$ and $R^2$, together with their intervening atoms, form Ring B as defined in the fifteenth or sixteenth embodiment, wherein Ring B is optionally substituted with one or two $R^{100}$, wherein $R^{100}$, for each occurrence, is independently selected from $C_{1-6}$ alkyl, $C_{3-6}$ cycloalkyl, halogen, —CN, and —$OR^{100a}$, wherein the $C_{1-6}$ alkyl and $C_{3-6}$ cycloalkyl are each optionally substituted with one to three substituents independently selected from halogen and $C_{1-3}$ alkyl, and $R^{100a}$, for each occurrence, is independently selected from H, $C_{1-6}$ alkyl, $C_{3-6}$ cycloalkyl, and 4- to 6-membered monocyclic heterocyclyl; and the definitions for the other variables are as defined in the first, second, third, fourth, fifth, sixth, seventh, eighth, ninth, tenth, eleventh, twelfth, thirteenth, fourteenth, fifteenth, or sixteenth embodiment.

In an eighteenth embodiment, a compound of the present invention is represented by Formula (I'), (I), (II), or (III), or a pharmaceutically acceptable salt thereof, wherein $R^1$ and $R^2$, together with their intervening atoms, form Ring B as defined in the fifteenth or sixteenth embodiment, wherein Ring B is optionally substituted with one or two $R^{100}$, wherein $R^{100}$, for each occurrence, is independently $C_{1-6}$ alkyl or $C_{3-6}$ cycloalkyl, wherein the $C_{1-6}$ alkyl and $C_{3-6}$ cycloalkyl are each optionally substituted with one to three substituents independently selected from halogen and $C_{1-3}$ alkyl; and the definitions for the other variables are as defined in the first, second, third, fourth, fifth, sixth, seventh, eighth, ninth, tenth, eleventh, twelfth, thirteenth, fourteenth, fifteenth, sixteenth, or seventeenth embodiment.

In a nineteenth embodiment, a compound of the present invention is represented by Formula (I'), (I), (II), or (III), or a pharmaceutically acceptable salt thereof, wherein $R^1$ and $R^2$, together with their intervening atoms, form Ring B as defined in the fifteenth or sixteenth embodiment, wherein Ring B is optionally substituted with one or two $R^{100}$, wherein $R^{100}$, for each occurrence, is independently $—C(CH_3)_3$, $—CH_2C(CH_3)_3$ or cyclopropyl; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, or eighteenth embodiment.

In a twentieth embodiment, a compound of the present invention is represented by Formula (I'), (I), (II), or (III), or a pharmaceutically acceptable salt thereof, wherein $R^3$ is H; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, or nineteenth embodiment.

In a twenty-first embodiment, a compound of the present invention is represented by Formula (I'), (I), (II), or (III), or a pharmaceutically acceptable salt thereof, wherein $R^4$ is selected from H, halogen, —CN, $—OR^{4a}$, $C_{1-6}$ alkyl, and $C_{3-6}$ cycloalkyl, wherein the $C_{1-6}$ alkyl and $C_{3-6}$ cycloalkyl represented by $R^4$ are each optionally substituted with one to three halogen; and $R^{4a}$ is $C_{1-4}$ alkyl optionally substituted with one to three halogen; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, or twentieth embodiment.

In a twenty-second embodiment, a compound of the present invention is represented by Formula (I'), (I), (II), or (III), or a pharmaceutically acceptable salt thereof, wherein $R^4$ is selected from H, halogen, $—OR^{4a}$ and $C_{1-6}$ alkyl optionally substituted with one to three halogen; and $R^{4a}$ is $C_{1-4}$ alkyl optionally substituted with one or three halogen; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, or twenty-first embodiment.

In a twenty-third embodiment, a compound of the present invention is represented by Formula (I'), (I), (II), or (III), or a pharmaceutically acceptable salt thereof, wherein $R^4$ is H, $—CH_3$, $—CF_3$, $—CHF_2$, —Cl, —F or $—OCF_3$; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, or twenty-second embodiment.

In a twenty-fourth embodiment, a compound of the present invention is represented by Formula (I'), (I), (II), or (III), or a pharmaceutically acceptable salt thereof, wherein $R^3$ and $R^4$, together with their intervening atoms, form a Ring A, wherein Ring A is selected from 5- to 7-membered monocyclic carbocycle and 5- to 7-membered monocyclic heterocycle, wherein Ring A is optionally substituted with $R^{300}$; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, or nineteenth embodiment.

In a twenty-fifth embodiment, a compound of the present invention is represented by Formula (I'), (I), (II), or (III), or a pharmaceutically acceptable salt thereof, wherein $R^3$ and $R^4$, together with their intervening atoms, form a Ring A as defined in the twenty-fourth embodiment, wherein Ring A is a 7-membered monocyclic carbocycle or 7-membered monocyclic heterocycle having one heteroatom that is O or N, wherein Ring A is optionally substituted with $R^{300}$; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, or twenty-fourth embodiment.

In a twenty-sixth embodiment, a compound of the present invention is represented by Formula (I'), (I), (II), or (III), or a pharmaceutically acceptable salt thereof, wherein $R^6$ is H or halogen; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, or twenty-fifth embodiment.

In a twenty-seventh embodiment, a compound of the present invention is represented by Formula (I'), (I), (II), or (III), or a pharmaceutically acceptable salt thereof, wherein $R^6$ is H or F; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, or twenty-sixth embodiment.

In a twenty-eighth embodiment, a compound of the present invention is represented by Formula (I'), (I), (II), or (III), or a pharmaceutically acceptable salt thereof, wherein $R^5$ is H or $—NHR^7$; and $R^7$ is H or $C_{1-3}$ alkyl; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, or twenty-seventh embodiment.

In a twenty-ninth embodiment, a compound of the present invention is represented by Formula (I'), (I), (II), or (III), or a pharmaceutically acceptable salt thereof, wherein $R^5$ is H or $—NH_2$; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, or twenty-eighth embodiment.

In a thirtieth embodiment, a compound of the present invention is represented by Formula (I'), (I), (II), or (III), or a pharmaceutically acceptable salt thereof, wherein X is O; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, or twenty-ninth embodiment.

In a thirty-first embodiment, a compound of the present invention is represented by Formula (I'), (I), (II), or (III), or a pharmaceutically acceptable salt thereof, wherein X is $NR^{14}$, wherein $R^{14}$ is H or methyl; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth or twenty-ninth embodiment.

In a thirty-second embodiment, a compound of the present invention is represented by Formula (I'), (I), (II), or (III), or a pharmaceutically acceptable salt thereof, wherein n is 0; and $R^8$, $R^9$, $R^{11A}$ and $R^{11B}$ are each independently H or $C_{1-3}$ alkyl; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth or thirty-first embodiment.

In a thirty-third embodiment, a compound of the present invention is represented by Formula (I'), (I), (II), or (III), or a pharmaceutically acceptable salt thereof, wherein $R^{12}$ is H or $C_{1-3}$ alkyl; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first or thirty-second embodiment.

In a thirty-fourth embodiment, a compound of the present invention is represented by Formula (I'), (I), (II), or (III), or a pharmaceutically acceptable salt thereof, wherein $R^{12}$ is methyl; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second or thirty-third embodiment.

In a thirty-fifth embodiment, a compound of the present invention is represented by Formula (I'), (I), (II), or (III), or a pharmaceutically acceptable salt thereof, wherein $R^{12}$ and any one of $R^{11A}$ and $R^{11B}$ together with the atoms to which they are bound form a 4 to 8-membered azacyclic ring, wherein the 4 to 8-membered azacyclic ring is optionally substituted with one to three substituents independently selected from halogen, —CN, —OH, $C_{1-6}$ alkyl and $C_{1-6}$ alkoxy; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, or thirty-fourth embodiment.

In a thirty-sixth embodiment, a compound of the present invention is represented by Formula (I'), (I), (II), or (III), or a pharmaceutically acceptable salt thereof, wherein $R^{12}$ and any one of $R^{i}$ and $R^{ii}$ together with the atoms to which they are bound form a 4 to 7-membered azacyclic ring, wherein the 4 to 7-membered azacyclic ring is optionally substituted with one to three substituents independently selected from halogen, —CN, —OH, $C_{1-6}$ alkyl and $C_{1-6}$ alkoxy; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-fourth, or thirty-fifth embodiment.

In a thirty-seventh embodiment, a compound of the present invention is represented by Formula (I'), (I), (II), or (III), or a pharmaceutically acceptable salt thereof, wherein $R^{12}$ and any one of $R^8$ and $R^9$ together with the atoms to which they are bound form a 4 to 7-membered azacyclic ring, which ring is optionally substituted with one to three substituents independently selected from halogen, —CN, —OH, $C_{1-6}$ alkyl and $C_{1-6}$ alkoxy; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-fourth, thirty-fifth, or thirty-sixth embodiment.

In a thirty-eighth embodiment, a compound of the present invention is represented by Formula (I'), (I), (II), or (III), or a pharmaceutically acceptable salt thereof, wherein the azacyclic ring, as defined in the thirty-fourth embodiment, is azetidine, pyrrolidine, or piperidine; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, or thirty-fourth, thirty-fifth, thirty-sixth or thirty-seventh embodiment.

In a thirty-ninth embodiment, a compound of the present invention is represented by Formula (I'), (I), (II), or (III), or a pharmaceutically acceptable salt thereof, wherein $R^{13}$ is $C_{2-6}$ alkenyl optionally substituted with $C_{1-6}$ alkyl, $C_{1-6}$ alkoxy or $—NR^{13a}R^{13b}$, and $R^{13a}$ and $R^{13b}$ are each independently H or $C_{1-3}$ alkyl; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-fourth, thirty-fifth, thirty-sixth, thirty-seventh or thirty-eighth embodiment.

In a fortieth embodiment, a compound of the present invention is represented by Formula (I'), (I), (II), or (III), or a pharmaceutically acceptable salt thereof, wherein $R^{13}$ is $—CH{=}CH_2$ or $—CH{=}CH_2CH_2N(CH_3)_2$; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, thirty-first, thirty-second, thirty-third, thirty-fourth, thirty-fifth, thirty-sixth, thirty-seventh, thirty-eighth or thirty-ninth embodiment.

In a forty-first embodiment, a compound of the present invention is represented by the following formula:

(IIA)

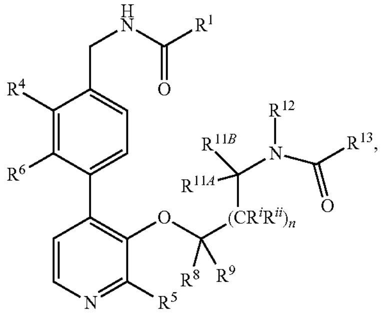

or (IIIA)

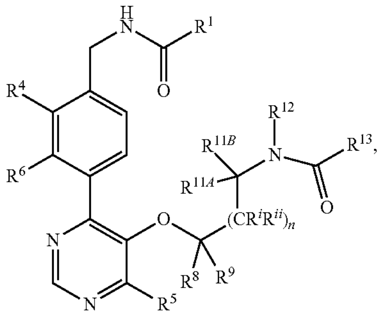

or a pharmaceutically acceptable salt thereof, wherein:

$R^1$ is represented by the following formula:

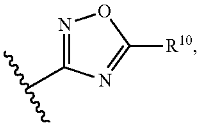
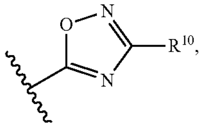
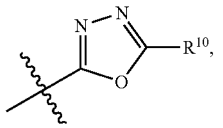
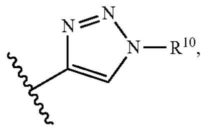
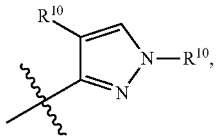
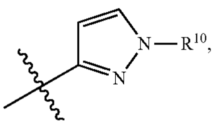
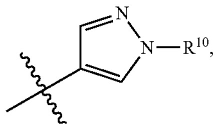
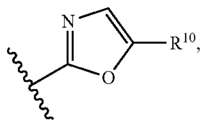

-continued

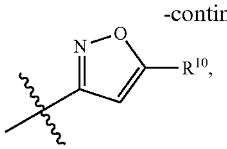
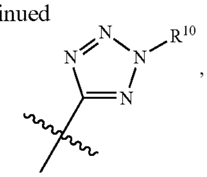
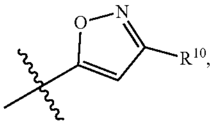
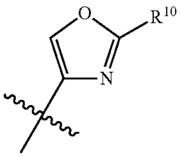

or

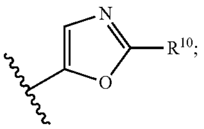

$R^{10}$, for each occurrence, is independently $C_{1-6}$ alkyl optionally substituted with one to three halogen;

$R^4$ is selected from H, halogen, —$OR^{4a}$ and $C_{1-6}$ alkyl optionally substituted with one or three halogen;

$R^{4a}$ is $C_{1-4}$ alkyl optionally substituted with one or three halogen;

$R^5$ is H or —$NH_2$;

$R^6$ is H or halogen;

$R^8$, $R^9$, $R^i$, $R^{ii}$, $R^{11A}$ and $R^{11B}$ are each independently H or $C_{1-3}$ alkyl;

$R^{12}$ is $C_{1-3}$ alkyl;

or $R^{12}$ and any one of $R^8$ and $R^9$ together with the atoms to which they are bound form a 4 to 7-membered azacyclic ring, which ring is optionally substituted with one or more substituents independently selected from halogen, —CN, —OH, $C_{1-6}$ alkyl and $C_{1-6}$ alkoxy; and $R^{13}$ is $C_{2-6}$ alkenyl optionally substituted with $C_{1-6}$ alkyl, $C_{1-6}$ alkoxy or —$NR^{13a}R^{13b}$, and $R^{13a}$ and $R^{13b}$ are each independently H or $C_{1-3}$ alkyl; and the definitions for the other variables are as defined in the first embodiment.

In a forty-second embodiment, a compound of the present invention is represented by the following formula:

(IIB)

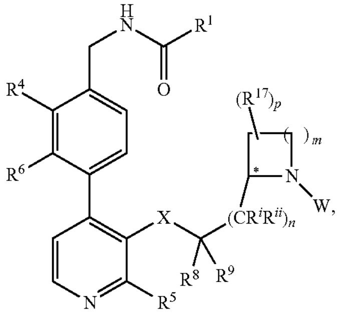

-continued (IIIB)

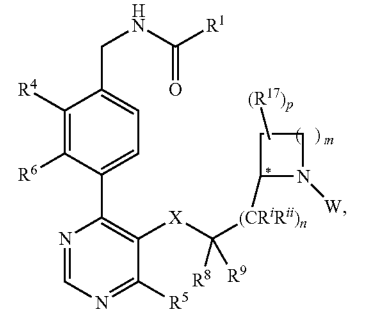

(IIC)

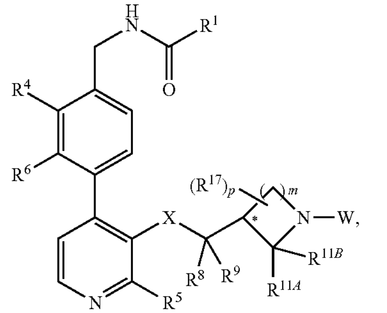

(IIIC)

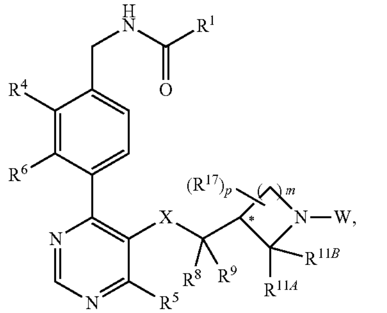

(IID)

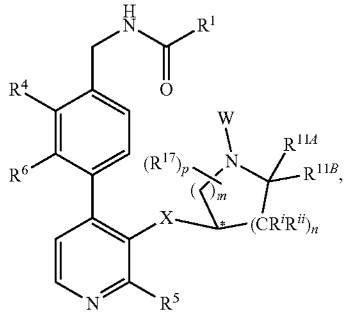

or (IIID)

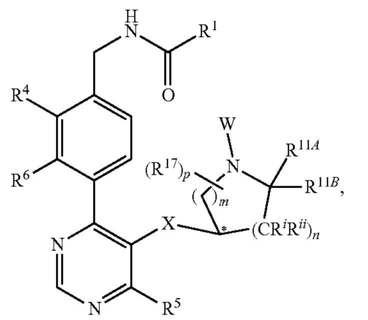

or a pharmaceutically acceptable salt thereof, wherein:

$R^1$ is represented by the following formula:

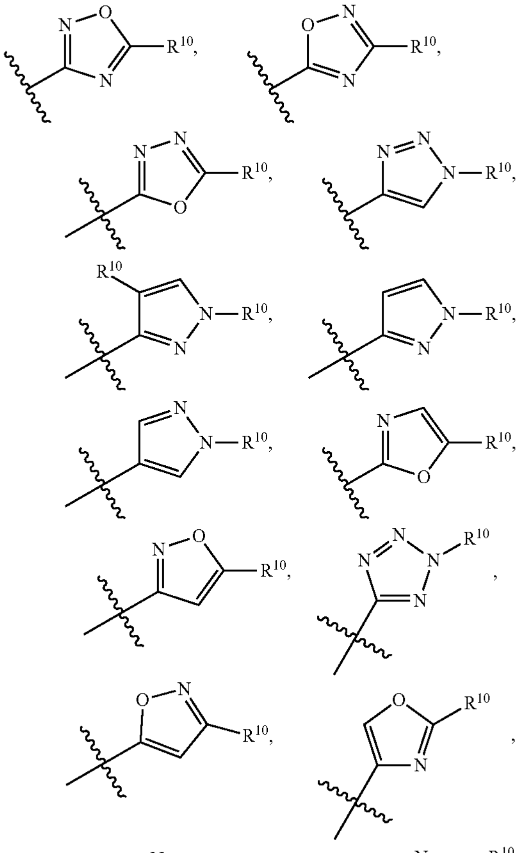

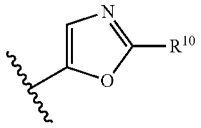

or

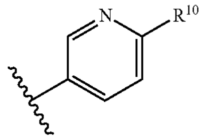

;

$R^4$ is selected from H, halogen, —$OR^{4a}$ and $C_{1-6}$ alkyl optionally substituted with one or three halogen;

$R^{4a}$ is $C_{1-4}$ alkyl optionally substituted with one or three halogen;

$R^5$ is H or —$NH_2$;

$R^6$ is H or halogen;

$R^8$, $R^9$, $R^i$, $R^{ii}$, $R^{11A}$ and $R^{11B}$ are each independently H or $C_{1-3}$ alkyl;

or alternatively, $R^8$ and $R^9$ together with the carbon atom from which they are attached form a carbonyl —C(═O)— group;

$R^{10}$, for each occurrence, is independently $C_{1-6}$ alkyl optionally substituted with one to three halogen;

$R^{13}$ is $C_{2-6}$ alkenyl or $C_{2-6}$ alkynyl, wherein each of the $C_{2-6}$ alkenyl or the $C_{2-6}$ alkynyl represented by $R^{13}$ is optionally substituted with $C_{1-6}$ alkyl, $C_{1-6}$ alkoxy or —$NR^{13a}R^{13b}$;

$R^{13a}$ and $R^{13b}$ are each independently H or $C_{1-3}$ alkyl;

$R^{17}$ is halogen, —CN, —OH, $C_{1-6}$ alkyl or $C_{1-6}$ alkoxy;

X is $CR^{15}R^{16}$, O, $NR^{14}$, S, SO or $SO_2$;

W is —C(═O)—$R^{13}$, —$SO_2$—$R^{13}$, or —CN;

m is 1, 2, 3 or 4;

n is 0 or 1;

p is 0, 1, 2 or 3, and the definitions for the other variables are as defined in the first embodiment.

In a forty-third embodiment, a compound of the present invention is represented by Formula (I'), (I), (IIB), (IIIB), (IIC), (IIIC), (IID) or (IIID), or a pharmaceutically acceptable salt thereof, wherein X is $NR^{14}$ or O, wherein $R^{14}$ is H or methyl; and the definitions for the other variables are as defined in the first or forty-second embodiment.

In a forty-fourth embodiment, a compound of the present invention is represented by Formula (I'), (I), (IIB), (IIIB), (IIC), (IIIC), (IID) or (IIID), or a pharmaceutically acceptable salt thereof, wherein p is 0; and the definitions for the other variables are as defined in the first, forty-second or forty-third embodiment.

In a forty-fifth embodiment, a compound of the present invention is represented by Formula (I'), (I), (IIB), (IIIB), (IIC), (IIIC), (IID) or (IIID), or a pharmaceutically acceptable salt thereof, wherein $R^1$ is represented by one of the following formulae:

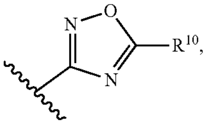 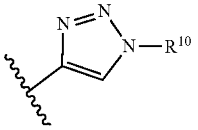 and

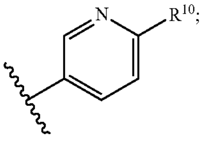

and the definitions for the other variables are as defined in the first, forty-second, forty-third or forty-fourth embodiment.

In a forty-sixth embodiment, a compound of the present invention is represented by Formula (I'), (I), (IIB), (IIIB), (IIC), (IIIC), (IID) or (IIID), or a pharmaceutically acceptable salt thereof, wherein:

$R^4$ is H or $CH_3$;

$R^5$ is H;

$R^8$, $R^9$, $R^i$, $R^{ii}$, $R^{11A}$ and $R^{11B}$ are H;

or alternatively, $R^8$ and $R^9$ together with the carbon atom from which they are attached form a carbonyl —C(═O)— group;

$R^{10}$ is tert-butyl or —$CF_3$ and m is 1, 2 or 3; and the definitions for the other variables are as defined in the first, forty-second, forty-third, forty-fourth or forty-fifth embodiment.

In a forty-seventh embodiment, a compound of the present invention is represented by Formula (I'), (I), (IIB), (IIIB), (IIC), (IIIC), (IID) or (IIID), or a pharmaceutically acceptable salt thereof, wherein: $R^{13}$ is $C_{2-3}$ alkenyl or $C_{2-3}$ alkynyl, wherein each of the $C_{2-3}$ alkenyl or the $C_{2-3}$ alkynyl represented by $R^{13}$ is optionally substituted with —N$(CH_3)_2$; and the definitions for the other variables are as defined in the first, forty-second, forty-third, forty-fourth, forty-fifth or forty-sixth embodiment.

In a forty-eighth embodiment, a compound of the present invention is represented by Formula (I'), (I), (IIB), (IIIB), (IIC), (IIIC), (IID) or (IIID), or a pharmaceutically acceptable salt thereof, wherein:

$R^{13}$ is represented by one of the following formulae:

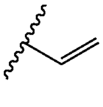 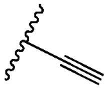 and 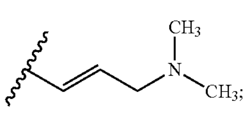

and the definitions for the other variables are as defined in the first, forty-second, forty-third, forty-fourth, forty-fifth, forty-sixth or forty-seventh embodiment.

In a forty-ninth embodiment, a compound of the present invention is represented by Formula (IIB), (IIIB), (IIC), (IIIC), (IID) or (IIID), or a pharmaceutically acceptable salt thereof, wherein the absolute stereochemistry at the carbon atom marked by "*" is S; and the definitions for the other variables are as defined in the first, forty-second, forty-third, forty-fourth, forty-fifth, forty-sixth, forty-seventh or forty-eighth embodiment.

In a fiftieth embodiment, a compound of the present invention is represented by Formula (IIB), (IIIB), (IIC), (IIIC), (IID) or (IIID), or a pharmaceutically acceptable salt thereof, wherein the absolute stereochemistry at the carbon atom marked by "*" is R; and the definitions for the other variables are as defined in the first, forty-second, forty-third, forty-fourth, forty-fifth, forty-sixth, forty-seventh or forty-eighth embodiment.

In a fifty-first embodiment, a compound of the present invention is represented by the following formula:

(IV)

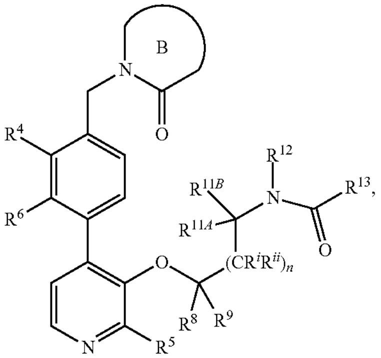

or (V)

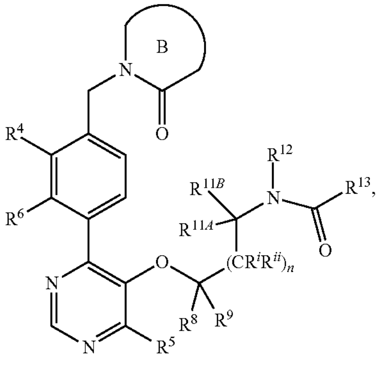

or a pharmaceutically acceptable salt thereof, wherein:

Ring B is represented by one of following formulae:

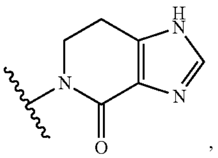 , 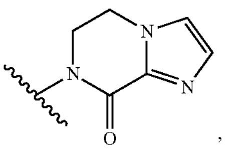 ,

-continued

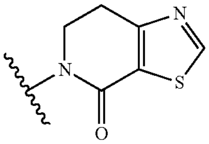 , 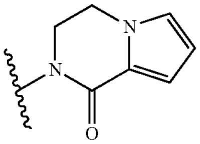 ,

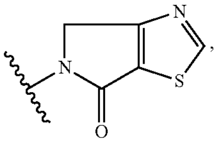 , 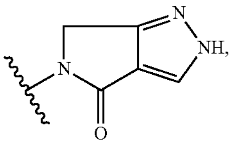

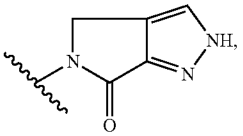 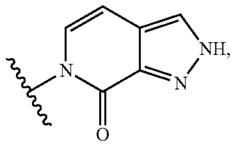

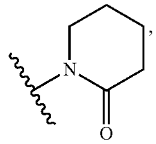 , 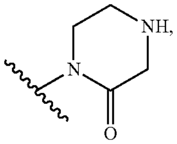 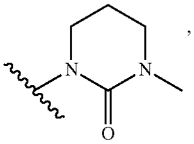 ,

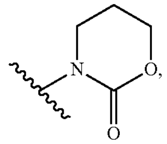 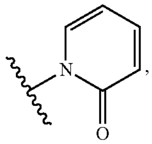 , 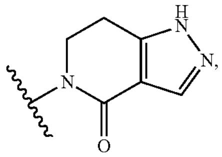

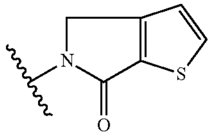 , 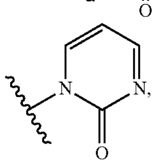 or

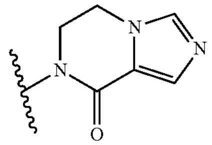 [SMILES: *N1CCn2cncc2C1=O]

wherein Ring B is optionally substituted with one or two $R^{100}$;

$R^{100}$ is $C_{1-6}$ alkyl or $C_{3-6}$ cycloalkyl;

$R^4$ is selected from H, halogen, —$OR^{4a}$ and $C_{1-6}$ alkyl optionally substituted with one or three halogen;

$R^{4a}$ is $C_{1-4}$ alkyl optionally substituted with one or three halogen;

$R^5$ is H or —$NH_2$;

$R^6$ is H or halogen;

$R^8$, $R^9$, $R^i$, $R^{ii}$, $R^{11A}$ and $R^{11B}$ are each independently H or $C_{1-3}$ alkyl;

$R^{12}$ is $C_{1-3}$ alkyl;

or $R^{12}$ and any one of $R^8$ and $R^9$ together with the atoms to which they are bound forms a 4 to 7-membered azacyclic ring, which ring is optionally substituted with one or more substituents independently selected from halogen, —CN, —OH, $C_{1-6}$ alkyl and $C_{1-6}$ alkoxy;

$R^{13}$ is $C_{2-6}$ alkenyl optionally substituted with $C_{1-6}$ alkyl, $C_{1-6}$ alkoxy or —$NR^{13a}R^{13b}$, and $R^{13a}$ and $R^{13b}$ are each independently H or $C_{1-3}$ alkyl; and the definitions for the other variables are as defined in the first embodiment.

In a fifty-second embodiment, a compound of the present invention is represented by Formula (IV) or (V), wherein Ring B is represented by one of the following formulae:

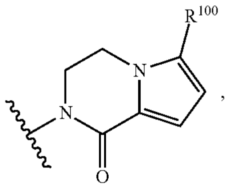 , 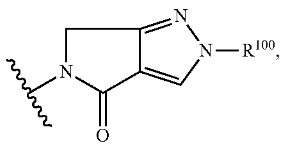

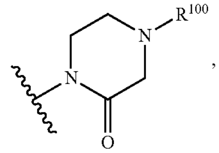 , 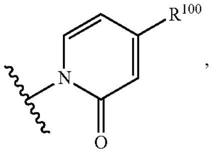 ,

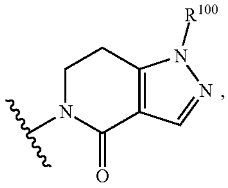 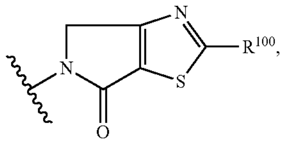

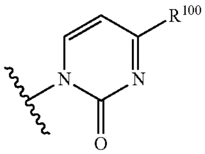 , 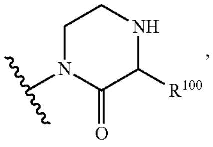 ,

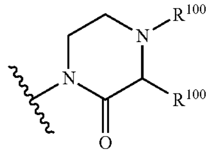 or 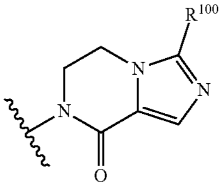

wherein any one of which is optionally substituted with one or two $R^{100}$; and the definitions for the other variables are as defined in the first or fifty-first embodiment.

In a fifty-third embodiment, a compound of the present invention is represented by Formula (I), (II), or (III), or a pharmaceutically acceptable salt thereof, wherein X is $NR^{14}$; $R^8$ and $R^9$ together with the carbon atom from which they are attached form a carbonyl —C(═O)— group; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirty-first, thirty-third, thirty-fifth, thirty-sixth, thirty-seventh, thirty-eighth, thirty-ninth of fortieth embodiment.

As used herein, the term "alkyl" refers to a fully saturated branched or unbranched hydrocarbon moiety. Preferably the alkyl comprises 1 to 6 carbon atoms, or 1 to 4 carbon atoms. In some embodiments, an alkyl comprises from 6 to 20 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, or n-hexyl.

"Alkenyl" refers to an unsaturated hydrocarbon group which may be linear or branched and has at least one carbon-carbon double bond. Alkenyl groups with 2-6 carbon atoms can be preferred. The alkenyl group may contain 1, 2 or 3 carbon-carbon double bonds, or more. Examples of alkenyl groups include ethenyl, n-propenyl, iso-propenyl, n-but-2-enyl, n-hex-3-enyl and the like.

"Alkynyl" refers to an unsaturated hydrocarbon group which may be linear or branched and has at least one carbon-carbon triple bond. Alkynyl groups with 2-6 carbon atoms can be preferred. The alkynyl group may contain 1, 2 or 3 carbon-carbon triple bonds, or more. Examples of alkynyl groups include ethynyl, n-propynyl, n-but-2-ynyl, n-hex-3-ynyl and the like.

The number of carbon atoms in a group is specified herein by the prefix "$C_{x-xx}$", wherein x and xx are integers. For example, "$C_{1-4}$alkyl" is an alkyl group which has from 1 to 4 carbon atoms.

"Halogen" or "halo" may be fluoro, chloro, bromo or iodo.

As used herein, the term "heterocyclyl" refers to a saturated or unsaturated, monocyclic or bicyclic (e.g., fused, bridged or spiro ring systems) ring system which has from 3- to 10-ring members, or in particular 7- to 10-ring members, 3- to 8-ring members, 3- to 7-ring members, 3- to 6-ring members or 5- to 7-ring members, 4- to 7-ring members or 4- to 6-ring members, at least one of which is a heteroatom, and up to 4 (e.g., 1, 2, 3, or 4) of which may be heteroatoms, wherein the heteroatoms are independently selected from O, S and N, and wherein C can be oxidized (e.g., C(O)), N can be oxidized (e.g., N(O)) or quaternized, and S can be optionally oxidized to sulfoxide and sulfone. Unsaturated heterocyclic rings include heteroaryl rings. The term azacyclic refers to the heterocyclyl, wherein the heteroatoms are N.

In one embodiment, a heterocyclyl is a 3- to 7-membered monocyclic heterocyclyl (saturated or partially unsaturated (i.e., non-aromatic)) having 1-2 heteroatoms selected from O, S and N. Examples of 3- to 7-membered monocyclic heterocyclyl include, but are not limited to, aziridinyl, oxiranyl, thirranyl, oxaziridinyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, thiepanyl, dihydrofuranyl, imidazolinyl, and dihydropyranyl. In one embodiment, a heterocyclyl is a 5- to 7-membered monocyclic heterocyclyl (saturated or partially unsaturated). Examples include pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, thiepanyl, dihydrofuranyl, imidazolinyl, and dihydropyranyl.

In one embodiment, a heterocyclyl is a 4- to 6-membered monocyclic heterocyclyl (unsaturated, saturated or partially unsaturated) having 1-2 heteroatoms selected from O, S and N. Examples of a 4- to 6-membered monocyclic heterocyclic include, but are not limited to azetidinyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, dihydrofuranyl, imidazolinyl, dihydropyranyl, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, and tetrazinyl.

In another embodiment, a heterocyclyl is a saturated 4- to 6-membered monocyclic heterocyclyl having 1-2 heteroatoms selected from O, S and N. Examples of saturated 4- to 6-membered monocyclic heterocyclic ring systems include, but are not limited to azetidinyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, and dithiinyl. In one embodiment, a saturated 4- to 6-membered monocyclic heterocyclyl is azetidinyl, oxetanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, or dioxinyl. In another embodiment, a saturated 4- to 6-membered monocyclic heterocyclyl is oxetanyl, tetrahydrofuranyl, or tetrahydropyranyl.

In one embodiment, a 4- to 6-membered monocyclic heterocyclyl is selected from

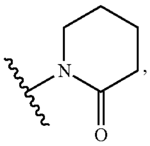,
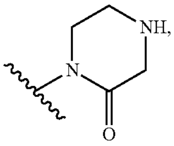,
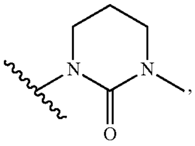,
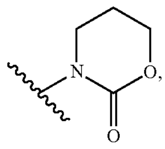,
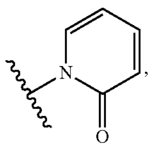, and
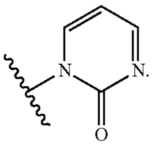.

In one embodiment, a heterocyclyl is a 7-membered monocyclic heterocyclyl (saturated or partially unsaturated), such as a 7-membered monocyclic heterocyclyl having one heteroatom selected from O and N. Examples of a 7-membered monocyclic heterocyclyl include, but are not limited to, azepanyl, azepinyl, oxepanyl, oxepinyl, thiepanyl, thiepinyl, diazepanyl, diazepinyl, and thiazepinyl.

In another embodiment, a heterocyclyl is a 7- to 10-membered bicyclic heterocyclyl. In yet another embodiment, a heterocyclyl is a 8- to 10-membered non-aromatic bicyclic heterocyclyl. In another embodiment, a heterocyclyl is 8- to 10-membered fused non-aromatic bicyclic heterocyclyl. The heterocyclyl group can be attached to the rest of a compound of the invention at a heteroatom or a carbon atom. In one embodiment, a 8- to 10-membered fused non-aromatic bicyclic heterocyclyl is selected from

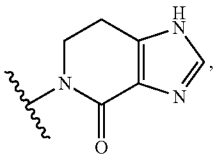,
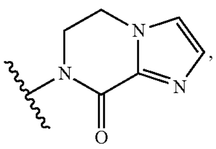,
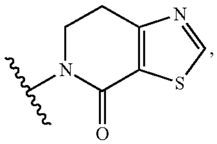,
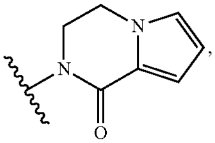,

-continued

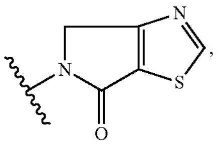
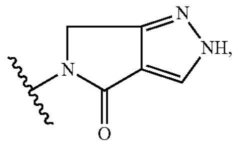
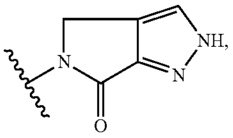
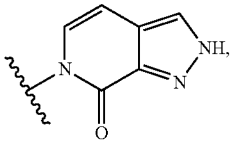
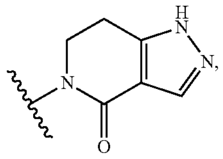
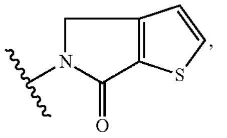
and
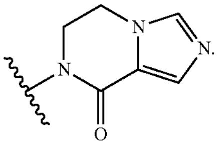

As used herein, the term "heteroaryl" refers to an aromatic 5- to 6-membered monocyclic or a 7- to 10-membered bicyclic ring system, having 1 to 4 heteroatoms independently selected from O, N and S, and wherein N can be oxidized (e.g., N(O)) or quaternized, and S can be optionally oxidized to sulfoxide and sulfone. Examples of 5- to 6-membered monocyclic heteroaryls include, but are not limited to, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, and the like. In one embodiment, a heteroaryl is a 5-membered heteroaryl. Examples of a 5-membered heteroaryl include, but are not limited to, pyrazolyl, oxazolyl, isoxazolyl, 1,2,3-oxadiazolyl, 1,3,4-oxadiazolyl, 1,2,4-oxadizolyl, 1,2,3-thiadiazolyl, 1,3,4-thiadiazolyl, 1,2,4-thiadiazolyl, 1,2,3-triazolyl, 1,2,4-triazolyl, and tetrazolyl. In one embodiment, a 5-membered heteroaryl is selected from

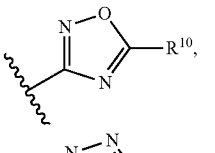
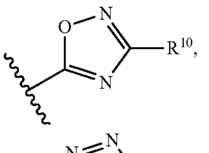
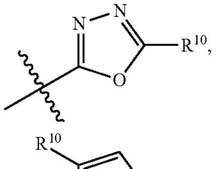
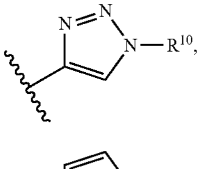
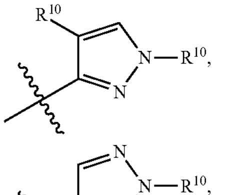
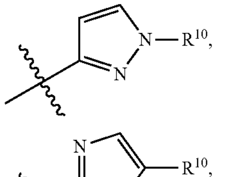
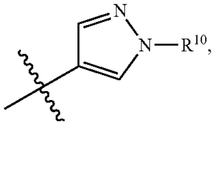
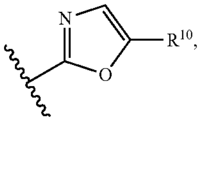

-continued

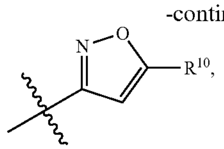
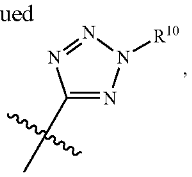
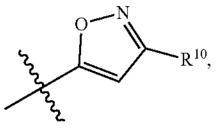
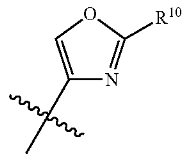
and
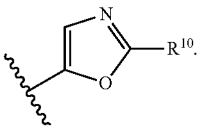

Examples of 8- to 10-membered bicyclic heteroaryls include, but are not limited to, dihydropyrrolopyrrolyl, indolyl, isoindolyl, benzimidazolyl, benzothiazolyl, quinolinyl, isoquinolinyl, quinazolinyl and purinyl.

In another embodiment, a heterocyclyl is a 4-8 membered monocyclic saturated azacyclic ring. Examples include azetidinyl, pyrrolidinyl, imidazolidinyl, pyrazolidinyl, oxazolidinyl, isoxazolidinyl, thiazolidinyl, isothiazolidinyl, piperidinyl, piperazinyl, morpholinyl, thiomorpholinyl, azepanyl, oxazepanyl, and imidazolinyl. In another embodiment, a heterocyclyl is a 4-7 membered monocyclic saturated azacyclic ring. Examples include azetidinyl, pyrrolidinyl, imidazolidinyl, pyrazolidinyl, oxazolidinyl, isoxazolidinyl, thiazolidinyl, isothiazolidinyl, piperidinyl, piperazinyl, morpholinyl, thiomorpholinyl, oxazepanyl and imidazolinyl.

The term "fused ring system", as used herein, is a ring system that has two rings each of which are independently selected from a carbocyclyl or a heterocyclyl, wherein the two ring structures share two adjacent ring atoms. In one embodiment, a fused ring system have from 9 to 12 ring members.

The term "bridged ring system", as used herein, is a ring system that has a carbocyclyl or heterocyclyl ring wherein two non-adjacent atoms of the ring are connected (bridged) by one or more (preferably from one to three) atoms selected from C, N, O, and S. In one embodiment, a bridged ring system have from 6 to 8 ring members.

The term "spiro ring system," as used herein, is a ring system that has two rings each of which are independently selected from a carbocyclyl or a heterocyclyl, wherein the two ring structures having one ring atom in common. In one embodiment, spiro ring systems have from 5 to 8 ring members.

As used herein, the term "carbocyclyl" refers to saturated or unsaturated monocyclic or bicyclic hydrocarbon groups of 3-7 carbon atoms, 3-5, 3-6, 3-8, 4-6, or 5-7 carbon atoms. The term "carbocyclyl" encompasses cycloalkyl groups and aromatic groups (i.e., aryl). The term "cycloalkyl" refers to completely saturated monocyclic or bicyclic or spiro hydrocarbon groups of 3-7 carbon atoms, 3-6 carbon atoms, or 5-7 carbon atoms. Exemplary bicyclic carbocyclyl groups include bicyclo[2.1.1]hexyl, bicyclo[2.2.1]heptyl, bicyclo[2.2.1]heptenyl, tricyclo[2.2.1.$0^{2,6}$]heptanyl, 6,6-dimethylbicyclo[3.1.1]heptyl, or 2,6,6-trimethylbicyclo[3.1.1]heptyl, spiro[2.2]pentanyl, and spiro[3.3]heptanyl.

In one embodiment, the carbocyclyl is a 3- to 7-membered (saturated or partially unsaturated) monocyclic carbocyclyl. Exemplary 3- to 7-membered (saturated or partially unsaturated) monocyclic carbocyclyls include, but are not limited to, cyclopropyl, cyclobutyl, cyclopentyl, cyclohexyl, cycloheptyl, cyclopropenyl, cyclobutenyl, cyclopenentyl, cyclohexenyl, cycloheptenyl, cyclobutadienyl, cyclopentadienyl, cyclohexadienyl, cycloheptadienyl, phenyl and cycloheptatrienyl. In one embodiment, the carbocyclyl is a 5- to 7-membered monocyclic carbocyclyl, such as but not limited to cyclopentyl, cyclohexyl, cycloheptyl, cyclopenentyl, cyclohexenyl, cycloheptenyl, cyclopentadienyl, cyclohexadienyl, cycloheptadienyl, phenyl or cycloheptatrienyl. In another embodiment, the carbocyclyl is a 4- to 6-membered monocyclic carbocyclyl, such as but not limited to cyclobutyl, cyclopentyl, cyclohexyl, cyclobutenyl, cyclopenentyl, cyclohexenyl, or phenyl. In another embodiment, the carbocyclyl is a 4- to 6-membered monocyclic carbocyclyl. In another embodiment, the carbocyclyl is a 3- to 6-membered carbocyclyl. In another embodiment, the carbocyclyl is a 3- to 6-membered cycloalkyl. In yet another embodiment, the carbocyclyl is phenyl. In yet another embodiment, the carbocyclyl is cyclopropyl.

In one embodiment, the carbocyclyl is a 7- to 10-membered bicyclic carbocyclyl. Exemplary 7- to 10-membered bicyclic carbocyclyls include, but are not limited to, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, spiro[3.3]heptanyl, bicyclo[3.3.0]octanyl, bicyclo[2.2.2]octanyl, bicyclo[3.3.1]nonanyl, bicyclo[3.3.2]decanyl, decalinyl and indanyl.

In cases where a compound provided herein is sufficiently basic or acidic to form stable nontoxic acid or base salts, preparation and administration of the compounds as pharmaceutically acceptable salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, or α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases, can include but are not limited to, sodium, potassium, lithium, ammonium, calcium or magnesium salts. Salts derived from organic bases can include, but are not limited to, salts of primary, secondary or tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocycloalkyl amines, diheterocycloalkyl amines, triheterocycloalkyl amines, or mixed di- and tri-amines where at least two of the substituents on the amine can be different and can be alkyl, substituted alkyl, alkenyl, substituted alkenyl, cycloalkyl, substituted cycloalkyl, cycloalkenyl, substituted cycloalkenyl, aryl, heteroaryl, or heterocycloalkyl and the like. Also included are amines where the two or three substituents, together with the amino nitrogen, form a heterocycloalkyl or heteroaryl group. Non-limiting examples of amines can include, isopropylamine, trimethyl amine, diethyl amine, tri(iso-propyl) amine, tri(n-propyl) amine, ethanolamine, 2-dimethylaminoethanol, trimethamine, lysine, arginine, histidine, caffeine, procaine, hydrabamine, choline, betaine, ethylenediamine, glucosamine, N-alkylglucamines, theobromine, purines, piperazine, piperidine, morpholine, or N-ethylpiperidine, and the like. Other carboxylic acid derivatives can be useful, for example, carboxylic acid amides, including carboxamides, lower alkyl carboxamides, or dialkyl carboxamides, and the like.

The compounds or pharmaceutically acceptable salts thereof as described herein, can contain one or more asymmetric centers in the molecule. In accordance with the present disclosure any structure that does not designate the stereochemistry is to be understood as embracing all the various stereoisomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optically-active starting materials, by chiral synthesis, or chromatographic separation using a chiral stationary phase).

When a particular stereoisomer of a compound is depicted by name or structure, the stereochemical purity of the compounds is at least 20%, 30%, 40%, 50%, 60%, 70%, 80%, 90%, 95%, 97%, 99%, 99.5% or 99.9%. "Stereochemical purity" means the weight percent of the desired stereoisomer relative to the combined weight of all stereoisomers.

When a particular enantiomer of a compound is depicted by name or structure, the stereochemical purity of the compounds is at least 20%, 30%, 40%, 50%, 60%, 70%, 80%, 90%, 95%, 97%, 99%, 99.5% or 99.9%. "Stereochemical purity" means the weight percent of the desired enantiomer relative to the combined weight of all stereoisomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 20%, 30%, 40%, 50%, 60%, 70%, 80%, 90%, 95%, 97%, 99%, 99.5% or 99.9%. The stereoisomeric purity the weight percent of the desired stereoisomers encompassed by the name or structure relative to the combined weight of all of the stereoisomers.

When a disclosed compound is named or depicted by structure without indicating the stereochemistry, and the compound has one chiral center, it is to be understood that the name or structure encompasses one enantiomer of compound in pure or substantially pure form, as well as mixtures thereof (such as a racemic mixture of the compound and mixtures enriched in one enantiomer relative to its corresponding optical isomer).

When a disclosed compound is named or depicted by structure without indicating the stereochemistry and, e.g., the compound has at least two chiral centers, it is to be understood that the name or structure encompasses one stereoisomer in pure or substantially pure form, as well as mixtures thereof (such as mixtures of stereoisomers, and mixtures of stereoisomers in which one or more stereoisomers is enriched relative to the other stereoisomer(s)).

The disclosed compounds may exist in tautomeric forms and mixtures and separate individual tautomers are contemplated. In addition, some compounds may exhibit polymorphism.

In one embodiment, the invention provides deuterated compounds disclosed herein, in which any or more positions occupied by hydrogen can include enrichment by deuterium above the natural abundance of deuterium. For example, one or more hydrogen atoms are replaced with deuterium at an abundance that is at least 3340 times greater than the natural abundance of deuterium, which is 0.015% (i.e., at least 50.1% incorporation of deuterium), at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). In one embodiment, hydrogen is present at all positions at its natural abundance. The compounds or pharmaceutically acceptable salts thereof as described herein, may exist in tautomeric forms and mixtures and separate individual tautomers are contemplated.

Another embodiment is a pharmaceutical composition comprising at least one compound described herein, or a pharmaceutically acceptable salt thereof, and at least one pharmaceutically acceptable carrier.

The compounds, or pharmaceutically acceptable salts thereof described herein may be used to decrease the activity of Btk, or to otherwise affect the properties and/or behavior of Btk, e.g., stability, phosphorylation, kinase activity, interactions with other proteins, etc.

In some embodiments, the present invention provides methods of decreasing Btk enzymatic activity. In some embodiments, such methods include contacting a Btk with an effective amount of a Btk inhibitor. Therefore, the present invention further provides methods of inhibiting Btk enzymatic activity by contacting a Btk with a Btk inhibitor of the present invention.

One embodiment of the invention includes a method of treating a disorder responsive to inhibition of Btk in a subject comprising administering to the subject an effective amount of at least one compound described herein, or a pharmaceutically acceptable salt thereof, or a pharmaceutical composition described herein.

In one embodiment, the present invention provides methods of treating autoimmune disorders, inflammatory disorders, and cancers in a subject in need thereof comprising administering to the subject an effective amount of at least one compound described herein, or a pharmaceutically acceptable salt thereof, or a pharmaceutical composition described herein.

The term "autoimmune disorders" includes diseases or disorders involving inappropriate immune response against native antigens, such as acute disseminated encephalomyelitis (ADEM), Addison's disease, alopecia areata, antiphospholipid antibody syndrome (APS), autoimmune hemolytic anemia, autoimmune hepatitis, bullous pemphigoid (BP), Coeliac disease, dermatomyositis, diabetes mellitus type 1, Goodpasture's syndrome, Graves' disease, Guillain-Barre syndrome (GBS), Hashimoto's disease, idiopathic thrombocytopenic purpura, lupus erythematosus, mixed connective tissue disease, multiple sclerosis, myasthenia gravis, pemphigus vulgaris, pernicious anaemia, polymyositis, primary biliary cirrhosis, Sjogren's syndrome, temporal arteritis, and Wegener's granulomatosis. The term "inflammatory disorders" includes diseases or disorders involving acute or chronic inflammation such as allergies, asthma, atopic dermatitis, prostatitis, glomerulonephritis, pelvic inflammatory disease (PID), inflammatory bowel disease (IBD, e.g., Crohn's disease, ulcerative colitis), reperfusion injury, rheumatoid arthritis, transplant rejection, and vasculitis. In some embodiments, the present invention provides a method of treating rheumatoid arthritis. In some embodiments, the present invention provides a method of treating multiple sclerosis. In some embodiments, the present invention provides a method of treating systemic lupus erythematosus. In some embodiments, the present invention provides a method of treating atopic dermatitis.

The term "cancer" includes diseases or disorders involving abnormal cell growth and/or proliferation, such as glioma, thyroid carcinoma, breast carcinoma, lung cancer (e.g. small-cell lung carcinoma, non-small-cell lung carcinoma), gastric carcinoma, gastrointestinal stromal tumors, pancreatic carcinoma, bile duct carcinoma, ovarian carcinoma, endometrial carcinoma, prostate carcinoma, renal cell carcinoma, lymphoma (e.g., anaplastic large-cell lymphoma), leukemia (e.g. acute myeloid leukemia, T-cell leukemia, chronic lymphocytic leukemia), multiple myeloma, malignant mesothelioma, malignant melanoma, and colon cancer (e.g. microsatellite instability-high colorectal cancer). In some embodiments, the present invention provides a method of treating leukemia or lymphoma.

As used herein, the term "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

As used herein, the term "treating" or "treatment" refers to obtaining desired pharmacological and/or physiological effect. The effect can be therapeutic, which includes achieving, partially or substantially, one or more of the following results: partially or totally reducing the extent of the disease, disorder or syndrome; ameliorating or improving a clinical symptom or indicator associated with the disorder; or delaying, inhibiting or decreasing the likelihood of the progression of the disease, disorder or syndrome.

The effective dose of a compound provided herein, or a pharmaceutically acceptable salt thereof, administered to a subject can be 10 μg-500 mg.

Administering a compound described herein, or a pharmaceutically acceptable salt thereof, to a mammal comprises any suitable delivery method. Administering a compound described herein, or a pharmaceutically acceptable salt thereof, to a mammal includes administering a compound described herein, or a pharmaceutically acceptable salt thereof, topically, enterally, parenterally, transdermally, transmucosally, via inhalation, intracisternally, epidurally, intravaginally, intravenously, intramuscularly, subcutaneously, intradermally or intravitreally to the mammal. Administering a compound described herein, or a pharmaceutically acceptable salt thereof, to a mammal also includes administering topically, enterally, parenterally, transdermally, transmucosally, via inhalation, intracisternally, epidurally, intravaginally, intravenously, intramuscularly, subcutaneously, intradermally or intravitreally to a mammal a compound that metabolizes within or on a surface of the body of the mammal to a compound described herein, or a pharmaceutically acceptable salt thereof.

Thus, a compound or pharmaceutically acceptable salt thereof as described herein, may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the compound or pharmaceutically acceptable salt thereof as described herein may be combined with one or more excipients and used in the form of ingestible tablets, buccal tablets, troches, capsules, elixirs, suspensions, syrups, or wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions can be such that an effective dosage level will be obtained.

The tablets, troches, pills, capsules, and the like can include the following: binders such as gum tragacanth, acacia, corn starch or gelatin; excipients such as dicalcium phosphate; a disintegrating agent such as corn starch, potato starch, alginic acid and the like; a lubricant such as magnesium stearate; or a sweetening agent such as sucrose, fructose, lactose or aspartame or a flavoring agent.

The active compound may also be administered intravenously or intraperitoneally by infusion or injection. Solutions of the active compound or its salts can be prepared in water, optionally mixed with a nontoxic surfactant.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions. In all cases, the ultimate dosage form should be sterile, fluid and stable under the conditions of manufacture and storage.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation can be vacuum drying and the freeze drying techniques, which can yield a powder of the active ingredient plus any additional desired ingredient present in the previously sterile-filtered solutions.

Exemplary solid carriers can include finely divided solids such as talc, clay, microcrystalline cellulose, silica, alumina and the like. Useful liquid carriers include water, alcohols or glycols or water-alcohol/glycol blends, in which the compounds or pharmaceutically acceptable salts thereof as described herein can be dissolved or dispersed at effective levels, optionally with the aid of non-toxic surfactants.

Useful dosages of a compound or pharmaceutically acceptable salt thereof as described herein can be determined by comparing their in vitro activity, and in vivo activity in animal models. Methods for the extrapolation of effective dosages in mice, and other animals, to humans are known to the art; for example, see U.S. Pat. No. 4,938,949, which is incorporated by reference in its entirety.

The amount of a compound or pharmaceutically acceptable salt thereof as described herein, required for use in treatment can vary not only with the particular salt selected but also with the route of administration, the nature of the condition being treated and the age and condition of the patient and can be ultimately at the discretion of the attendant physician or clinician. In general, however, a dose can be in the range of from about 0.1 to about 10 mg/kg of body weight per day.

The a compound or pharmaceutically acceptable salt thereof as described herein can be conveniently administered in unit dosage form; for example, containing 0.01 to 10 mg, or 0.05 to 1 mg, of active ingredient per unit dosage form. In some embodiments, a dose of 5 mg/kg or less can be suitable.

The desired dose may conveniently be presented in a single dose or as divided doses administered at appropriate intervals.

The disclosed method can include a kit comprising a compound or pharmaceutically acceptable salt thereof as described herein and instructional material which can describe administering a compound or pharmaceutically acceptable salt thereof as described herein or a composition comprising a compound or pharmaceutically acceptable salt thereof as described herein to a cell or a subject. This should be construed to include other embodiments of kits that are known to those skilled in the art, such as a kit comprising a (such as sterile) solvent for dissolving or suspending a compound or pharmaceutically acceptable salt thereof as described herein or composition prior to administering a compound or pharmaceutically acceptable salt thereof as described herein or composition to a cell or a subject. In some embodiments, the subject can be a human.

EXEMPLIFICATIONS

Abbreviations and acronyms used herein include the following:

AcOH means acetic acid;
Aq. means aqueous;
Ar means argon;
Bn means benzyl;
Boc means tert-butoxy carbonyl;
$Boc_2O$ means di-tert-butyl dicarbonate;
$(BPin)_2$ means bis(pinacolato)diboron;
br means broad;
n-BuOH means n-butanol;
t-BuOH means tert-butanol;
n-BuLi means n-butyl lithium;
° C. means degrees Celsius;
$CCl_4$ means carbon tetrachloride;
$CHCl_3$ means chloroform;
$CDCl_3$ means deutero-chloroform;
CDI means 1,1'-carbonyldiimidazole;
CO means carbon monoxide;
$CO_2$ means carbon dioxide;
$Cs_2CO_3$ means cesium carbonate;
CuBr means copper bromide;
CuCN means copper cyanide;
CuI means copper iodide;
δ means chemical shift;
d means doublet;
dd means double doublet;
DCM means dichloromethane;
DAST means (diethylamino)sulfur trichloride;

DIPEA means N-ethyldiisopropylamine or N,N-diisopropylethylamine;
DEA means diethylamine;
DIAD means diisopropyl azodiformate;
DMAP means 4-(dimethlamino)pyridine;
DMF means N,N-dimethylformamide;
DMSO means dimethylsulfoxide;
DMSO-$d_6$ means hexadeuterodimethyl sulfoxide;
$D_2O$ means deuterated water;
EDC means N-(3-dimethylaminopropyl)-N'-ethylcarbodiimide hydrochloride;
Et means ethyl;
$Et_2O$ means ether;
EtOH means ethanol;
EtOAc means ethyl acetate;
Eq. means equivalent;
g means gram;
HATU means N-[(dimethylamino)-1H-1,2,3-triazolo-[4,5-b]pyridin-1-ylmethylene]-N-methylmethanaminium hexafluorophosphate N-oxide;
HBr means hydrogen bromide;
HCl means hydrochloric acid;
$HCO_2H$ means formic acid;
Hept means heptanes;
$^1H$ NMR means proton nuclear magnetic resonance;
$H_2O$ means water;
HPLC means high pressure liquid chromatography;
h means hour;
IPA means isopropyl alcohol;
$K_2CO_3$ means potassium carbonate;
KF means potassium fluoride;
KI means potassium iodide;
KOAc means potassium acetate;
KOtBu means potassium tert-butoxide;
KOH means potassium hydroxide;
$K_3PO_4$ means potassium phosphate tribasic;
L means liter;
LCMS means liquid chromatography mass spectrometry;
LiOH means lithium hydroxide;
m means multiplet;
M means molar;
Me means methyl;
MeCN means acetonitrile;
Mel means methyl iodide;
MeOH means methanol;
MeOH-$d_4$ means deutero-methanol;
mg means milligram;
$MgSO_4$ means magnesium sulfate;
MHz means mega Hertz;
mins means minutes;
mL means milliliters;
mmol means millimole;
$MnO_2$ means manganese (IV) oxide;
MS m/z means mass spectrum peak;
MV means Mass volume ratio;
$N_2$ means nitrogen;
$Na_2CO_3$ means sodium carbonate;
NaH means sodium hydride;
$NaHCO_3$ means sodium bicarbonate;
NaI means sodium iodide;
NaOH means sodium hydroxide;
NaOtBu means sodium tert-butoxide;
$Na_2SO_3$ means sodium thiosulfate;
$Na_2SO_4$ means sodium sulfate;
NBS means N-bromosuccinimide;
$NH_3$ means ammonia;
$NH_4Cl$ means ammonium chloride;
$NH_4HCO_3$ means ammonium bicarbonate;
$NH_4OH$ is ammonium hydroxide;
Pd/C means palladium on carbon;
Pd(t-$Bu_3$P)$_2$ means bis(tri-tert-butylphosphine)palladium (O);
P(t-Bu)$_3$Pd G2 means chloro[(tri-tert-butylphosphine)-2-(2-aminobiphenyl)] palladium(II);
Pd(OAc)$_2$ means palladium acetate;
$Pd_2$(dba)$_3$ means tris(dibenzylideneacetone)dipalladium (0);
Pd(dppf)$Cl_2$ means [1,1'-bis(diphenylphosphino)ferrocene]dichloropalladium(II);
Pd(dppf)$Cl_2$•DCM means [1,1'-bis(diphenylphosphino) ferrocene]dichloropalladium(II), complex with dichloromethane;
Pd(dtbpf)$Cl_2$ means [1,1'-bis(di-tert-butylphosphino)ferrocene]dichloropalladium(II);
Pd(PPh$_3$)$_4$ means tetrakis(triphenylphosphine)palladium (0);
PE means petroleum ether;
$POCl_3$ means phosphoryl chloride;
i-PrOH means isopropanol;
$PPh_3$ means triphenylphosphine;
PyBroP means bromotripyrrolidinophosphonium hexafluorophosphate;
q means quartet;
Rt means retention time;
rt means room temperature;
RuPhos means 2-dicyclohexylphosphino-2',6'-diisopropoxybiphenyl;
RuPhos Pd G3 means (2-dicyclohexylphosphino-2',6'-diisopropoxy-1,1'-biphenyl)[2-(2'-amino-1,1'-biphenyl)]palladium(II) methanesulfonate;
s means singlet;
sat. means saturated;
SCX means strong cation exchange;
SFC means supercritical fluid chromatography;
$SiO_2$ means silicon dioxide;
$SOCl_2$ means thionyl chloride;
soln. means solution;
t means triplet;
TBDMS means tert-butyldimethylsilyl;
TBME means tert-butyl methyl ether;
TEA means triethylamine;
TFA means trifluoroacetic acid;
THF means tetrahydrofuran;
TLC means thin layer chromatography;
TMOS means tetramethyl orthosilicate;
TMS means trimethylsilyl;
T3P means 2,4,6-tripropyl-1,3,5,2,4,6-trioxatriphosphorinane-2,4,6-trioxide;
TTBP means tri-tert-butylphosphonium tetrafluoroborate;
μL means micro liters;
μmol means micromole;

Synthesis of Compounds of Formulas (I), (II), (III), (IIA), (IIIA), (IV), and (V)

General Synthetic Procedures

Compounds of Formulas (I), (II), (III), (IIA), (IIIA), (IV), and (V) or pharmaceutically acceptable salts thereof may be prepared using the general procedures described in Methods A, B, and C and illustrated in Scheme 1, Scheme 2, and Scheme 3 below.

Method A According to Method A, compounds of Formula (I) may be prepared from compounds of Formulae (a), (b), (c), (d), (e), (f), (g), and (h) as illustrated in Scheme 1.

In this scheme, PG is an NH protecting group, typically a carbamate and preferably Boc or Cbz; LG is a leaving group, preferably Br, Cl or OTf; and Z is Cl, OH, $O^- K^+$, or $O^- Li^+$.

The compound of Formula (c) may be prepared according to step (i) through an amide bond formation by reacting the compound of Formula (b) with the compound of Formula (a) having an amine in the presence of a suitable coupling agent and organic base in a suitable polar aprotic solvent. When Z is OH, $O^- K^+$, or $O^- Li^+$, preferred conditions include reaction of the compound of Formula (b) with the amine on the compound of Formula (a) in the presence of a coupling agent, preferably T3P® or HATU, in the presence of a suitable organic base such as TEA or DIPEA, and in a suitable solvent, such as DMF, DCM or THF, at between room temperature (RT) and 45° C.

Scheme 1

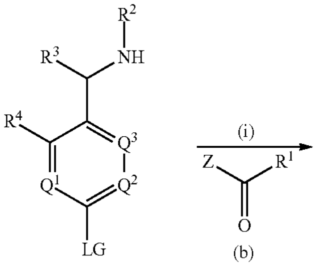

(a) (b)

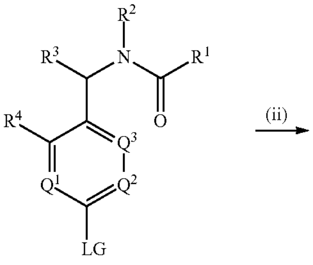

(c)

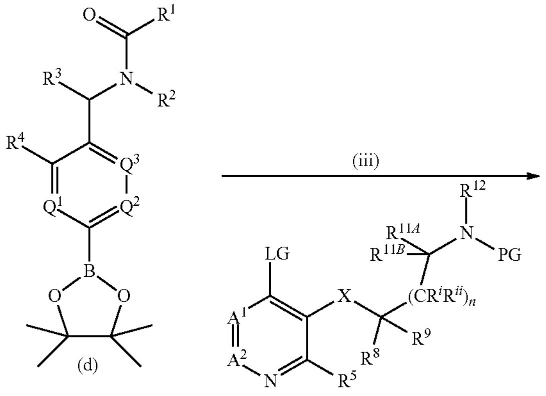

(d) (e)

-continued

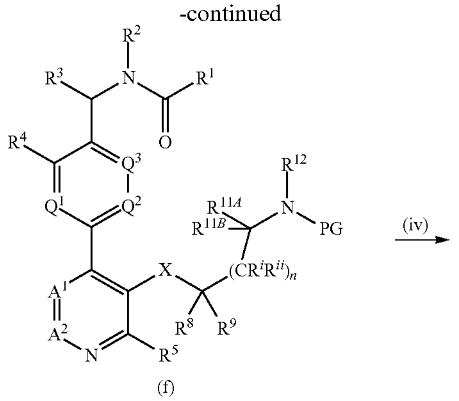

(f)

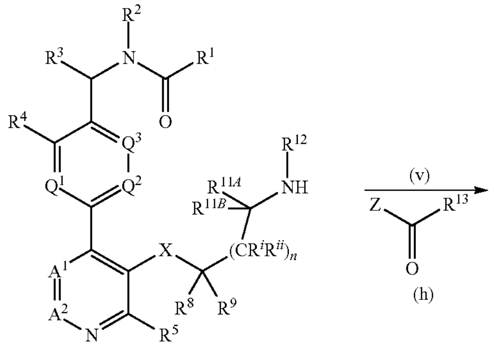

(h)

(g)

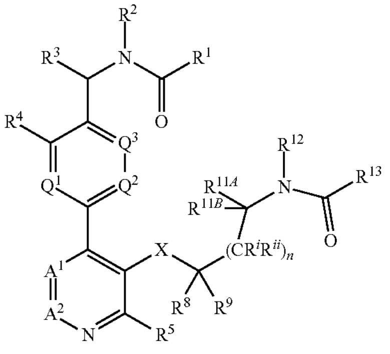

(I)

Alternatively, the compound of Formula (c) may be prepared from reacting the acid chloride of the compound of Formula (b) with the amine of Formula (a) in the presence of a suitable organic base in a suitable solvent. Preferred conditions include reaction of the amine of Formula (a) with the acid chloride of Formula (b) in the presence of DIPEA in DCM at RT.

The compound of Formula (d) may be prepared from the compound of Formula (c), according to step (ii), i.e., a boronate ester formation step using a suitable boronate such as $(BPin)_2$ in the presence of a suitable inorganic base, such as $K_2CO_3$ or KOAc, and a suitable catalyst, such as Pd(dppf)$Cl_2$ or $Pd_2(dba)_3$, with a suitable phosphine ligand, such as $P(cy)_3$ or XPhos or $Pd(PPh_3)_4$, in a suitable non-polar solvent at between RT and elevated temperature. Preferred conditions include treating the compound of Formula (c) with $(BPin)_2$ in the presence of Pd(dppf)$Cl_2$ or $Pd_2(dba)_3$ with XPhos or $P(cy)_3$ in the presence of KOAc in DMSO, toluene or dioxane at between 85° C. and 90° C.

The compound of Formula (f) may be prepared from the compound of Formula (d) and the compound of Formula (e)

(i.e., a heterocycle) according to step (iii), which is an organometallic catalysed cross-coupling reaction. Typical cross-coupling conditions include a palladium catalyst containing suitable phosphine ligands, in the presence of an inorganic or organic base, in aqueous solvent at between RT and the reflux temperature of the reaction. Preferred conditions include reaction of the compounds of Formulae (d) and (e) in the presence of $Pd(dppf)Cl_2$ or $Pd(dtbpf)Cl_2$ and a suitable base such as $Na_2CO_3$, $K_2CO_3$ or $K_3PO_4$ in a suitable solvent such as aqueous dioxane at between 70° C. and 100° C.

The compound of Formula (g) (i.e., an amine) may be prepared by the deprotection of the compound of Formula (f) according to process step (iv). Typically the compound of Formula (f) is treated with a suitable acid such as HCl or TFA in a suitable aprotic solvent such as DCM, MeOH, EtOAc or dioxane at between RT and reflux temperature. Preferred conditions include reaction of the compound of Formula (f) with TFA or HCl in DCM, MeOH, EtOAc or dioxane at between RT and 50° C.

The compound of Formula (I) may be prepared by an amide bond formation by reacting the compound of Formula (h) with the amine on the compound of Formula (g) in the presence of a suitable coupling agent and organic base in a suitable polar aprotic solvent.

When Z is OH, $O^- K^+$, or $O^- Li^+$, the preferred conditions include reaction of the compound of Formula (h) with the amine on the compound of Formula (g) in the presence of a coupling agent, preferably, T3P® or HATU, in the presence of a suitable organic base such as TEA or DIPEA, in a suitable solvent, such as DMF, DCM or THF, at between RT and 45° C.

Alternatively, the compound of Formula (I) may be prepared by reacting the acid chloride of the compound of Formula (h) with the amine on the compound of Formula (g) in the presence of a suitable organic base in a suitable solvent. Preferred conditions include reaction of the amine on the compound of Formula (g) with the acid chloride of the compound of Formula (h) in the presence of DIPEA in DCM at RT.

Method B

According to Method B, compounds of Formula (I) may be prepared from compounds of Formulae (m), (n), (b), and (d) illustrated by Scheme 2.

Scheme 2

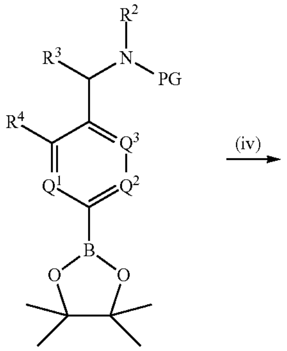

(m)

-continued

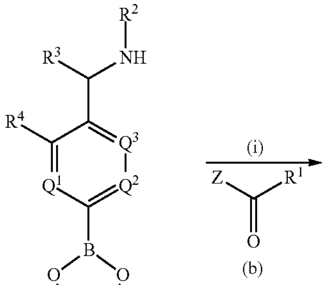

(n)

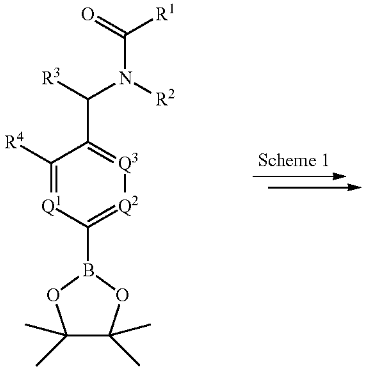

(d)

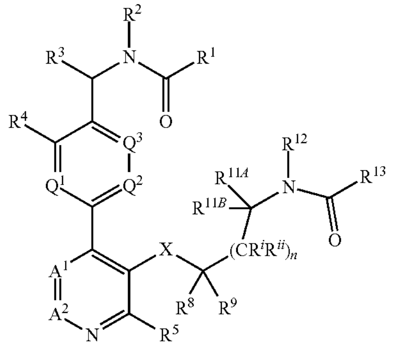

(I)

The compound of Formula (n) may be prepared from the compound of Formula (m) (i.e., a protected amine) according to step (iv), which is a deprotection reaction as described previously in Scheme 1.

The compound of Formula (d) may be prepared from the compound of Formula (n) and the compound of Formula (b) according to step (i), which is an amide bond formation as previously described in Scheme 1. Preferred conditions include reaction of the acid of the compound of Formula (b) with the compound of Formula (n) in the presence of a coupling agent, preferably T3P®, HBTU or HATU, in the presence of a suitable organic base such as DIPEA or pyridine, optionally in a suitable solvent such as DMF at between RT and 50° C.

The compound of Formula (I) may be prepared according to steps (iii), (iv), and (v), an organometallic catalysed cross-coupling reaction coupling reaction, an amine deprotection reaction, and an amide bond formation, respectively, as previously described in Scheme 1.

Method C
According to Method C, compounds of Formula (I), wherein $R^5$ is a hydrogen, may be prepared from compounds of Formulae (m), (o), (p), (q), (r), (s), (t), (u), (v), (b), (g), and (h) as illustrated by Scheme 3.
Scheme 3
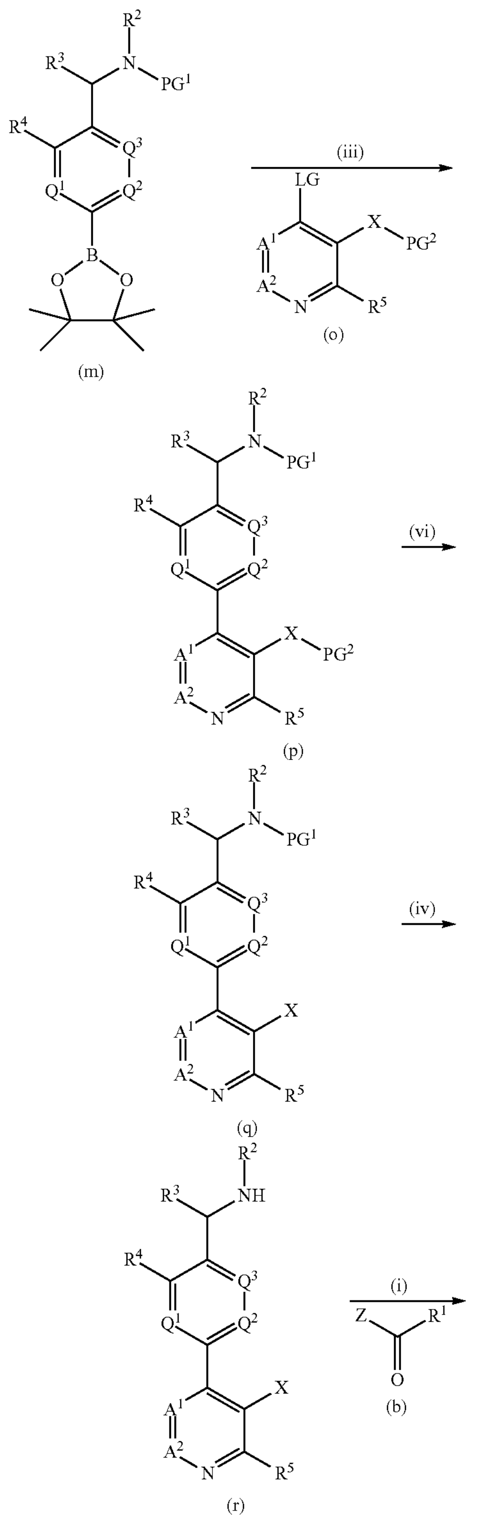
-continued
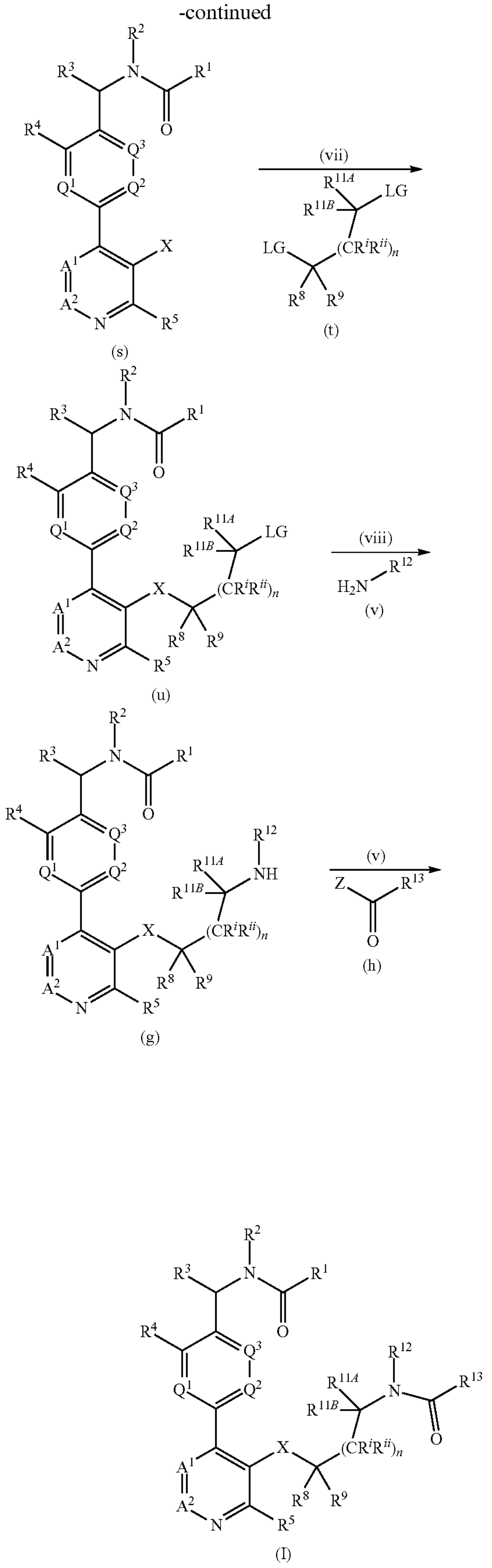

The compound of Formula (p) may be prepared from the compounds of Formulae (m) and (o), according to step (iii), i.e., an organometallic catalysed cross-coupling reaction as previously described in Scheme 1.

The compound of Formula (q) may be prepared from the deprotection of compound of Formula (p) according to step (vi). Typical deprotection conditions include treating compound of Formula (p) with thiolate salts, Lewis acids, strong acids, or strong bases in a suitable polar, aprotic solvent between RT and reflux. Preferred conditions include reaction of the compound of Formula (p) with sodium methyl thiolate in a suitable solvent such as DMF at an elevated temperature between RT and 100° C.

The compound of Formula (r) may be prepared by the deprotection of the compound of Formula (q) according to step (iv) as previously described in Scheme 1.

The compound of Formula (s) may be prepared by from the compounds of Formulae (r) and (b) according to step (i), i.e., an amide bond formation as previously described in Scheme 1.

The compound of Formula (u) may be prepared from the compounds of Formulae (s) and (t) according to step (vii), an alkylation reaction. Typical alkylation conditions include an alkylating agent, in the presence of an inorganic base in a suitable polar aprotic solvent. Preferred conditions include reaction of the compounds of Formulae (s) and (t) in the presence of a suitable base, such as $Na_2CO_3$, $K_2CO_3$, or NaH in a suitable solvent such as DMF, DCM, or THF.

The compound of Formula (g) may be prepared from the compounds of Formulae (u) and (v) according to step (viii), i.e., a nucleophilic displacement reaction in the presence of an organic base (if necessary) in a suitable solvent (if necessary). Preferred conditions include reaction of the compounds of Formulae (u) and (v) neat between RT and 70° C.

The compound of Formula (I) may be prepared from the compounds of Formulae (g) and (h) according to step (v), i.e., an amide bond formation as previously described in Scheme 1.

The compounds of Formulae (a), (b), (h), (o), (t), and (v) are commercially available, may be prepared by analogy to methods known in the literature, or the methods described in the Experimental section below.

In addition, the skilled person will appreciate that it may be necessary or desirable at any stage in the synthesis of compounds of the invention to protect one or more sensitive groups, so as to prevent undesirable side reactions. In particular, it may be necessary or desirable to protect amino or carboxylic acid groups. The protecting groups used in the preparation of the compounds of the invention may be used in a conventional manner. See, for example, those described in 'Greene's Protective Groups in Organic Synthesis' by Theodora W. Greene and Peter G. M. Wuts, Fifth Edition, (John Wiley and Sons, 2014), in particular Chapter 7 ("Protection for the amino group") and Chapter 5 ("Protection for the Carboxyl group"), each incorporated herein by reference in its entirety, which also describes methods for the removal of such groups.

Example 1. Synthesis of N-(4-(6-amino-5-(2-(N-methylacrylamido)ethoxy)pyrimidin-4-yl)-2-methylbenzyl)-5-(tert-butyl)-1,3,4-oxadiazole-2-carboxamide (compound 1)

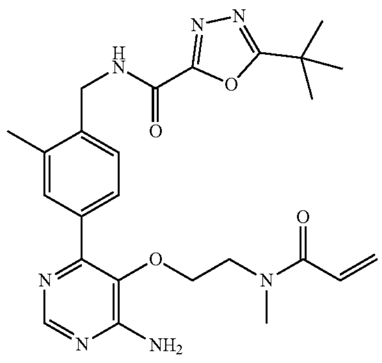 [SMILES: C=CC(=O)N(C)CCOc1c(N)ncnc1-c1ccc(CNC(=O)c2nnc(C(C)(C)C)o2)c(C)c1]

1. Preparation of N-(4-bromo-2-methylbenzyl)-5-(tert-butyl)-1,3,4-oxadiazole-2-carboxamide

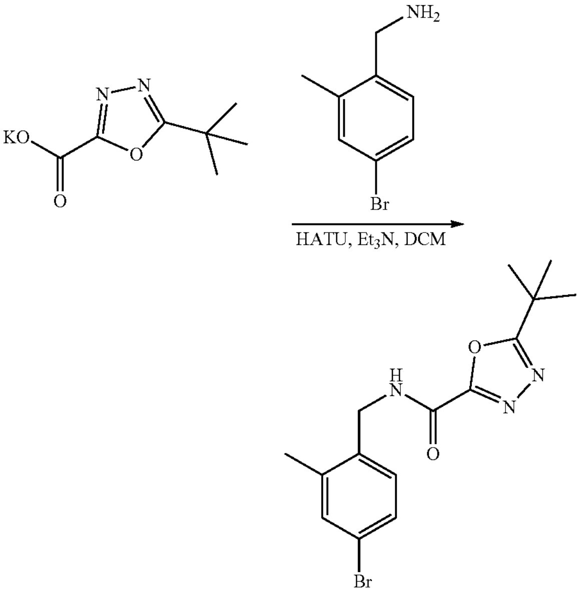

To a solution of potassium 5-(tert-butyl)-1,3,4-oxadiazole-2-carboxylate (4.06 g, 19.5 mmol) in DCM (40 mL) was added HATU (8.55 g, 22.5 mmol) and $Et_3N$ (3.03 g, 30.0 mmol, 4.17 mL). The mixture was stirred 20° C. for 0.5 h before the reaction mixture was cooled to 0° C. and (4-bromo-2-methylphenyl)methanamine (3.0 g, 15.0 mmol) was added. The reaction mixture was stirred for 10 min at 0° C. before warming the mixture to 20° C. stirring at that temperature for 12 h. Water (30 mL), followed by DCM (30 mL). The layers were separated and the aqueous phase was extracted with an additional portion of DCM (30 mL). The combined organic extracts were dried ($Na_2SO_4$), filtered, concentrated in vacuo. The residue was purified by silica gel column chromatography (petroleum ether/EtOAc, grading from 20:1 to 3:1) to give N-(4-bromo-2-methylbenzyl)-5-

(tert-butyl)-1,3,4-oxadiazole-2-carboxamide as a white solid (2.6 g, yield: 49%). $^1$H NMR: (400 MHz $CDCl_3$-d) δ: 7.31-7.22 (m, 3H), 7.12-7.07 (m, 1H), 4.55-4.50 (m, 2H), 2.30-2.26 (m, 3H), 1.41-1.39 (m, 9H).

2. Preparation of 5-(tert-butyl)-N-(2-methyl-4-(4,4,5,5-tetramethyl-1,3,2-dioxaborolan-2-yl)benzyl)-1,3,4-oxadiazole-2-carboxamide

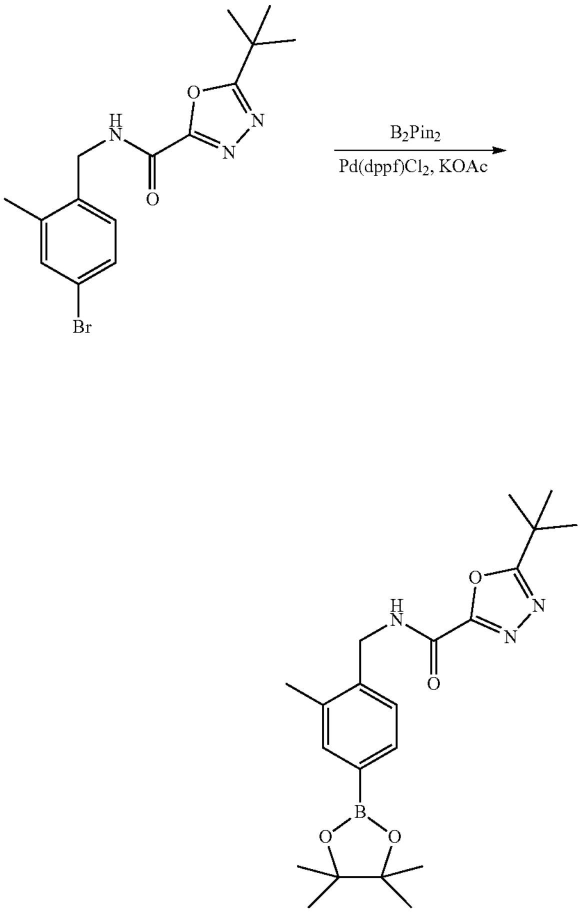

To a solution of N-(4-bromo-2-methylbenzyl)-5-(tert-butyl)-1,3,4-oxadiazole-2-carboxamide (2.5 g, 7.10 mmol) and (bispinacolato)diboron (2.7 g, 10.7 mmol) in dioxane (30 mL) was added KOAc (2.1 g, 21.3 mmol). The suspension was degassed under vacuum and purged with $N_2$ several times. Then, Pd(dppf)$Cl_2$ (519 mg, 0.71 mmol) was added to the mixture under $N_2$ and the reaction was warmed to 90° C. and was stirred at that temperature for 4 h. To the mixture was added water (20 mL) and EtOAc (20 mL). The layers were separated and the aqueous phase was extracted with an additional portion of EtOAc (20 mL). The combined organic layers were dried ($Na_2SO_4$), filtered, and concentrated in vacuo. The residue was purified by silica gel column chromatography (petroleum ether:EtOAc, grading from 5:1 to 1:1) to give 5-(tert-butyl)-N-(2-methyl-4-(4,4,5,5-tetramethyl-1,3,2-dioxaborolan-2-yl)benzyl)-1,3,4-oxadiazole-2-carboxamide as a gray solid (2.4 g, yield: 85%). ESI-MS $(M+H)^+$: 274.1.

3. Preparation of tert-butyl (2-((4-amino-6-(4-((5-(tert-butyl)-1,3,4-oxadiazole-2-carboxamido)methyl)-3-methylphenyl)pyrimidin-5-yl)oxy)ethyl)(methyl)carbamate

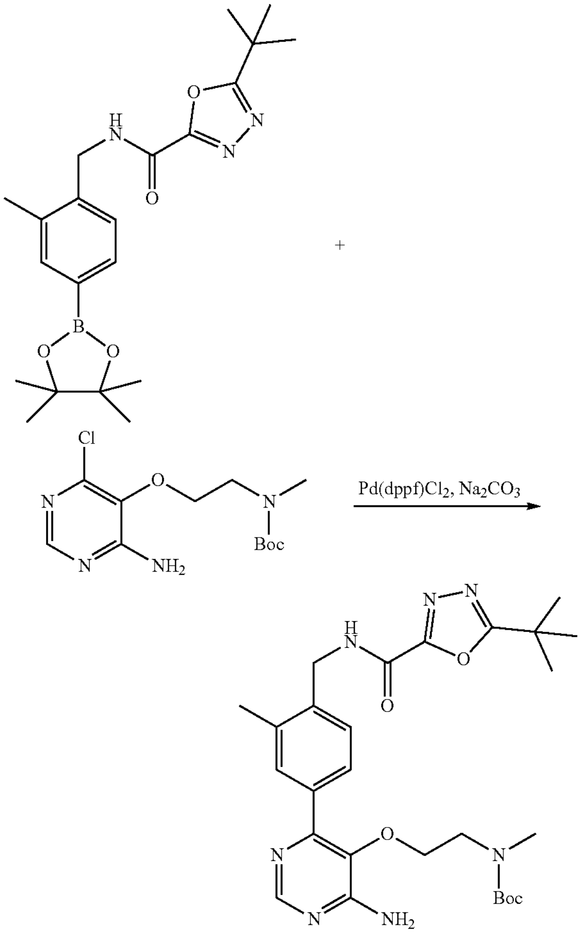

To a solution of tert-butyl (2-((4-amino-6-chloropyrimidin-5-yl)oxy)ethyl)(methyl)-carbamate (730 mg, 2.41 mmol) and 5-(tert-butyl)-N-(2-methyl-4-(4,4,5,5-tetramethyl-1,3,2-dioxaborolan-2-yl)benzyl)-1,3,4-oxadiazole-2-carboxamide (1 g, 2.50 mmol) in DMF (10 mL) was added $Na_2CO_3$ (1 M, 4.80 mL). The mixture was stirred at 20° C. for 6 min under $N_2$ and Pd(dppf)$Cl_2$ (180 mg, 0.25 mmol) was added. The reaction was heated to 100° C. and stirred at that temperature for 4 h. The mixture was poured into ice-water (w/w=1:1, 50 mL) and was stirred for 5 min. The aqueous phase was extracted with EtOAc (50 mL×3). The combined organic phases were washed with brine (50 mL×3), dried ($Na_2SO_4$), filtered, and concentrated in vacuo. The crude product was purified by silica gel column chromatography (petroleum ether/EtOAc, grading from 1:0 to 3:5) to give tert-butyl (2-((4-amino-6-(4-((5-(tert-butyl)-1,3,4-oxadiazole-2-carboxamido)methyl)-3-methylphenyl)pyrimidin-5-yl)oxy)ethyl)(methyl)-carbamate as a gray solid (0.7 g, crude). ESI-MS $(M+H)^+$: 540.3. $^1$H NMR: (400 MHz $CDCl_3$-d) δ: 8.45-8.32 (m, 1H), 7.88-7.74 (m, 2H), 7.39 (d, J=8.0 Hz, 1H), 4.71 (d, J=5.6 Hz, 2H), 3.75-3.65 (m, 2H), 3.48 (s, 2H), 2.90 (s, 3H), 2.45 (s, 3H), 1.51-1.38 (m, 18H).

4. Preparation of N-(4-(6-amino-5-(2-(methylamino)ethoxy)pyrimidin-4-yl)-2-methylbenzyl)-5-(tert-butyl)-1,3,4-oxadiazole-2-carboxamide

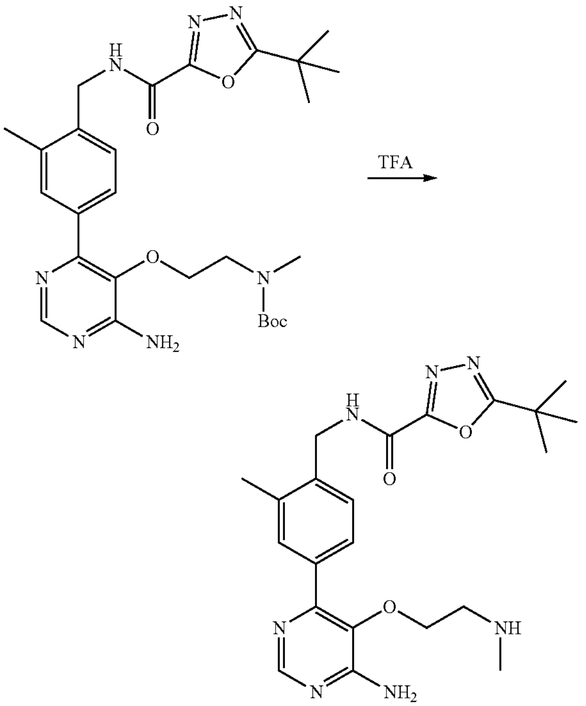

To a solution of tert-butyl (2-((4-amino-6-(4-((5-(tert-butyl)-1,3,4-oxadiazole-2-carboxamido)methyl)-3-methylphenyl)pyrimidin-5-yl)oxy)ethyl)(methyl)carbamate (500 mg, 0.93 mmol) in DCM (5 mL) was added TFA (1.58 g, 13.9 mmol, 1.03 mL), and the mixture was stirred at 20° C. for 12 h. The mixture was concentrated in vacuo to give N-(4-(6-amino-5-(2-(methylamino)ethoxy)pyrimidin-4-yl)-2-methylbenzyl)-5-(tert-butyl)-1,3,4-oxadiazole-2-carboxamide as a yellow oil (450 mg, crude). ESI-MS $(M+H)^+$: 440.3.

5. Preparation of N-(4-(6-amino-5-(2-(N-methylacrylamido)ethoxy)pyrimidin-4-yl)-2-methylbenzyl)-5-(tert-butyl)-1,3,4-oxadiazole-2-carboxamide (compound 1)

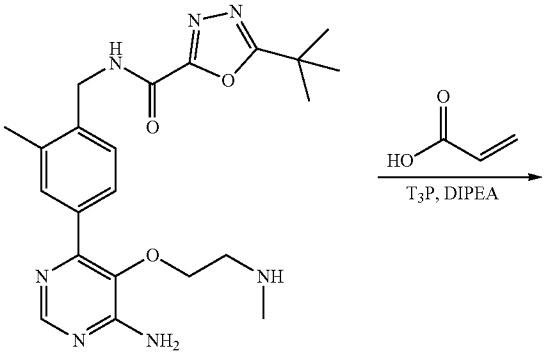

-continued

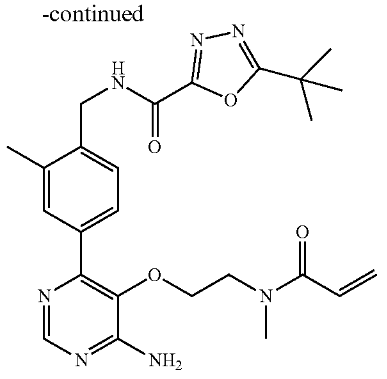

1

To a solution of acrylic acid (110 mg, 1.54 mmol, 105 μL) in DMF (1 mL) was added DIPEA (396 mg, 3.07 mmol, 0.5 mL) and $T_3P$ (423 mg, 1.33 mmol, 0.4 mL). The mixture was stirred at 15° C. for 30 min. To a solution of N-(4-(6-amino-5-(2-(methylamino)ethoxy)-pyrimidin-4-yl)-2-methylbenzyl)-5-(tert-butyl)-1,3,4-oxadiazole-2-carboxamide (450 mg, 1.02 mmol) in DMF (1 mL) at 0° C. was added DIPEA (396 mg, 3.07 mmol, 0.5 mL), followed by the dropwise addition of the previously prepared DMF solution. The reaction mixture was stirred at 0° C. for 30 min. Water (5 mL) was added, followed by EtOAc (5 mL). The layers were separated and the aqueous phase was extracted with EtOAc (5 mL×3). The combined organic extracts were dried ($Na_2SO_4$), filtered, and concentrated in vacuo. The residue was purified by prep-HPLC (column: Phenomenex Luna C18 250 mm×50 mm×10 μm; mobile phase: [water (10 mM $NH_4HCO_3$)-ACN]; B %: 20%-50%, 20 min) to give N-(4-(6-amino-5-(2-(N-methylacrylamido)ethoxy)pyrimidin-4-yl)-2-methylbenzyl)-5-(tert-butyl)-1,3,4-oxadiazole-2-carboxamide as a white solid (130 mg, yield: 25%). ESI-MS $(M+H)^+$: 494.3. $^1H$ NMR: 400 MHz MeOD-$d_4$ δ: 8.25-8.16 (m, 1H), 7.63-7.49 (m, 2H), 7.44-7.39 (m, 1H), 6.77-6.68 (m, 1H), 6.25-6.16 (m, 1H), 5.78-5.66 (m, 1H), 4.70-4.61 (m, 2H), 3.75-3.62 (m, 5H), 3.02-2.96 (m, 1H), 2.78-2.74 (m, 1H), 2.48-2.42 (m, 3H), 1.52-1.46 (m, 9H).

Example 2. Synthesis of N-(4-(6-amino-5-(2-(N-methylacrylamido)ethoxy)pyrimidin-4-yl)-2-methylbenzyl)-5-(tert-butyl)-1,2,4-oxadiazole-3-carboxamide (compound 2)

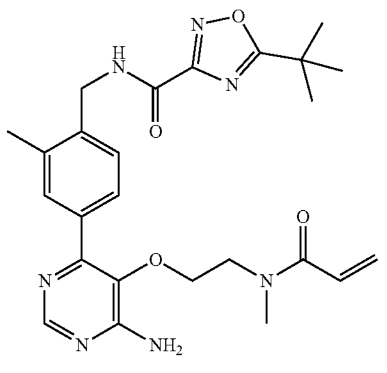 [SMILES: C=CC(=O)N(C)CCOc1c(N)ncnc1-c1ccc(CNC(=O)c2noc(C(C)(C)C)n2)c(C)c1]

1. Preparation of 4-amino-6-chloropyrimidin-5-ol

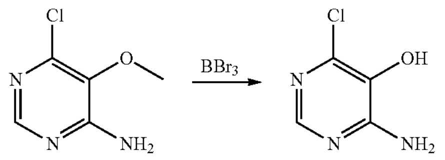

To a solution of 6-chloro-5-methoxypyrimidin-4-amine (10.0 g, 62.7 mmol) in DCM (100 mL) was added $BBr_3$ (47.1 g, 188 mmol, 18.1 mL), and the mixture was stirred at 20° C. for 24 h. To the mixture was added MeOH (20 mL) and stirring continued at 20° C. for 2 h. The mixture was concentrated in vacuo. The mixture was purified prep-HPLC (column: Phenomenex Luna C18 250 mm×80 mm×10 μm; mobile phase: [water (0.1% TFA)-ACN]; B %: 1%-20%, 5 min) to give 4-amino-6-chloropyrimidin-5-ol as a white solid (14.0 g, yield: 99%). The material was carried forward without further purification.

2. Preparation of tert-butyl (2-((4-amino-6-chloropyrimidin-5-yl)oxy)ethyl)(methyl)carbamate

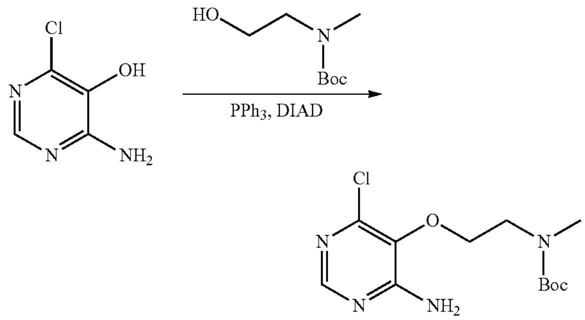

To a solution of 4-amino-6-chloropyrimidin-5-ol (14.0 g, 96.2 mmol) in THF (15 mL) at 15° C. was added $PPh_3$ (37.8 g, 144 mmol) and tert-butyl (2-hydroxyethyl)(methyl)carbamate (20.2 g, 115 mmol). The mixture was stirred at 15° C. for 6 min. Then the reaction mixture was cooled to 0° C. and DIAD (29.2 g, 144 mmol, 28.1 mL) was added. The mixture was allowed to warm to 15° C. and was stirred at that temperature for 12 h. The mixture was concentrated in vacuo and the residue was purified by prep-HPLC (column: Phenomenex Luna C18 250 mm×100 mm×10 μm; mobile phase: [water (0.1% TFA)-ACN]; B %: 20%-40%, 20 min) to give tert-butyl (2-((4-amino-6-chloropyrimidin-5-yl)oxy)ethyl)(methyl)carbamate as a white solid (11.0 g, yield: 38%). $^1H$ NMR: 400 MHz MeOD-$d_4$ δ: 8.61-8.50 (m, 1H), 8.04-7.91 (m, 1H), 4.18-4.04 (m, 2H), 3.71-3.51 (m, 2H), 3.07-2.95 (m, 3H), 1.57-1.39 (m, 9H).

3. Preparation of (2-methyl-4-(4,4,5,5-tetramethyl-1,3,2-dioxaborolan-2-yl)phenyl)methanamine hydrochloride

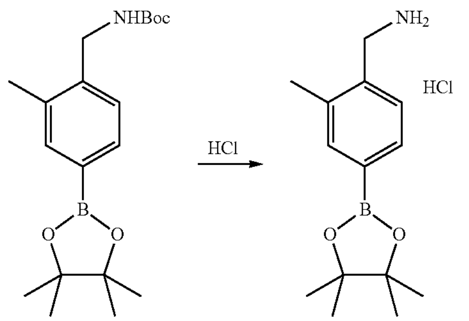

tert-Butyl (2-methyl-4-(4,4,5,5-tetramethyl-1,3,2-dioxaborolan-2-yl)benzyl)carbamate (5.00 g, 14.4 mmol) and an HCl solution (4 M in dixoane, 100 mL) were charged into a one-necked flask. The reaction was stirred at 20° C. for 1 h. The mixture was concentrated in vacuo to give (2-methyl-4-(4,4,5,5-tetramethyl-1,3,2-dioxaborolan-2-yl)phenyl)methanamine hydrochloride as a light yellow solid (4.0 g, yield: 98%), which was carried forward without further purification.

4. Preparation of 5-(tert-butyl)-N-(2-methyl-4-(4,4,5,5-tetramethyl-1,3,2-dioxaborolan-2-yl)benzyl)-1,2,4-oxadiazole-3-carboxamide

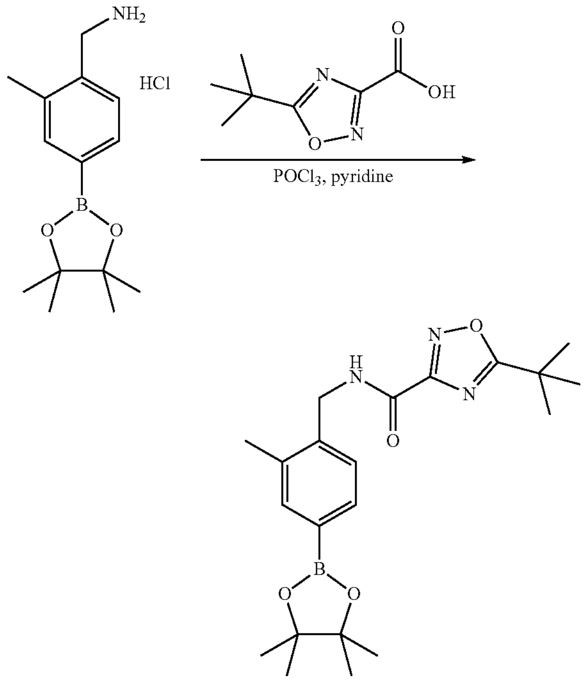

To a solution of (2-methyl-4-(4,4,5,5-tetramethyl-1,3,2-dioxaborolan-2-yl)phenyl)methanamine hydrochloride (3.33 g, 11.8 mmol), in DCM (20 mL) was added 5-(tert-butyl)-1,2,4-oxadiazole-3-carboxylic acid (2.00 g, 11.8 mmol). The reaction mixture was cooled to 0° C. and $POCl_3$ (5.41 g, 35.3 mmol, 3.28 mL) was added, followed by pyridine (5.58 g, 70.5 mmol, 5.69 mL). The reaction was stirred at 20° C. for 1 h. The reaction mixture was poured into a saturated aqueous $NaHCO_3$ solution (300 mL) to quench the reaction and extracted with DCM (300 mL). The organic layer was washed with brine (200 mL), dried ($Na_2SO_4$), filtered, and concentrated in vacuo. The residue was purified by silica gel column chromatography (petroleum ether/EtOAc, grading from 5:1 to 1:1) to give 5-(tert-butyl)-N-(2-methyl-4-(4,4,5,5-tetramethyl-1,3,2-dioxaborolan-2-yl)benzyl)-1,2,4-oxadiazole-3-carboxamide as a light yellow oil (3.4 g, yield: 73%). $^1H$ NMR: (400 MHz $CDCl_3$-d) δ 7.69-7.64 (m, 2H), 7.32 (d, J=7.2 Hz, 1H), 7.07 (br s, 1H), 4.68 (d, J=6.0 Hz, 2H), 2.38 (s, 3H), 1.46 (s, 9H), 1.35 (s, 12H).

5. Preparation of tert-butyl (2-((4-amino-6-(4-((5-(tert-butyl)-1,2,4-oxadiazole-3-carboxamido)methyl)-3-methylphenyl)pyrimidin-5-yl)oxy)ethyl)(methyl)carbamate

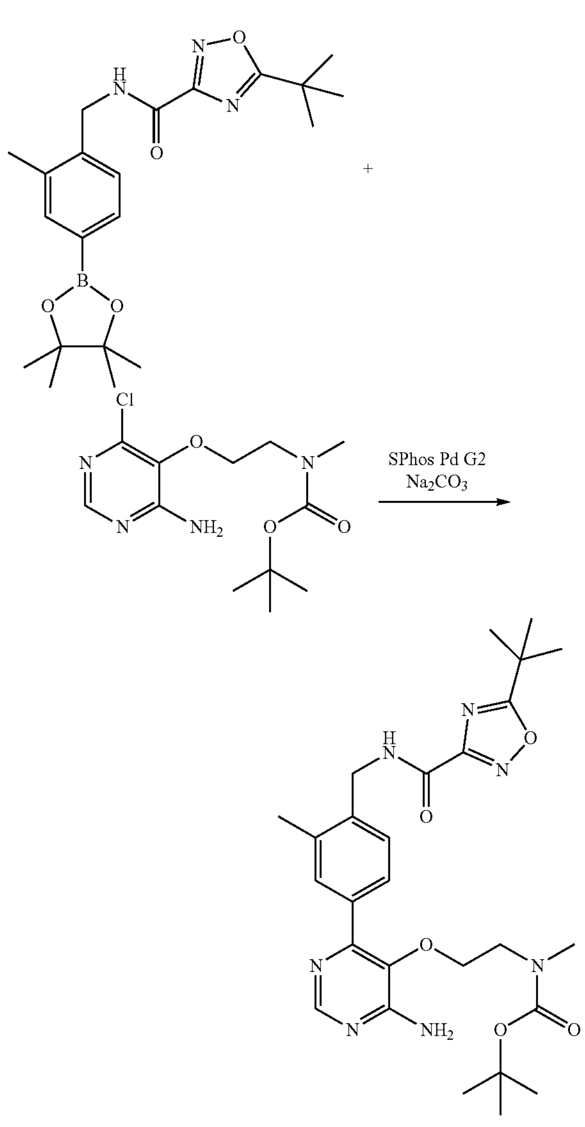

A mixture of tert-butyl (2-((4-amino-6-chloropyrimidin-5-yl)oxy)ethyl)(methyl)-carbamate (217 mg, 0.72 mmol), 5-(tert-butyl)-N-(2-methyl-4-(4,4,5,5-tetramethyl-1,3,2-dioxaborolan-2-yl)benzyl)-1,2,4-oxadiazole-3-carboxamide (300 mg, 0.75 mmol), $Na_2CO_3$ (0.5 M, 2.88 mL), and SPhos Pd G2 (52 mg, 0.07 mmol) in DMF (6 mL) was degassed and purged with $N_2$ 3 times. The reaction mixture was heated to 100° C. and was stirred at that temperature for 4 h under an $N_2$ atmosphere. Multiple batches were combined at this point and the reaction mixture was partitioned between water (500 mL) and EtOAc (500 mL). The organic phase was separated, and the aqueous phase extracted with EtOAc (100 mL×3). The combined organic extracts were dried ($Na_2SO_4$), filtered, and concentrated in vacuo. The crude product was purified by silica gel column chromatography (petroleum ether/EtOAc, grading from 1:0 to 0:1) to give a yellow oil (crude). The yellow oil was purified again by prep-HPLC (column: Phenomenex Luna C18 250 mm×50 mm×10 μm; mobile phase: [water (10 mM $NH_4HCO_3$)-ACN]; B %: 20%-50%, 20 min)) to give tert-butyl (2-((4-amino-6-(4-((5-(tert-butyl)-1,2,4-oxadiazole-3-carboxamido)methyl)-3-methylphenyl)pyrimidin-5-yl)oxy)ethyl)(methyl)-carbamate as an off-white solid (300 mg). $^1H$ NMR: 400 MHz $CDCl_3$-d δ: 8.35 (br s, 1H), 7.82-7.75 (m, 2H), 7.38 (br d, J=8.2 Hz, 1H), 7.24 (br s, 1H), 5.30 (s, 1H), 4.71 (d, J=5.8 Hz, 2H), 3.73-3.64 (m, 2H), 3.45 (br s, 2H), 2.87 (br s, 3H), 2.43 (s, 3H), 1.47 (s, 18H).

6. Preparation of N-(4-(6-amino-5-(2-(methylamino)ethoxy)pyrimidin-4-yl)-2-methylbenzyl)-5-(tert-butyl)-1,2,4-oxadiazole-3-carboxamide

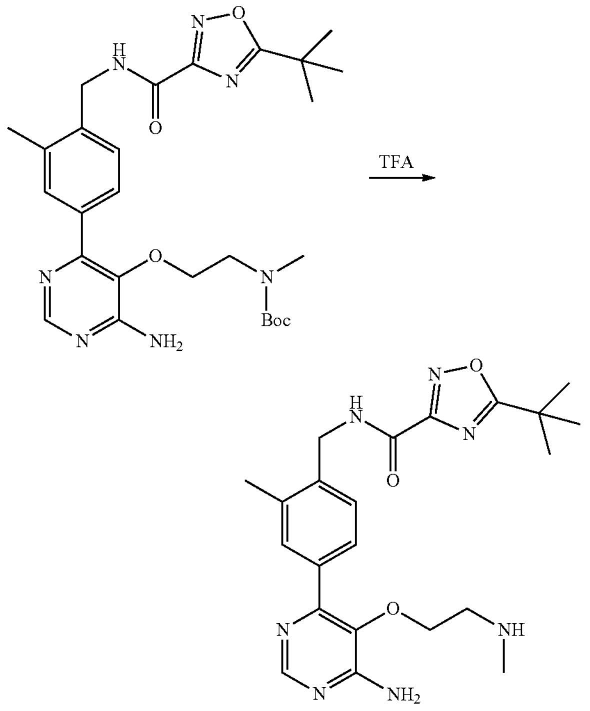

To a solution of tert-butyl (2-((4-amino-6-(4-((5-(tert-butyl)-1,2,4-oxadiazole-3-carboxamido)methyl)-3-methylphenyl)pyrimidin-5-yl)oxy)ethyl)(methyl)carbamate (300 mg, 0.56 mmol) in DCM (10 mL) at 0° C. was added TFA (3.08 g, 27.0 mmol, 2 mL). The reaction was stirred at 20° C. for 12 h. To this mixture was added a saturated aqueous $NaHCO_3$ solution (50 mL), followed by DCM (50 mL). The layers were separated and the aqueous phase was extracted with an additional portion of DCM (50 mL). The organic layers were washed with brine (50 mL), dried ($Na_2SO_4$), filtered, and concentrated in vacuo to give N-(4-(6-amino-5-(2-(methylamino)ethoxy)pyrimidin-4-yl)-2-methylbenzyl)-5-(tert-butyl)-1,2,4-oxadiazole-3-carboxamide as a yellow gum (240 mg, yield: 98%), which was carried forward without further purification.

7. Preparation of N-(4-(6-amino-5-(2-(N-methylacrylamido)ethoxy)pyrimidin-4-yl)-2-methylbenzyl)-5-(tert-butyl)-1,2,4-oxadiazole-3-carboxamide (compound 3)

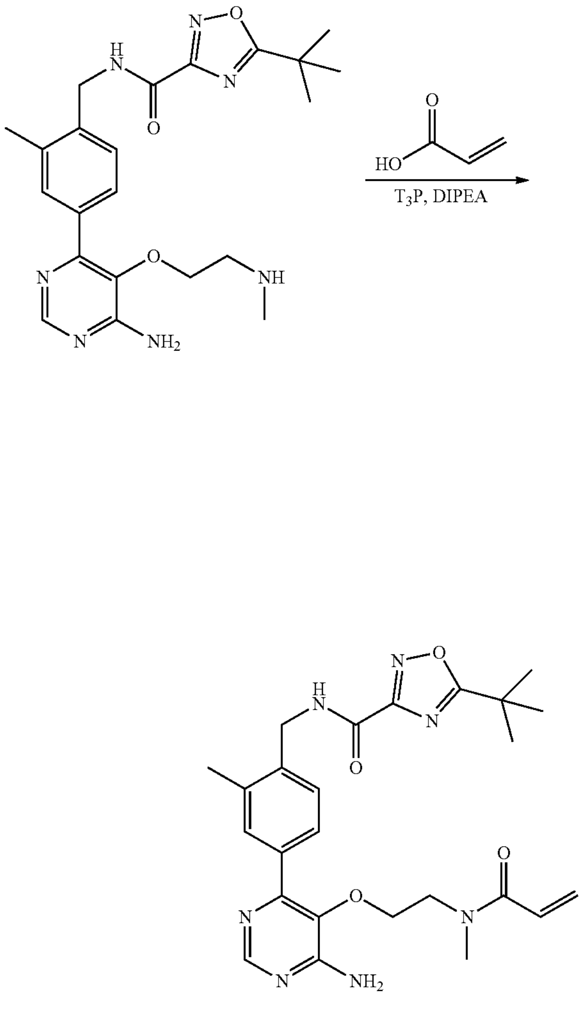

2

To a solution of acrylic acid (59 mg, 0.82 mmol, 56 μL) in DMF (2 mL) at 15° C. was added DIPEA (212 mg, 1.64 mmol, 0.29 mL) and $T_3P$ (226 mg, 710 umol, 0.21 mL). The mixture was stirred at 15° C. for 0.5 h. To a solution of N-(4-(6-amino-5-(2-(methylamino)-ethoxy)pyrimidin-4-yl)-2-methylbenzyl)-5-(tert-butyl)-1,2,4-oxadiazole-3-carboxamide (240 mg, 0.55 mmol) in DMF (2 mL) at 0° C. was added the previously prepared DMF solution in a dropwise manner. The mixture was stirred at 0° C. for 0.5 h. The reaction was added to a saturated aqueous $NaHCO_3$ solution (50 mL) and extracted with EtOAc (50 mL). The organic layer was washed sequentially with $H_2O$ (50 mL) and brine (50 mL), dried ($Na_2SO_4$), filtered, and concentrated in vacuo. The residue was purified by prep-HPLC (column: Waters Xbridge 150 mm×25 mm×5 μm; mobile phase: [water (10 mM $NH_4HCO_3$)-ACN]; B %: 23%-53%, 10 min) to give N-(4-(6-amino-5-(2-(N-methylacrylamido)ethoxy)pyrimidin-4-yl)-2-methylbenzyl)-5-(tert-butyl)-1,2,4-oxadiazole-3-carboxamide as a brown solid (73 mg, yield: 26%). $^1H$ NMR: 400 MHz MeOD-$d_4$ δ: 8.19 (d, J=6.8 Hz, 1H), 7.66-7.48 (m, 2H), 7.44-7.33 (m, 1H), 6.73 (m, 1H), 6.21 (m, 1H), 5.81-5.64 (m, 1H), 4.66 (d, J=5.2 Hz, 2H), 3.75-3.60 (m, 4H), 3.01-2.74 (m, 3H), 2.45 (s, 3H), 1.50 (d, J=2.8 Hz, 9H).

Example 3. Synthesis of 5-(tert-butyl)-N-(2-methyl-4-(5-(2-(N-methylacrylamido)ethoxy)-pyrimidin-4-yl)benzyl)-1,2,4-oxadiazole-3-carboxamide (compound 3)

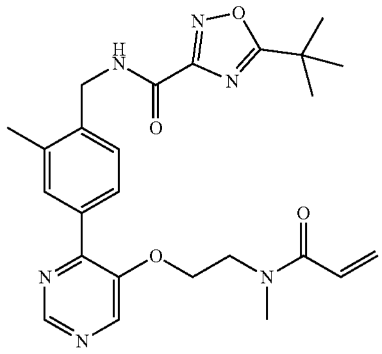 [SMILES: C=CC(=O)N(C)CCOc1cncnc1-c1ccc(CNC(=O)c2noc(C(C)(C)C)n2)c(C)c1]

1. Preparation of tert-butyl (4-bromo-2-methylbenzyl)carbamate

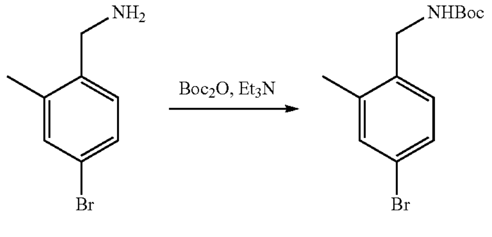

(4-Bromo-2-methylphenyl)methanamine (5.0 g, 25 mmol) and DCM (50 mL) were charged into a one-necked flask. To this solution was added $Et_3N$ (5.1 g, 50 mmol, 7.0 mL) and $Boc_2O$ (5.7 g, 26 mmol, 6.0 mL). The reaction was stirred at 20° C. for 1 h. The mixture was concentrated in vacuo, and the residue was diluted with 1N HCl (50 mL) and EtOAc (50 mL). The layers was separated, and the organic phase was washed with brine (30 mL), dried ($Na_2SO_4$), filtered, and concentrated in vacuo to give tert-butyl (4-bromo-2-methylbenzyl)carbamate as a white solid (7.5 g, yield: 100%), which was carried forward without further purification.

2. Preparation of tert-butyl (2-methyl-4-(4,4,5,5-tetramethyl-1,3,2-dioxaborolan-2-yl)benzyl)carbamate

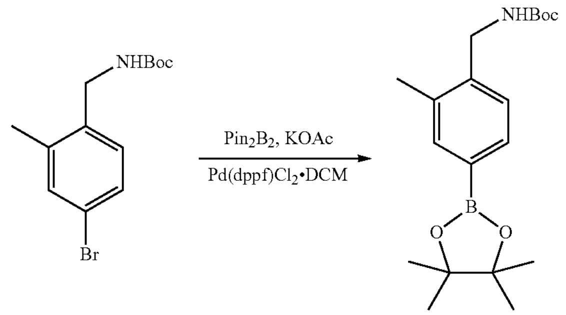

To a solution of tert-butyl (4-bromo-2-methylbenzyl)carbamate (7.5 g, 25 mmol) in dioxane (50 mL) was added Pd(dppf)$Cl_2$•DCM (1.0 g, 1.25 mmol), (bispinacolato)diboron (7.6 g, 30 mmol) and KOAc (4.9 g, 50 mmol). The reaction was stirred at 100° C. for 12 h under a $N_2$ atmosphere. The mixture was cooled, diluted with EtOAc (50 mL), filtered through Celite®, and the filtrate was concentrated in vacuo. The residue was purified by silica gel column chromatography (petroleum ether/EtOAc, grading from 1:0 to 25:1) to give tert-butyl (2-methyl-4-(4,4,5,5-tetramethyl-1,3,2-dioxaborolan-2-yl)benzyl)carbamate as a light yellow solid (8.5 g, yield: 98%), which was carried forward without further purification.

3. Preparation of tert-butyl (4-(5-methoxypyrimidin-4-yl)-2-methylbenzyl)carbamate

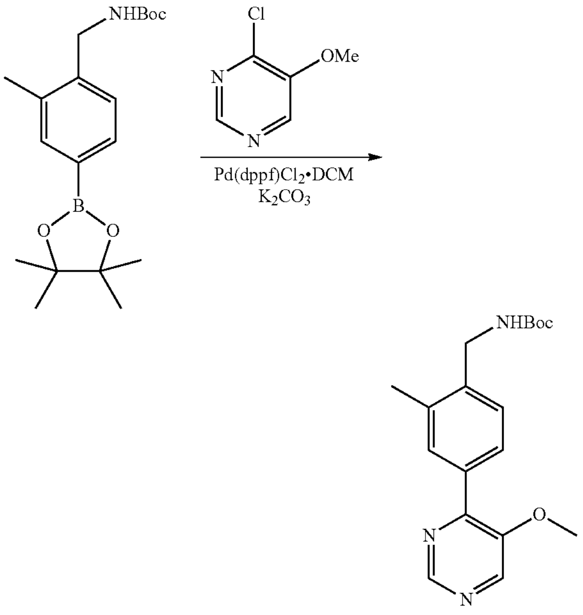

4-Chloro-5-methoxy-pyrimidine (2.1 g, 14.7 mmol), tert-butyl (2-methyl-4-(4,4,5,5-tetramethyl-1,3,2-dioxaborolan-2-yl)benzyl)carbamate (5.1 g, 14.7 mmol), $H_2O$ (6 mL) and dioxane (30 mL) were charged into three-necked flask. To this solution was added Pd(dppf)$Cl_2$•DCM (600 mg, 0.73 mmol) and $K_2CO_3$ (4.1 g, 29.4 mmol). The reaction was stirred at 100° C. for 12 h under a $N_2$ atmosphere. The mixture was diluted with $H_2O$ (100 mL) and EtOAc (100 mL). The organic layer was separated, washed with brine (100 mL), dried ($Na_2SO_4$), filtered, and concentrated in vacuo. The residue was purified by silica gel column chromatography (petroleum ether/EtOAc, grading from 10:1 to 3:1) to give tert-butyl (4-(5-methoxypyrimidin-4-yl)-2-methylbenzyl)carbamate as a yellow solid (4.4 g, yield: 91%). $^1$H NMR: 400 MHz $CDCl_3$-d δ: 8.92 (s, 1H), 8.45 (s, 1H), 7.92-7.87 (m, 2H), 7.35 (d, J=7.6 Hz, 1H), 4.77 (br s, 1H), 4.38 (br d, J=5.2 Hz, 2H), 3.99 (s, 3H), 2.41 (s, 3H), 1.48 (s, 9H).

4. Preparation of tert-butyl (4-(5-hydroxypyrimidin-4-yl)-2-methylbenzyl)carbamate

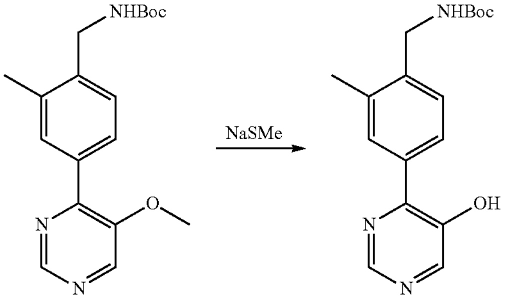

To a solution of tert-butyl (4-(5-methoxypyrimidin-4-yl)-2-methylbenzyl)carbamate (4.4 g, 13.4 mmol) in DMF (30 mL) was added NaSMe (7.2 g, 102 mmol, 6.52 mL). The reaction mixture was stirred at 65° C. for 1 h. The mixture was cooled, diluted with EtOAc (200 mL), $H_2O$ (100 mL) and acidified with 1N HCl until pH=6. The organic layer was separated, washed with brine (100 mL), dried ($Na_2SO_4$), filtered, and concentrated in vacuo. The residue was purified by prep-HPLC (column: Phenomenex Luna C18 250 mm×50 mm×10 μm; mobile phase: [water (0.225% formic acid)-ACN]; B %: 30%-60%, 17 min) to give tert-butyl (4-(5-hydroxypyrimidin-4-yl)-2-methylbenzyl)carbamate as a white solid (1.2 g, yield: 29%). $^1$H NMR: 400 MHz DMSO-$d_6$ δ: 10.68 (s, 1H), 8.72 (s, 1H), 8.42 (s, 1H), 8.02-7.93 (m, 2H), 7.42-7.26 (m, 2H), 4.17 (br d, J=6.0 Hz, 2H), 2.34 (s, 3H), 1.42 (s, 9H).

5. Preparation of 4-(4-(aminomethyl)-3-methylphenyl)pyrimidin-5-ol hydrochloride

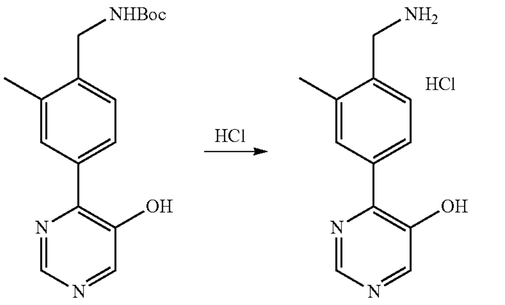 [SMILES: Cc1cc(-c2ncncc2O)ccc1CNC(=O)OC(C)(C)C ; Cl ; Cc1cc(-c2ncncc2O)ccc1CN ; Cl]

A solution of tert-butyl (4-(5-hydroxypyrimidin-4-yl)-2-methylbenzyl)carbamate (1.1 g, 3.5 mmol) in an HCl solution (4 M in dioxane, 10 mL) was stirred at 20° C. for 1 h. The mixture was concentrated in vacuo to give 4-(4-(aminomethyl)-3-methylphenyl)pyrimidin-5-ol hydrochloride as a light yellow solid (870 mg, yield: 99%). $^1H$ NMR: 400 MHz DMSO-$d_6$ δ: 11.10 (br s, 1H), 8.77 (s, 1H), 8.57 (s, 1H), 8.46 (br s, 3H), 8.09-8.02 (m, 2H), 7.53 (d, J=8.0 Hz, 1H), 4.08 (q, J=5.6 Hz, 2H), 2.43 (s, 3H).

6. Preparation of 5-(tert-butyl)-N-(4-(5-hydroxypyrimidin-4-yl)-2-methylbenzyl)-1,2,4-oxadiazole-3-carboxamide

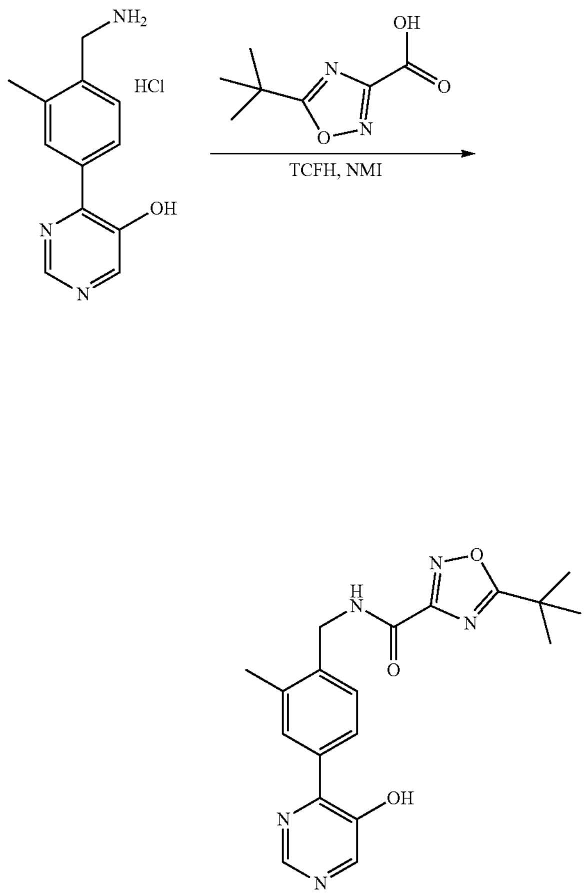

To a solution of 4-(4-(aminomethyl)-3-methylphenyl)pyrimidin-5-ol hydrochloride (870 mg, 3.46 mmol) and 5-(tert-butyl)-1,2,4-oxadiazole-3-carboxylic acid (700 mg, 4.11 mmol) in DMF (10 mL) was added 1-methyl-1H-imidazole (993 mg, 12.1 mmol, 0.96 mL) and TCFH (149 mg, 4.15 mmol). The reaction was stirred at 20° C. for 1 h. The mixture was diluted with $H_2O$ (50 mL), acidified with 1N HCl to pH=6, and extracted with EtOAc (50 mL). The organic layer was washed with brine (30 mL), dried ($Na_2SO_4$), filtered, and concentrated in vacuo to give 5-(tert-butyl)-N-(4-(5-hydroxypyrimidin-4-yl)-2-methylbenzyl)-1,2,4-oxadiazole-3-carboxamide as a light yellow solid (700 mg, yield: 55%), which was carried forward without further purification.

7. Preparation of N-(4-(5-(2-bromoethoxy)pyrimidin-4-yl)-2-methylbenzyl)-5-(tert-butyl)-1,2,4-oxadiazole-3-carboxamide

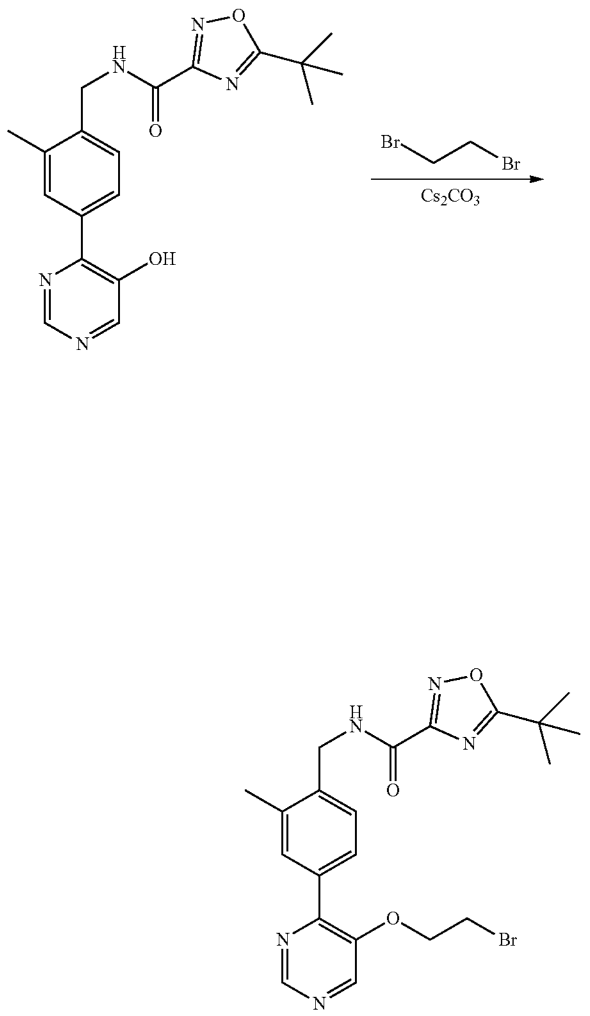

To a solution of 5-(tert-butyl)-N-(4-(5-hydroxypyrimidin-4-yl)-2-methylbenzyl)-1,2,4-oxadiazole-3-carboxamide (500 mg, 1.36 mmol) in DMF (10 mL) was added 1,2-dibromoethane (3.00 g, 16.0 mmol, 1.20 mL) and $Cs_2CO_3$ (1.60 g, 4.91 mmol). The mixture was stirred at 20° C. for 4 h. The mixture was diluted with EtOAc (50 mL) and $H_2O$ (50 mL). The organic layer was separated, washed with brine (50 mL), dried ($Na_2SO_4$), filtered, and concentrated in vacuo to give N-(4-(5-(2-bromoethoxy)pyrimidin-4-yl)-2-methylbenzyl)-5-(tert-butyl)-1,2,4-oxadiazole-3-carboxamide as a light brown oil (645 mg, crude), which was carried forward without further purification.

8. Preparation of 5-(tert-butyl)-N-(2-methyl-4-(5-(2-(methylamino)ethoxy)pyrimidin-4-yl)benzyl)-1,2,4-oxadiazole-3-carboxamide

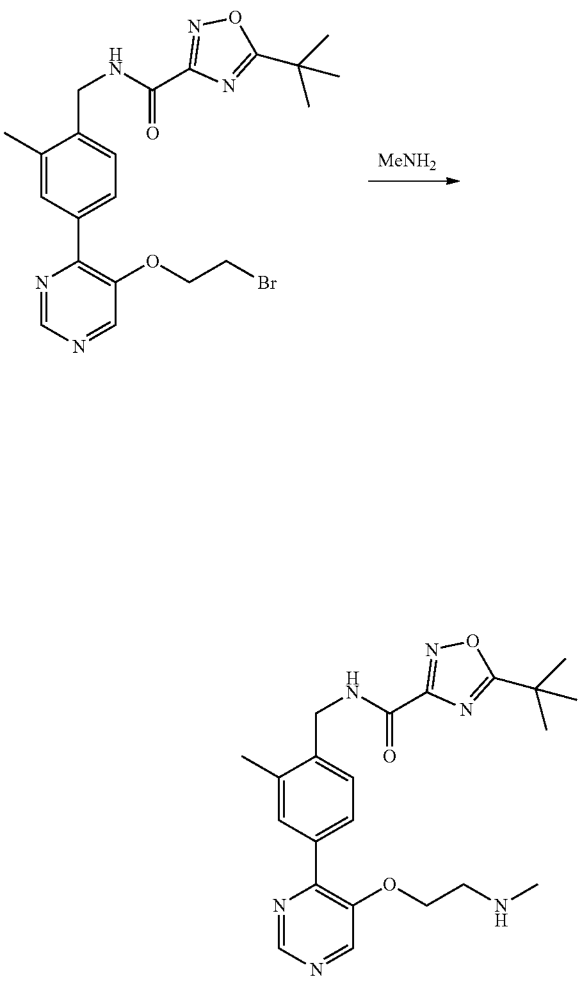

A solution of N-(4-(5-(2-bromoethoxy)pyrimidin-4-yl)-2-methylbenzyl)-5-(tert-butyl)-1,2,4-oxadiazole-3-carboxamide (645 mg, 1.36 mmol) in $MeNH_2$ (2 M, 20 mL) was sealed in a reaction vessel. The reaction was stirred at 70° C. for 12 h. The reaction was cooled and concentrated in vacuo. The residue was diluted with $H_2O$ (30 mL) and extracted with DCM (30 mL×3). The combined organic extracts were washed with brine (20 mL), dried ($Na_2SO_4$), filtered, and concentrated in vacuo to give 5-(tert-butyl)-N-(2-methyl-4-(5-(2-(methylamino)-ethoxy)pyrimidin-4-yl)benzyl)-1,2,4-oxadiazole-3-carboxamide as a light brown oil (540 mg, crude), which was carried forward without further purification.

9. Preparation of 5-(tert-butyl)-N-(2-methyl-4-(5-(2-(N-methylacrylamido)ethoxy)pyrimidin-4-yl)benzyl)-1,2,4-oxadiazole-3-carboxamide (compound 3)

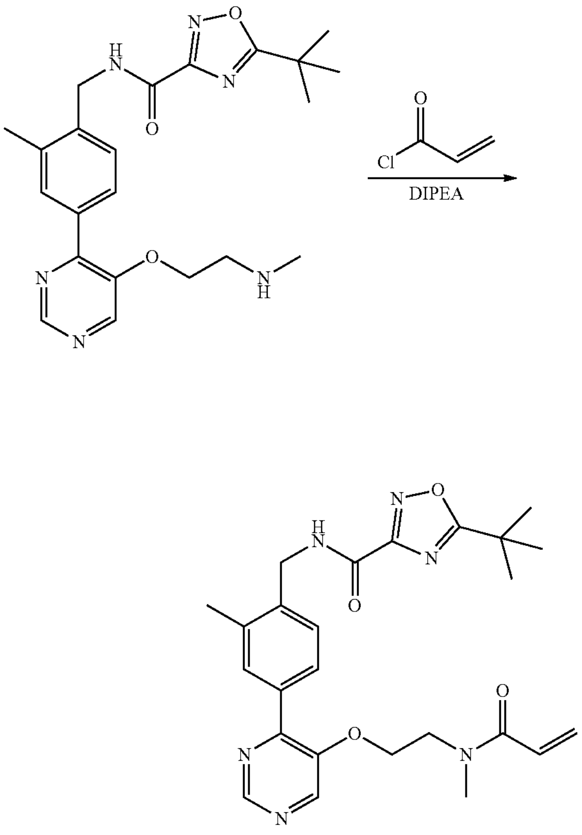

3

To a solution of 5-(tert-butyl)-N-(2-methyl-4-(5-(2-(methylamino)ethoxy)pyrimidin-4-yl)benzyl)-1,2,4-oxadiazole-3-carboxamide (540 mg, 1.27 mmol) in DCM (10 mL) at 0° C. was added DIPEA (493 mg, 3.82 mmol, 0.67 mL) and prop-2-enoyl chloride (173 mg, 1.91 mmol, 0.16 mL). The mixture was stirred at 0° C. for 30 min. The mixture was diluted with $H_2O$ (20 mL) and extracted with DCM (20 mL×2). The organic layer was washed with brine (20 mL), dried ($Na_2SO_4$), filtered, and concentrated in vacuo. The residue was purified by prep-HPLC (column: Waters Xbridge C18 150 mm×50 mm×10 μm; mobile phase: [water (10 mM $NH_4HCO_3$)-ACN]; B %: 27%-57%, 11.5 min) to give 5-(tert-butyl)-N-(2-methyl-4-(5-(2-(methylamino)ethoxy)pyrimidin-4-yl)benzyl)-1,2,4-oxadiazole-3-carboxamide as a white solid (110 mg, yield: 18%). $^1H$ NMR: 400 MHz MeOD-$d_4$ δ: 8.83 (d, J=4.4 Hz, 1H), 8.63 (d, J=1.2 Hz, 1H), 7.87-7.81 (m, 1H), 7.77-7.70 (m, 1H), 7.41 (dd, J=8.0 Hz, 5.6 Hz, 1H), 6.74-6.62 (m, 1H), 6.23-6.06 (m, 1H), 5.74-5.53 (m, 1H), 4.66 (s, 2H), 4.40 (q, J=5.6 Hz, 2H), 3.97-3.87 (m, 2H), 3.11-3.00 (m, 3H), 2.47 (d, J=3.6 Hz, 3H), 1.51 (s, 9H).

Examples 4-28. Compounds 4-28 were synthesized according to similar procedures described in Methods A, B, and C and Examples 1-3. The characterization data of these compounds are listed in Table 1.

TABLE 1

| Example Number | Name | Structure | Characterization Data |
|---|---|---|---|
| 4 | 5-(tert-butyl)-N-(2-methyl-4-(3-(2-(N-methylacrylamido)ethoxy) pyridin-4-yl)benzyl)-1,2,4-oxadiazole-3-carboxamide | 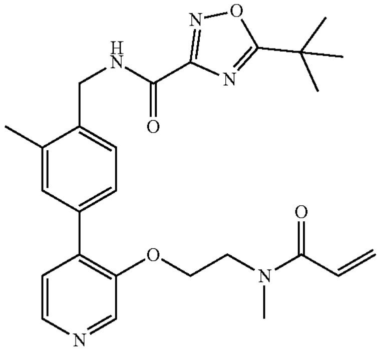 [SMILES: C=CC(=O)N(C)CCOc1cnccc1-c1ccc(CNC(=O)c2noc(C(C)(C)C)n2)c(C)c1] | ESI-MS $(M + H)^+$: 478.1. $^1H$ NMR (500 MHz, DMSO-$d_6$) δ: 9.43 (t, J = 5.8 Hz, 1H), 8.46 (d, J = 6.1 Hz, 1H), 8.27 (dd, J = 4.9 Hz, 3.1 Hz, 1H), 7.45-7.23 (m, 4H), 6.77-6.55 (m, 1H), 6.16-5.90 (m, 1H), 5.69-5.37 (m, 1H), 4.48 (d, J = 6.1 Hz, 2H), 4.26 (q, J = 5.3 Hz, 2H), 3.82-3.67 (m, 2H), 3.02-2.83 (m, 3H), 1.44 (s, 9H). |
| 5 | 5-(tert-butyl)-N-(3-fluoro-2-methyl-4-(3-(2-(N-methylacrylamido)ethoxy) pyridin-4-yl)benzyl)-1,2,4-oxadiazole-3-carboxamide | 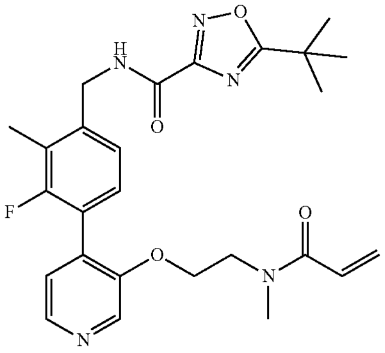 [SMILES: C=CC(=O)N(C)CCOc1cnccc1-c1ccc(CNC(=O)c2noc(C(C)(C)C)n2)c(C)c1F] | ESI-MS $(M + H)^+$: 496.0. $^1H$ NMR (500 MHz, DMSO-$d_6$) δ: 9.53-9.41 (m, 1H), 8.49 (d, J = 8.5 Hz, 1H), 8.29 (dd, J = 4.6 Hz, 3.4 Hz, 1H), 7.26 (dd, J = 6.7 Hz, 4.9 Hz, 1H), 7.23-7.12 (m, 2H), 6.71-6.35 (m, 1H), 6.14-5.83 (m, 1H), 5.69-5.25 (m, 1H), 4.50 (dd, J = 5.8 Hz, 2.1 Hz, 2H), 4.25 (dt, J = 8.1 Hz, 5.4 Hz, 2H), 3.73-3.57 (m, 2H), 2.90-2.74 (m, 3H), 1.43 (s, 9H). |
| 6 | N-(2-((4-amino-6-(4-((1-(tert-butyl)-4-oxo-1,4,6,7-tetrahydro-5H-pyrazolo[4,3-c]pyridin-5-yl)methyl)-3-methylphenyl)pyrimidin-5-yl)oxy)ethyl)-N-methylacrylamide | 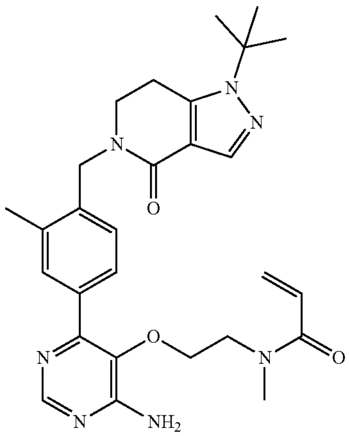 [SMILES: C=CC(=O)N(C)CCOc1c(N)ncnc1-c1ccc(CN2CCc3c(cnn3C(C)(C)C)C2=O)c(C)c1] | ESI-MS $(M + H)^+$: 518.1. $^1H$ NMR: (400 MHz, METHANOL-$d_4$) δ: 8.17 (d, J = 6.4 Hz, 1H), 7.80 (d, J = 6.4 Hz, 1H), 7.65-7.50 (m, 2H), 7.29 (t, J = 8.4 Hz, 1H), 6.83-6.65 (m, 1H), 6.23-6.10 (m, 1H), 5.71-5.59 (m, 1H), 4.77 (s, 2H), 3.76-3.55 (m, 6H), 3.29-3.23 (m, 2H), 3.04-2.72 (m, 3H), 2.38 (s, 3H), 1.65 (d, J = 2.0 Hz, 9H). |
| 7 | N-(4-(6-amino-5-(2-(N-methylacrylamido)ethoxy) pyrimidin-4-yl)-2-methylbenzyl)-3-(tert-butyl)-1,2,4-oxadiazole-5-carboxamide | 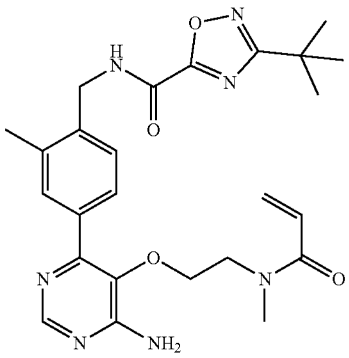 [SMILES: C=CC(=O)N(C)CCOc1c(N)ncnc1-c1ccc(CNC(=O)c2nc(C(C)(C)C)no2)c(C)c1] | ESI-MS $(M + Na)^+$: 516.1. $^1H$ NMR: (500 MHz, METHANOL-$d_4$) δ: 8.20 (d, J = 9.0 Hz, 1H), 7.66-7.50 (m, 2H), 7.44-7.37 (m, 1H), 6.79-6.68 (m, 1H), 6.22 (d, J = 17.0 Hz, 1H), 5.76-5.67 (m, 1H), 4.66-4.65 (d, J = 6.5 Hz, 2H), 3.76-3.65 (m, 4H), 3.03-2.73 (m, 3H), 2.46 (d, J = 2.5 Hz, 3H), 1.44 (d, J = 4.0 Hz, 9H). |

TABLE 1-continued

| Example Number | Name | Structure | Characterization Data |
|---|---|---|---|
| 8 | N-(4-(6-amino-5-(2-(N-methylacrylamido)ethoxy) pyrimidin-4-yl)-2-methylbenzyl)-1-(tert-butyl)-1H-1,2,3-triazole-4-carboxamide | 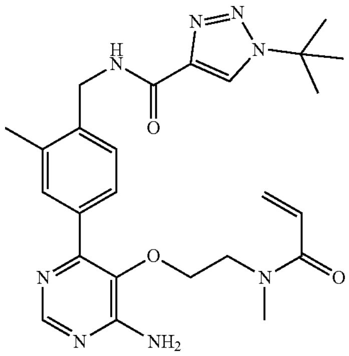 [SMILES: C=CC(=O)N(C)CCOc1c(N)ncnc1-c1ccc(CNC(=O)c2cn(C(C)(C)C)nn2)c(C)c1] | ESI-MS (M + Na)$^+$: 515.1 $^1$H NMR: (500 MHz, METHANOL-$d_4$) δ: 8.50 (d, J = 3.0 Hz, 1H), 8.17 (d, J = 9.0 Hz, 1H), 7.61-7.48 (m, 2H), 7.40-7.37 (m, 1H), 6.70-6.68 (m, 1H), 6.22-6.14 (m, 1H), 5.67-5.65 (m, 1H), 4.65 (d, J = 5.0 Hz, 2H), 3.73-3.63 (m, 4H), 2.97-2.75 (m, 3H), 2.44 (d, J = 2.5 Hz, 3H), 1.73-1.69 (m, 9H). |
| 9 | N-(2-((4-amino-6-(3-methyl-4-((4-neopentyl-2-oxopiperazin-1-yl)methyl)phenyl)pyrimidin-5-yl)oxy)ethyl)-N-methylacrylamide | 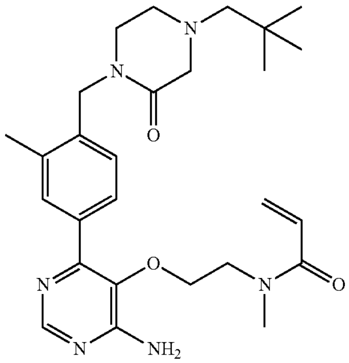 [SMILES: C=CC(=O)N(C)CCOc1c(N)ncnc1-c1ccc(CN2CCN(CC(C)(C)C)CC2=O)c(C)c1] | ESI-MS (M + Na)$^+$: 517.1 $^1$H NMR: (500 MHz, METHANOL-$d_4$) δ: 8.21 (d, J = 4.5 Hz, 1H), 7.62-7.51 (m, 2H), 7.24 (d, J = 6.5 Hz, 1H), 6.81-6.68 (m, 1H), 6.25-6.17 (m, 1H), 5.82-5.66 (m, 1H), 4.70 (s, 2H), 3.76-3.64 (m, 4H), 3.36 (d, J = 10.0 Hz, 2H), 3.30-3.25 (m, 2H), 3.03-2.73 (m, 5H), 2.36 (d, J = 1.5 Hz, 3H), 2.24 (d, J = 11.0 Hz, 2H), 0.93 (d, J = 2.5 Hz, 9H). |
| 10 | N-(4-(6-amino-5-(2-(N-methylacrylamido)ethoxy) pyrimidin-4-yl)-2-methylbenzyl)-1-(tert-butyl)-1H-pyrazole-4-carboxamide | 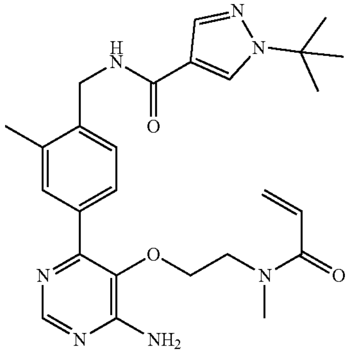 [SMILES: C=CC(=O)N(C)CCOc1c(N)ncnc1-c1ccc(CNC(=O)c2cnn(C(C)(C)C)c2)c(C)c1] | ESI-MS (M + Na)$^+$: 514.1 $^1$H NMR: (500 MHz, METHANOL-$d_4$) δ: 8.62 (s, 1H), 8.37-8.27 (m, 2H), 8.04-7.96 (m, 1H), 7.58-7.51 (m, 1H), 7.47-7.39 (m, 2H), 6.71-6.62 (m, 1H), 6.21-6.08 (m, 1H), 5.68-5.61 (m, 1H), 5.67-5.63 (m, 1H), 4.59 (d, J = 4.5 Hz, 2H), 3.76-3.64 (m, 4H), 2.98-2.71 (m, 3H), 2.44 (d, J = 9.0 Hz, 3H), 1.61 (d, J = 7.0 Hz, 9H). |
| 11 | N-(2-((4-amino-6-(4-((2-cyclopropyl-6-oxo-4,6-dihydro-5H-thieno[2,3-c]pyrrol-5-yl)methyl)-3-methylphenyl)pyrimidin-5-yl)oxy)ethyl)-N-methylacrylamide | 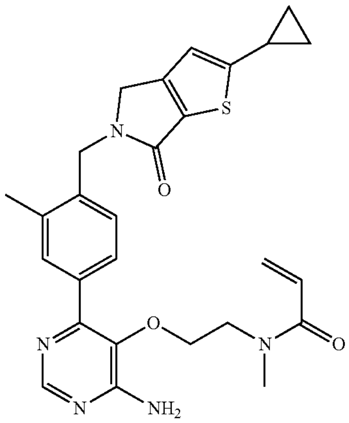 [SMILES: C=CC(=O)N(C)CCOc1c(N)ncnc1-c1ccc(CN2Cc3cc(C4CC4)sc3C2=O)c(C)c1] | ESI-MS (M + Na)$^+$: 526.1 $^1$H NMR: (500 MHz, METHANOL-$d_4$) δ: 8.19 (d, J = 5.5 Hz, 1H), 7.64-7.50 (m, 2H), 7.27-7.22 (m, 1H), 6.86 (d, J = 1.5 Hz, 1H), 6.77-6.63 (m, 1H), 6.21-6.08 (m, 1H), 5.68-5.62 (m, 1H), 4.81 (d, J = 5.5 Hz, 2H), 4.25 (d, J = 17.5 Hz, 2H), 3.75-3.63 (m, 4H), 3.03-2.71 (m, 3H), 2.40 (s, 3H), 2.24-2.20 (m, 1H), 1.18-1.08 (m, 2H), 0.84-0.77 (m, 2H). |

TABLE 1-continued

| Example Number | Name | Structure | Characterization Data |
|---|---|---|---|
| 12 | N-(2-((4-(4-((1-(tert-butyl)-4-oxo-1,4,6,7-tetrahydro-5H-pyrazolo[4,3-c]pyridin-5-yl)methyl)-3-methylphenyl)pyridin-3-yl)oxy)ethyl)-N-methylacrylamide | 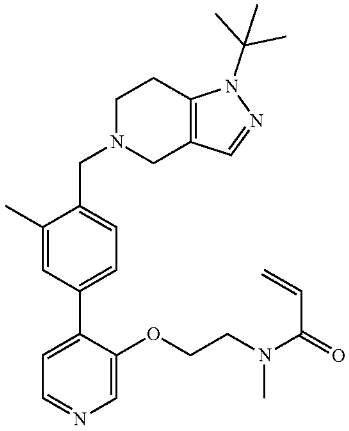 | ESI-MS (M + H)$^+$: 502.3 $^1$H NMR: (500 MHz, METHANOL-$d_4$) δ: 8.37 (d, J = 5.0 Hz, 1H), 8.24 (t, J = 5.0 Hz, 1H), 7.79 (s, 1H), 7.46-7.25 (m, 4H), 6.72-6.48 (m, 1H), 6.23-5.92 (m, 1H), 5.73-5.42 (m, 1H), 4.76 (s, 2H), 4.28 (t, J = 5.0 Hz, 2H), 3.83-3.79 (m, 2H), 3.59 (t, J = 5.0 Hz, 2H), 3.28-3.18 (m, 2H), 3.02-2.87 (m, 3H), 2.37 (s, 3H), 1.65 (s, 9H). |
| 13 | 5-(tert-butyl)-N-(3-fluoro-4-(3-(2-(N-methylacrylamido)ethoxy) pyridin-4-yl)benzyl)-1,2,4-oxadiazole-3-carboxamide | 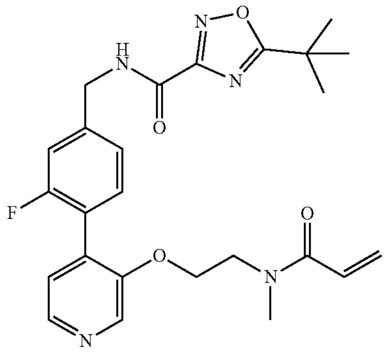 [SMILES: C=CC(=O)N(C)CCOc1cnccc1-c1ccc(CNC(=O)c2noc(C(C)(C)C)n2)cc1F] | ESI-MS (M + H)$^+$: 482.2 $^1$H NMR: (400 MHz, DMSO-$d_6$) δ: 9.54 (s, 1H), 8.48 (d, J = 5.6 Hz, 1H), 8.28 (s, 1H), 7.36-7.19 (m, 4H), 6.68-6.40 (m, 1H), 6.10-5.87 (m, 1H), 5.65-5.35 (m, 1H), 4.49 (d, J = 5.2 Hz, 2H), 4.25-4.23 (m, 2H), 3.68-3.60 (m, 2H), 2.83-2.76 (m, 3H), 1.42 (s, 9H). |
| 14 | 5-(tert-butyl)-N-(4-(3-(2-(N-methylacrylamido)ethoxy) pyridin-4-yl)-2-(trifluoromethyl)benzyl)-1,2,4-oxadiazole-3-carboxamide | 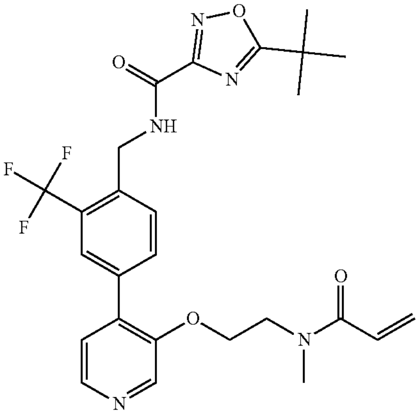 [SMILES: C=CC(=O)N(C)CCOc1cnccc1-c1ccc(CNC(=O)c2noc(C(C)(C)C)n2)c(C(F)(F)F)c1] | ESI-MS (M + H)$^+$: 532.2. $^1$H NMR (500 MHz, DMSO-$d_6$) δ: 9.63 (q, J = 6.1 Hz, 1H), 8.53 (d, J = 10.4 Hz, 1H), 8.33 (d, J = 4.9 Hz, 1H), 7.97-7.80 (m, 2H), 7.57 (t, J = 7.3 Hz, 1H), 7.45 (dd, J = 14.0 Hz, 4.9 Hz, 1H), 6.77-6.47 (m, 1H), 6.17-5.86 (m, 1H), 5.70-5.36 (m, 1H), 4.69 (br d, J = 6.1 Hz, 2H), 4.35-4.27 (m, 2H), 3.78-3.67 (m, 2H), 2.99-2.79 (m, 3H), 1.46 (s, 9H). |
| 15 | 1-(tert-butyl)-N-(2-chloro-3-fluoro-4-(3-(2-(N-methylacrylamido)ethoxy) pyridin-4-yl)benzyl)-1H-pyrazole-3-carboxamide | 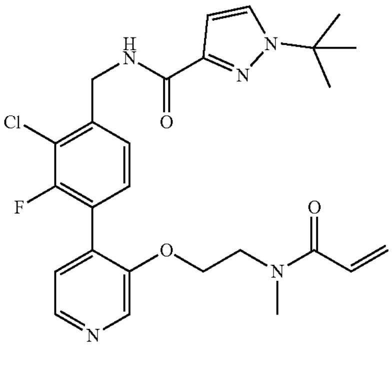 [SMILES: C=CC(=O)N(C)CCOc1cnccc1-c1ccc(CNC(=O)c2ccn(C(C)(C)C)n2)c(Cl)c1F] | ESI-MS (M + Na)$^+$: 536.1 $^1$H NMR: (500 MHz, METHANOL-$d_4$) δ: 8.45 (d, J = 13.0 Hz, 1H), 8.31 (dd, J = 6.0 Hz, 4.5 Hz, 1H), 7.85 (dd, J = 4.5 Hz, 2.5 Hz, 1H), 7.42-7.25 (m, 3H), 6.78 (t, J = 2.0 Hz, 1H), 6.67-6.43 (m, 1H), 6.22-5.98 (m, 1H), 5.72-5.46 (m, 1H), 4.74 (d, J = 1.0 Hz, 2H), 4.34 (t, J = 5.0 Hz, 2H), 3.86-3.70 (m, 2H), 2.91 (d, J = 9.5 Hz, 3H), 1.71-1.62 (m, 9H). |

TABLE 1-continued

| Example Number | Name | Structure | Characterization Data |
| --- | --- | --- | --- |
| 16 | 5-(tert-butyl)-N-(2-methyl-4-(3-(2-(N-methylacrylamido)ethoxy)pyridin-4-yl)benzyl)isoxazole-3-carboxamide | 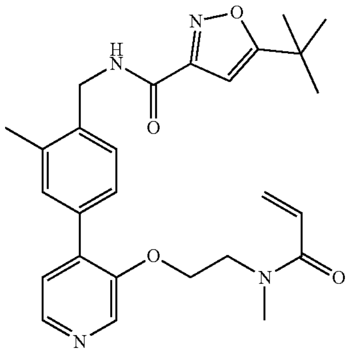 [SMILES: C=CC(=O)N(C)CCOc1cnccc1-c1ccc(CNC(=O)c2cc(C(C)(C)C)on2)c(C)c1] | ESI-MS $(M + Na)^+$: 499.2 $^1H$ NMR: (500 MHz, DMSO-$d_6$) δ: 9.21 (s, 1H), 8.45 (d, J = 6.0 Hz, 1H), 8.26 (dd, J = 5.0 Hz, 3.0 Hz, 1H), 7.39-7.25 (m, 4H), 6.73-6.56 (m, 2H), 6.13-5.93 (m, 1H), 5.67-5.40 (m, 1H), 4.45 (d, J = 6.0 Hz, 2H), 4.25 (q, J = 5.0 Hz, 2H), 3.78-3.66 (m, 2H), 2.99-2.83 (m, 3H), 2.35 (s, 3H), 1.33 (s, 9H). |
| 17 | 5-(tert-butyl)-N-(2,3-difluoro-4-(3-(2-(N-methylacrylamido)ethoxy)pyridin-4-yl)benzyl)isoxazole-3-carboxamide | 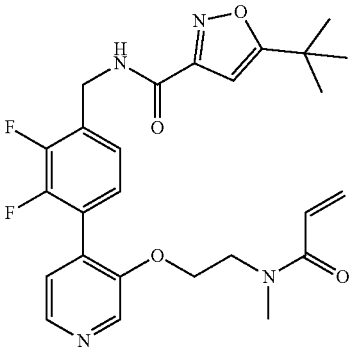 [SMILES: C=CC(=O)N(C)CCOc1cnccc1-c1ccc(CNC(=O)c2cc(C(C)(C)C)on2)c(F)c1F] | ESI-MS $(M + Na)^+$: 521.1 $^1H$ NMR: (400 MHz, DMSO-$d_6$) δ: 9.34 (t, J = 5.2 Hz, 1H), 8.49 (d, J = 7.2 Hz, 1H), 8.28 (dd, J = 8.4 Hz, 1.6 Hz, 1H), 7.30-7.13 (m, 3H), 6.64-6.39 (m, 2H), 6.07-5.85 (m, 1H), 5.62-5.33 (m, 1H), 4.51 (d, J = 5.6 Hz, 2H), 4.26-4.21 (m, 2H), 3.69-3.57 (m, 2H), 2.84-2.74 (m, 3H), 1.29 (s, 9H). |
| 18 | 3-(1-fluoro-2-methylpropan-2-yl)-N-(4-(3-(2-(N-methylacrylamido)ethoxy)pyridin-4-yl)-2-(trifluoromethyl)benzyl)-1,2,4-oxadiazole-5-carboxamide | 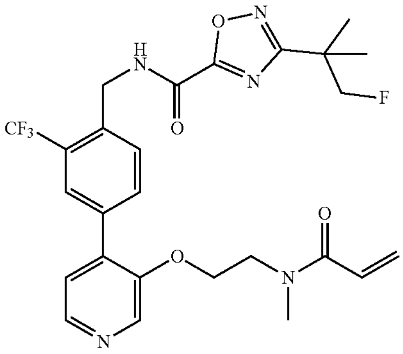 [SMILES: C=CC(=O)N(C)CCOc1cnccc1-c1ccc(CNC(=O)c2nc(C(C)(C)CF)no2)c(C(F)(F)F)c1] | ESI-MS $(M + H)^+$: 550.0 $^1H$ NMR: (500 MHz, $CDCl_3$-d) δ: 8.46-8.29 (m, 2H), 8.18-7.87 (m, 1H), 7.80-7.58 (m, 3H), 7.27-7.19 (m, 1H), 6.56-6.32 (m, 1H), 6.32-6.12 (m, 1H), 5.72-5.45 (m, 1H), 4.88 (brd, J = 6.7 Hz, 2H), 4.56 (s, 1H), 4.46 (s, 1H), 4.35-4.16 (m, 2H), 3.82-3.67 (m, 2H), 3.02-2.85 (m, 3H), 1.43 (d, J = 1.2 Hz, 6H). |
| 19 | 1-(tert-butyl)-N-(2-methyl-4-(3-(2-(N-methylacrylamido)ethoxy)pyridin-4-yl)benzyl)-1H-1,2,3-triazole-4-carboxamide | 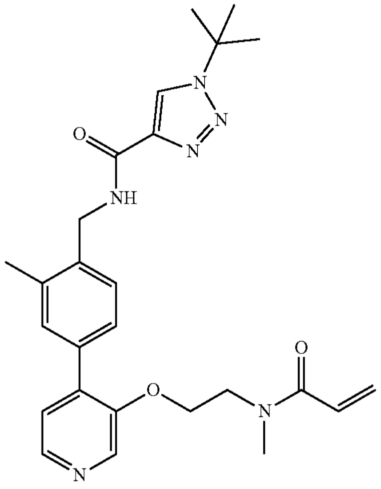 [SMILES: C=CC(=O)N(C)CCOc1cnccc1-c1ccc(CNC(=O)c2cn(C(C)(C)C)nn2)c(C)c1] | ESI-MS $(M + H)^+$: 477.3 $^1H$ NMR: (500 MHz, DMSO-$d_6$) δ: 8.97 (t, J = 6.0 Hz, 1H), 8.72 (s, 1H), 8.45 (d, J = 6.5 Hz, 1H), 8.28-8.25 (m, 1H), 7.40-7.27 (m, 4H), 6.73-6.57 (m, 1H), 6.12-5.93 (m, 1H), 5.65-5.42 (m, 1H), 4.47 (d, J = 6.0 Hz, 2H), 4.28-4.24 (m, 2H), 3.78-3.68 (m, 2H), 2.99-2.86 (m, 3H), 2.37 (s, 3H), 1.65 (s, 9H). |

TABLE 1-continued

| Example Number | Name | Structure | Characterization Data |
|---|---|---|---|
| 20 | 5-(tert-butyl)-N-(2-methyl-4-(5-(2-(N-methylacrylamido)ethoxy) pyrimidin-4-yl)benzyl)isoxazole-3-carboxamide | 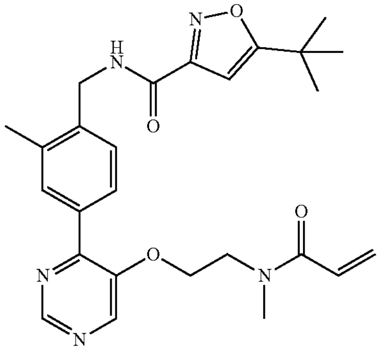 [SMILES: C=CC(=O)N(C)CCOc1cncnc1-c1ccc(CNC(=O)c2cc(C(C)(C)C)on2)c(C)c1] | ESI-MS $(M + Na)^+$: 500.2 $^1H$ NMR: (400 MHz, DMSO-$d_6$) δ: 9.21-9.19 (m, 1H), 8.83-8.81 (m, 1H), 8.67-8.64 (m, 1H), 7.85-7.81 (m, 1H), 7.76-7.72 (m, 1H), 7.28-7.23 (m, 1H), 6.71-6.66 (m, 1H), 6.57 (s, 1H), 6.10-5.98 (m, 1H), 5.62-5.44 (m, 1H), 4.45-4.42 (m, 2H), 4.35-4.31 (m, 2H), 3.85-3.75 (m, 2H), 3.04-2.88 (m, 3H), 2.34 (s, 3H), 1.30 (s, 9H). |
| 21 | 5-(tert-butyl)-N-(3-fluoro-4-(3-(2-(N-methylacrylamido)ethoxy) pyridin-4-yl)benzyl)oxazole-2-carboxamide | 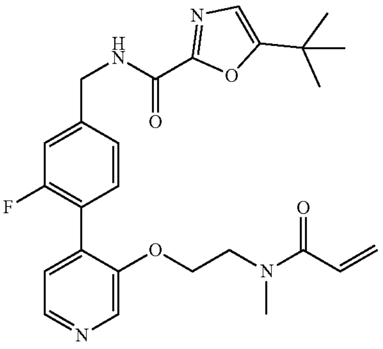 [SMILES: C=CC(=O)N(C)CCOc1cnccc1-c1ccc(CNC(=O)c2ncc(C(C)(C)C)o2)cc1F] | ESI-MS $(M + H)^+$: 481.3 $^1H$ NMR: (500 MHz, DMSO-$d_6$) δ: 9.52-9.46 (m, 1H), 8.49 (d, J = 8.5 Hz, 1H), 8.32-8.27 (m, 1H), 7.39-7.32 (m, 1H), 7.31-7.26 (m, 1H), 7.24-7.17 (m, 2H), 7.13 (s, 1H), 6.68-6.42 (m, 1H), 6.11-5.86 (m, 1H), 5.65-5.35 (m, 1H), 4.47 (d, J = 6.0 Hz, 2H), 4.29-4.22 (m, 2H), 3.70 (t, J = 5.0 Hz, 1H), 3.61 (t, J = 5.0 Hz, 1H), 2.81 (d, J = 26.2 Hz, 3H), 1.31 (s, 9H). |
| 22 | 5-(tert-butyl)-N-(2-methyl-4-(3-(2-(N-methylacrylamido)ethoxy) pyridin-4-yl)benzyl)oxazole-2-carboxamide | 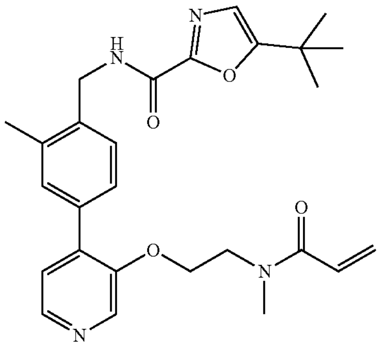 [SMILES: C=CC(=O)N(C)CCOc1cnccc1-c1ccc(CNC(=O)c2ncc(C(C)(C)C)o2)c(C)c1] | ESI-MS $(M + H)^+$: 499.2 $^1H$ NMR: (500 MHz, METHANOL-$d_4$) δ: 8.36 (d, J = 9.0 Hz, 1H), 8.23 (dd, J = 7.0, 5.0 Hz, 1H), 7.46-7.22 (m, 4H), 6.99 (d, J = 2.5 Hz, 1H), 6.71-6.47 (m, 1H), 6.20-5.95 (m, 1H), 5.75-5.39 (m, 1H), 4.61 (s, 2H), 4.27 (dd, J = 7.0, 5.0 Hz, 2H), 3.82-3.31 (m, 2H), 2.93 (d, J = 9.5 Hz, 3H), 2.43 (d, J = 6.5 Hz, 3H), 1.37 (s, 9H). |
| 23 | 5-(tert-butyl)-N-(2,3-difluoro-4-(3-(2-(N-methylacrylamido)ethoxy) pyridin-4-yl)benzyl)oxazole-2-carboxamide | 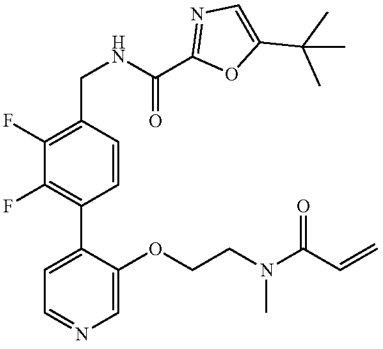 [SMILES: C=CC(=O)N(C)CCOc1cnccc1-c1ccc(CNC(=O)c2ncc(C(C)(C)C)o2)c(F)c1F] | ESI-MS $(M + Na)^+$: 521.1 $^1H$ NMR: (400 MHz, DMSO-$d_6$) δ: 9.50-9.46 (m, 1H), 8.52 (d, J = 7.2 Hz, 1H), 8.33-8.30 (m, 1H), 7.34-7.30 (m, 1H), 7.23-7.11 (m, 3H), 6.67-6.42 (m, 1H), 6.09-5.91 (m, 1H), 5.64-5.36 (m, 1H), 4.53 (d, J = 5.6 Hz, 2H), 4.29-4.24 (m, 2H), 3.72-3.60 (m, 2H), 2.86-2.78 (m, 3H), 1.30 (s, 9H). |

TABLE 1-continued

| Example Number | Name | Structure | Characterization Data |
|---|---|---|---|
| 24 | 5-(tert-butyl)-N-(2-(difluoromethyl)-4-(3-(2-(N-methylacrylamido)ethoxy) pyridin-4-yl)benzyl)isoxazole-3-carboxamide | 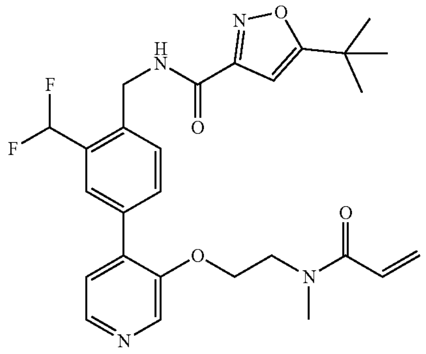 [SMILES: C=CC(=O)N(C)CCOc1cnccc1-c1ccc(CNC(=O)c2cc(C(C)(C)C)on2)c(C(F)F)c1] | ESI-MS $(M + Na)^+$: 535.2 $^1H$ NMR: (500 MHz, DMSO-$d_6$) δ: 9.36 (q, J = 5.5 Hz, 1H), 8.49 (d, J = 7.0 Hz, 1H), 8.30 (dd, J = 4.5 Hz, 2.0 Hz, 1H), 7.81-7.67 (m, 2H), 7.50-7.25 (m, 3H), 6.71-6.52 (m, 2H), 6.11-5.91 (m, 1H), 5.65-5.38 (m, 1H), 4.64 (d, J = 5.5 Hz, 2H), 4.31-4.25 (m, 2H), 3.79-3.65 (m, 2H), 2.97-2.81 (m, 3H), 1.33 (s, 9H). |
| 25 | 3-(tert-butyl)-N-(2-chloro-3-fluoro-4-(3-(2-(N-methylacrylamido)ethoxy) pyridin-4-yl)benzyl)isoxazole-5-carboxamide | 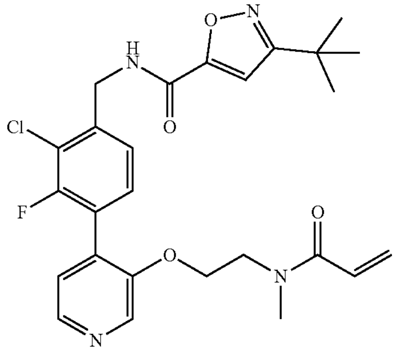 [SMILES: C=CC(=O)N(C)CCOc1cnccc1-c1ccc(CNC(=O)c2cc(C(C)(C)C)no2)c(Cl)c1F] | ESI-MS $(M + Na)^+$: 537.1 $^1H$ NMR: (500 MHz, DMSO-$d_6$) δ: 9.56 (s, 1H), 8.57-8.28 (m, 2H), 7.44-7.20 (m, 4H), 6.70-6.38 (m, 1H), 6.12-5.86 (m, 1H), 5.68-5.34 (m, 1H), 4.59 (d, J = 5.5 Hz, 2H), 4.32-4.24 (m, 2H), 3.74-3.58 (m, 2H), 2.92-2.75 (m, 3H), 1.32 (s, 9H). |
| 26 | 1-(tert-butyl)-N-(4-(3-(2-(N-methylacrylamido)ethoxy) pyridin-4-yl)-2-(trifluoromethoxy)benzyl)-1H-1,2,3-triazole-4-carboxamide | 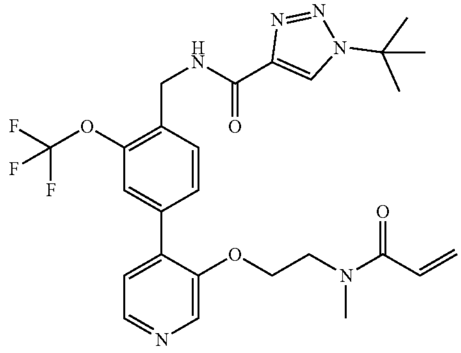 [SMILES: C=CC(=O)N(C)CCOc1cnccc1-c1ccc(CNC(=O)c2cn(C(C)(C)C)nn2)c(OC(F)(F)F)c1] | ESI-MS $(M + Na)^+$: 569.1 $^1H$ NMR: (400 MHz, DMSO-$d_6$) δ: 9.12 (d, J = 4.0 Hz, 1H), 8.72 (s, 1H), 8.49 (d, J = 8.0 Hz, 1H), 8.29 (d, J = 8.0 Hz, 1H), 7.56-7.53 (m, 2H), 7.47-7.45 (m, 1H), 7.39-7.37 (m, 1H), 6.67-6.53 (m, 1H), 6.09-5.91 (m, 1H), 5.63-5.39 (m, 1H), 4.56 (d, J = 8.0 Hz, 2H), 4.28 (d, J = 8.0 Hz, 2H), 3.76-3.66 (m, 2H), 2.95-2.83 (m, 3H), 1.64 (s, 9H). |
| 27 | 5-(tert-butyl)-N-methyl-N-(2-methyl-4-(3-(2-(N-methylacrylamido)ethoxy) pyridin-4-yl)benzyl)isoxazole-3-carboxamide | 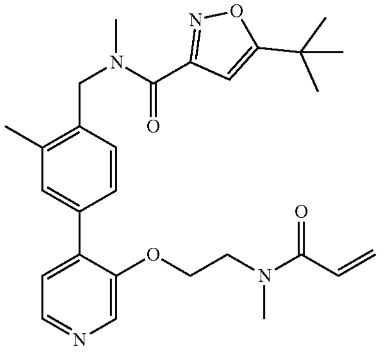 [SMILES: C=CC(=O)N(C)CCOc1cnccc1-c1ccc(CN(C)C(=O)c2cc(C(C)(C)C)on2)c(C)c1] | ESI-MS $(M + H)^+$: 491.3 $^1H$ NMR: (400 MHz, DMSO-$d_6$) δ: 8.42 (s, 1H), 8.25-8.22 (m, 1H), 7.40-7.07 (m, 4H), 6.71-6.43 (m, 2H), 6.08-5.86 (m, 1H), 5.63-5.31 (m, 1H), 4.75-4.68 (m, 2H), 4.24-4.22 (m, 2H), 3.74-3.66 (m, 2H), 2.99-2.79 (m, 6H), 2.29-2.18 (m, 3H), 1.32-1.25 (m, 9H). |

TABLE 1-continued

| Example Number | Name | Structure | Characterization Data |
|---|---|---|---|
| 28 | 3-(tert-butyl)-N-(2-methyl-4-(5-(2-(N-methylacrylamido)ethoxy) pyrimidin-4-yl)benzyl)-1,2,4-oxadiazole-5-carboxamide | 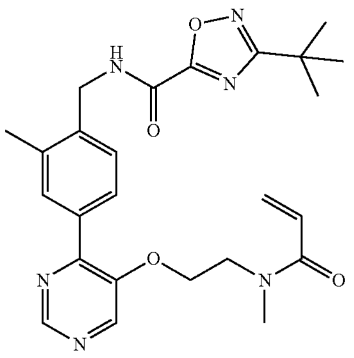 [SMILES: C=CC(=O)N(C)CCOc1cncnc1-c1ccc(CNC(=O)c2nc(C(C)(C)C)no2)c(C)c1] | ESI-MS $(M + H)^+$: 479.1 $^1H$ NMR: (400 MHz, DMSO-$d_6$) δ: 9.82 (s, 1H), 8.82 (d, J = 2.4 Hz, 1H), 8.66 (d, J = 6.8 Hz, 1H), 7.86-7.82 (m, 1H), 7.77-7.73 (m, 1H), 7.32-7.27 (m, 1H), 6.70-6.66 (m, 1H), 6.10-5.95 (m, 1H), 5.62-5.57 (m, 1H), 4.47 (d, J = 4.8 Hz, 2H), 4.33 (t, J = 5.2 Hz, 2H), 3.85-3.76 (m, 2H), 3.04-2.87 (m, 3H), 2.35 (s, 3H), 1.34 (s, 9H). |
| 29 | 1-(tert-butyl)-N-(2-methyl-4-(5-(2-(N-methylacrylamido)acetamido) pyrimidin-4-yl)benzyl)-1H-1,2,3-triazole-4-carboxamide | 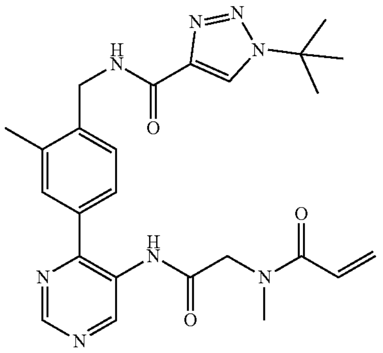 [SMILES: C=CC(=O)N(C)CC(=O)Nc1cncnc1-c1ccc(CNC(=O)c2cn(C(C)(C)C)nn2)c(C)c1] | MS $(M + H)^+$: 491.4 $^1H$ NMR: (500 MHz, DMSO-$d_6$) δ: 10.08-9.93 (m, 1H), 9.08-9.01 (m, 2H), 8.89-8.85 (m, 1H), 8.72 (s, 1H), 7.67-7.55 (m, 2H), 7.37 (d, J = 7.5 Hz, 1H), 6.83-6.76 (m, 1H), 6.16-5.61 (m, 2H), 4.51 (d, J = 6.0 Hz, 2H), 4.27-4.15 (m, 2H) 3.10-2.86 (m, 3H), 2.43 (s, 3H), 1.65 (s, 9H). |
| 30 | N-(4-(5-(2-acrylamidoacetamido) pyrimidin-4-yl)-2-methylbenzyl)-1-(tert-butyl)-1H-1,2,3-triazole-4-carboxamide | 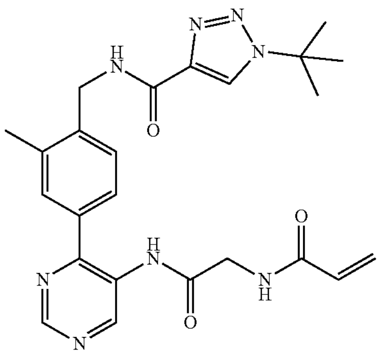 [SMILES: C=CC(=O)NCC(=O)Nc1cncnc1-c1ccc(CNC(=O)c2cn(C(C)(C)C)nn2)c(C)c1] | MS $(M + H)^+$: 477.1 $^1H$ NMR: (500 MHz, DMSO-$d_6$) δ: 9.94 (s, 1H), 9.06-9.01 (m, 2H), 8.88 (s, 1H), 8.72 (s, 1H), 8.52-8.49 (m, 1H), 7.65-7.60 (m, 2H), 7.35 (d, J = 8.0 Hz, 1H), 6.31-6.27 (m, 1H), 6.13-6.08 (m, 1H), 5.62-5.59 (m, 1H), 4.51 (d, J = 6.0 Hz, 2H), 3.95 (d, J = 5.5 Hz, 2H), 2.42 (s, 3H), 1.65 (s, 9H). |

Synthesis of Compounds of Formulas (IIB), (IIIB), (IIC), (IIIC), (IID) and (IIID)

Preparative HPLC Conditions

For Example 31-52, the following preparative HPLC methods were used:

Method A:
- Column: Welch Xtimate C18 150×25 mm×5 μm
- Mobile phase A: MeCN
- Mobile phase B: $H_2O$
- Modifier: 10 mM $NH_4HCO_3$
- Gradient (% organic): % optimised for each example
- Flow rate: 25 mL/min
- Gradient time: 10 min Method B:
- Column: Agela Durashell C18 150×25 mm, 5 μm
- Mobile phase A: MeCN
- Mobile phase B: $H_2O$
- Modifier: 0.04% $NH_4OH$+10 mM $NH_4HCO_3$
- Gradient (% organic): optimised for each example.
- Flow rate: 25 mL/min
- Gradient time: 10 min Method C:
- Column: YMC-Actus Triart C18 250×50 mm, 7 μm
- Mobile phase A: MeCN
- Mobile phase B: $H_2O$
- Modifier: 0.05% $NH_4OH$
- Gradient (% organic): optimised for each example.
- Flow rate: 30 mL/min Method D:
- Column: Waters XSelect CSH OBD C18 150×19 mm, 5 μm
- Mobile phase A: MeCN
- Mobile phase B: $H_2O$
- Modifier: $NH_3$
- Gradient (% organic): optimised for each example Method E:

Column: YMC-Actus Triart C18 50×30 mm, 5 μm
Mobile phase A: MeCN
Mobile phase B: $H_2O$
Modifier: 0.225% Formic acid
Gradient (% organic): optimised for each example.
Flow rate: 25 mL/min
Gradient time: 10 min Preparative SFC Conditions Method F:

Column: CHIRALPAK AS 30×250 mm, 10 μm
Mobile Phase B: 30% EtOH in $CO_2$
Flow rate: 60 mL/min
ABPR 120 bar, MBPR 40 psi, column temp 40° C.

Common Intermediates:

Intermediate 1: 1-(tert-butyl)-N-(2-methyl-4-(4,4,5,5-tetramethyl-1,3,2-dioxaborolan-2-yl)benzyl)-1H-1,2,3-triazole-4-carboxamide

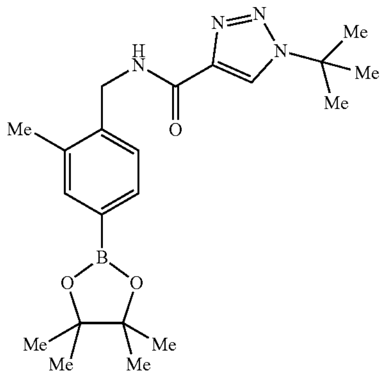 [SMILES: Cc1cc(B2OC(C)(C)C(C)(C)O2)ccc1CNC(=O)c1cn(C(C)(C)C)nn1]

1. Synthesis of N-(4-bromo-2-methylbenzyl)-1-(tert-butyl)-1H-1,2,3-triazole-4-carboxamide

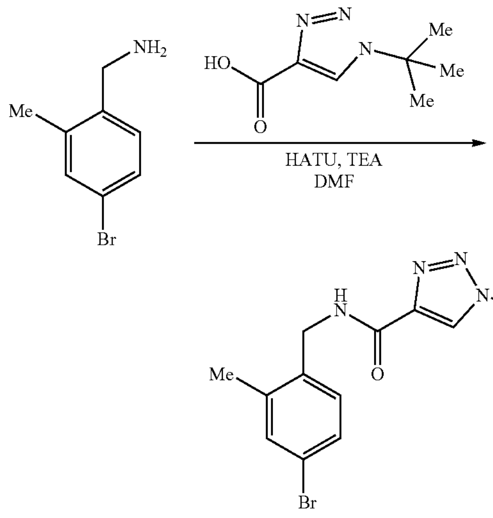

To a solution of 1-(tert-butyl)-1H-1,2,3-triazole-4-carboxylic acid (450.0 mg, 2.66 mmol), (4-bromo-2-methylphenyl)methanamine (585.4 mg, 2.93 mmol) and HATU (1.2 g, 3.19 mmol) in DMF (6.0 mL) was added TEA (1.1 mL, 7.98 mmol) and the reaction stirred at 25° C. for 2 h. The reaction was concentrated in vacuo and the residue extracted with EtOAc (20 mL×3). The combined organic layers were dried over $Na_2SO_4$, filtered and the filtrate concentrated in vacuo. The crude product was purified by silica gel chromatography eluting with PE/EtOAc (1/1 to 1/9) to give N-(4-bromo-2-methylbenzyl)-1-(tert-butyl)-1H-1,2,3-triazole-4-carboxamide (860.0 mg, 92.0% yield) as a white solid. LCMS m/z=352.8 $(M+H)^+$.

2. Synthesis of 1-(tert-butyl)-N-(2-methyl-4-(4,4,5,5-tetramethyl-1,3,2-dioxaborolan-2-yl)benzyl)-1H-1,2,3-triazole-4-carboxamide

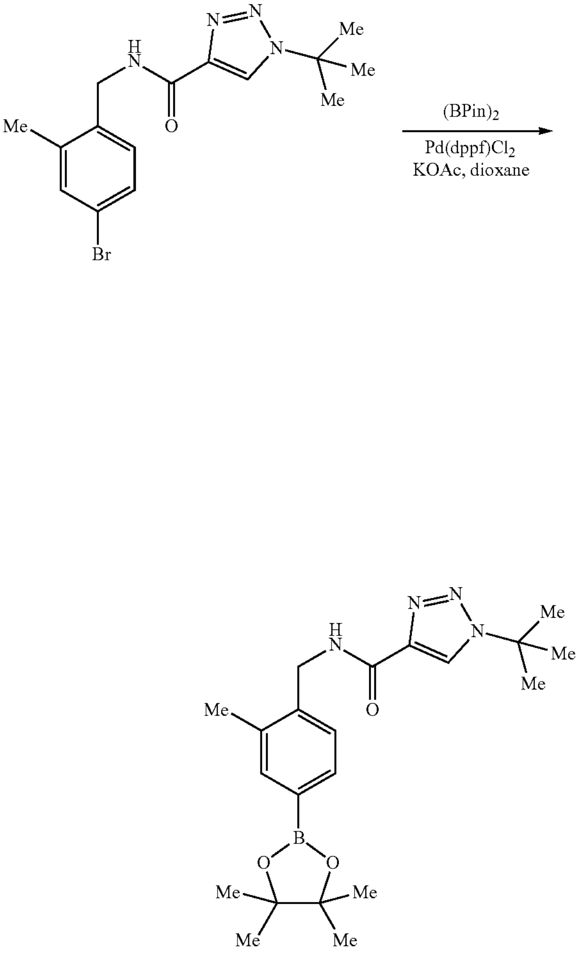

$N_2$ was bubbled through a suspension of N-(4-bromo-2-methylbenzyl)-1-(tert-butyl)-1H-1,2,3-triazole-4-carboxamide (860.0 mg, 2.45 mmol), $(BPin)_2$ (1.5 g, 6.13 mmol) and KOAc (601.1 mg, 6.13 mmol) in dioxane (20 mL). Pd(dppf)$Cl_2$ (179.2 mg, 0.245 mmol) was added and the reaction stirred at 90° C. for 2 h under $N_2$. The reaction mixture was concentrated in vacuo and the residue purified by silica gel chromatography eluting with PE/EtOAc (3/1) to give 1-(tert-butyl)-N-(2-methyl-4-(4,4,5,5-tetramethyl-1,3,2-dioxaborolan-2-yl)benzyl)-1H-1,2,3-triazole-4-carboxamide (900 mg, 92.2% yield) as a white solid. LCMS m/z=398.9 $(M+H)^+$.

Intermediate 2: 5-(tert-butyl)-N-(2-methyl-4-(4,4,5,5-tetramethyl-1,3,2-dioxaborolan-2-yl)benzyl)-1,2,4-oxadiazole-3-carboxamide

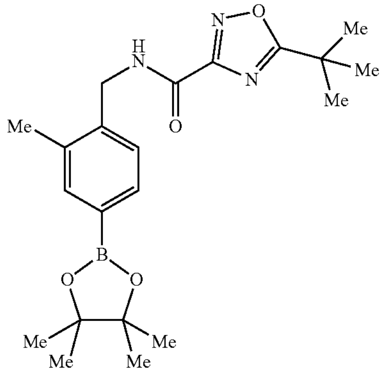 [SMILES: Cc1cc(B2OC(C)(C)C(C)(C)O2)ccc1CNC(=O)c1noc(C(C)(C)C)n1]

1. Synthesis of (2-methyl-4-(4,4,5,5-tetramethyl-1,3,2-dioxaborolan-2-yl)phenyl)methanamine hydrochloride

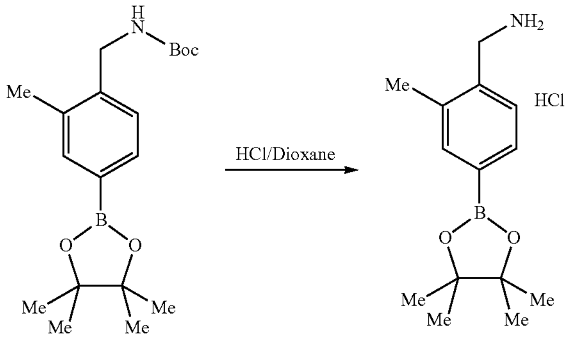 [SMILES: Cc1cc(B2OC(C)(C)C(C)(C)O2)ccc1CNC(=O)OC(C)(C)C ; "HCl/Dioxane" ; Cc1cc(B2OC(C)(C)C(C)(C)O2)ccc1CN ; Cl]

A solution of tert-butyl (2-methyl-4-(4,4,5,5-tetramethyl-1,3,2-dioxaborolan-2-yl)benzyl)carbamate (5.00 g, 14.4 mmol) in 4 M HCl/dioxane (100 mL) was stirred at 20° C. for 1 h. The mixture was evaporated under reduced pressure to give (2-methyl-4-(4,4,5,5-tetramethyl-1,3,2-dioxaborolan-2-yl)phenyl)methanamine hydrochloride as a light yellow solid (4.0 g, yield: 98%), which was carried forward without further purification.

2. Synthesis of 5-(tert-butyl)-N-(2-methyl-4-(4,4,5,5-tetramethyl-1,3,2-dioxaborolan-2-yl)benzyl)-1,2,4-oxadiazole-3-carboxamide

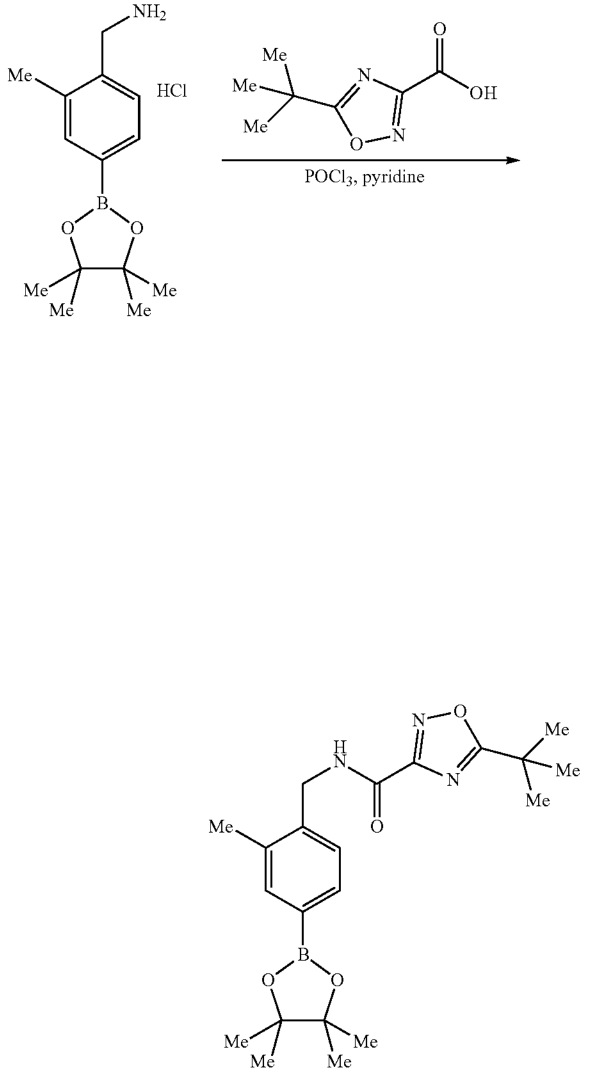

To a solution of (2-methyl-4-(4,4,5,5-tetramethyl-1,3,2-dioxaborolan-2-yl)phenyl)methanamine hydrochloride (3.33 g, 11.8 mmol) in DCM (20 mL) was added 5-(tert-butyl)-1,2,4-oxadiazole-3-carboxylic acid (2.00 g, 11.8 mmol) and the solution cooled to 0° C. $POCl_3$ (3.28 mL, 35.3 mmol) was added, followed by pyridine (5.69 mL, 70.5 mmol) and the reaction stirred at 20° C. for 1 h. The reaction was poured into sat. aq. $NaHCO_3$ solution (300 mL) and the mixture extracted with DCM (300 mL). The organic layer was washed with brine (200 mL), dried ($Na_2SO_4$), filtered, and concentrated in vacuo. The residue was purified by silica gel column chromatography eluting with PE/EtOAc (5/1 to 1/1) to give 5-(tert-butyl)-N-(2-methyl-4-(4,4,5,5-tetramethyl-1,3,2-dioxaborolan-2-yl)benzyl)-1,2,4-oxadiazole-3-carboxamide as a light yellow oil (3.4 g, yield: 73%). $^1H$ NMR (400 MHz $CDCl_3$) δ: 7.69-7.64 (m, 2H), 7.32 (d, 1H), 7.07 (br s, 1H), 4.68 (d, 2H), 2.38 (s, 3H), 1.46 (s, 9H), 1.35 (s, 12H).

Intermediate 3: 3-(tert-butyl)-N-(3-fluoro-2-methyl-4-(4,4,5,5-tetramethyl-1,3,2-dioxaborolan-2-yl)benzyl)-1,2,4-oxadiazole-5-carboxamide

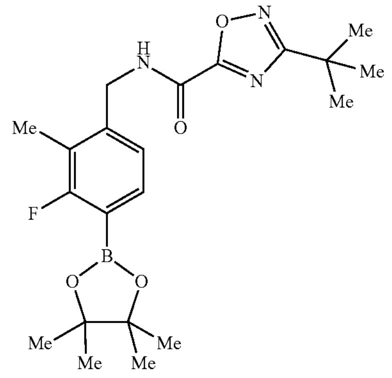 [SMILES: Cc1c(CNC(=O)c2nc(C(C)(C)C)no2)ccc(B2OC(C)(C)C(C)(C)O2)c1F]

1. Synthesis of 4-bromo-2-fluoro-3-methylaniline

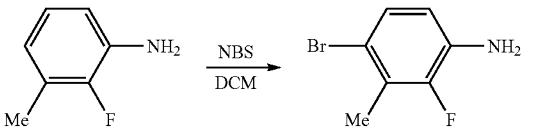

A solution of NBS (28.4 g, 160 mmol) in DCM was added dropwise to an ice-cooled solution of 2-fluoro-3-methylaniline (20.0 g, 160 mmol) in DCM (200 mL) and the reaction stirred at 20° C. for 5 h. The mixture was diluted with sat. aq. $Na_2CO_3$ solution (100 mL), the layers separated, and the aqueous phase was extracted with DCM (2×100 mL). The combined organic layers were dried ($Na_2SO_4$), filtered, and concentrated in vacuo. The crude product was purified by silica gel column chromatography eluting with PE/EtOAc (10/1) to give 4-bromo-2-fluoro-3-methylaniline as a brown oil (32.0 g, crude). LCMS m/z=205.8 (M+H)+

2. Synthesis of 4-amino-3-fluoro-2-methylbenzonitrile

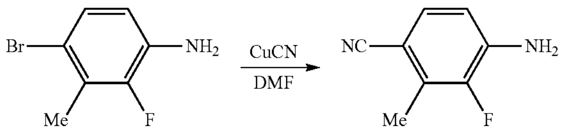

CuCN (35.6 g, 397 mmol) was added to a solution of 4-bromo-2-fluoro-3-methylaniline (27 g, 132 mmol) in DMF (200 mL) under $N_2$ and the reaction was stirred at 140° C. for 16 h. $NH_3$•$H_2O$ (300 mL) was added to the cooled reaction, the mixture filtered, the filtrate was poured into $H_2O$ (300 mL) and extracted with EtOAc (2×300 mL). The aqueous phase was extracted with EtOAc (2×300 mL) and the combined organic layers were dried ($Na_2SO_4$), filtered and concentrated in vacuo. The crude product was purified by silica gel column chromatography eluting with PE/EtOAc (70/30) to give 4-amino-3-fluoro-2-methylbenzonitrile as a brown oil (15 g, 75% yield). LCMS m/z=151.0 (M+H)+

3. Synthesis of 4-bromo-3-fluoro-2-methylbenzonitrile

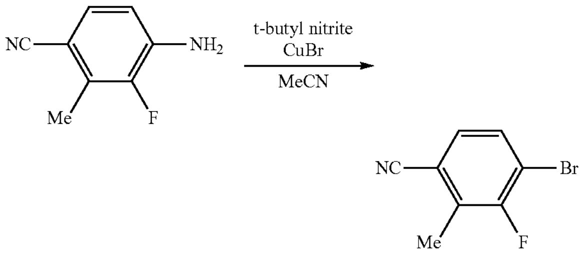

A solution of 4-amino-3-fluoro-2-methylbenzonitrile (15 g, 100 mmol) in MeCN (250 mL) was added to a solution of tert-butyl nitrite (17.8 mL, 150 mmol) and CuBr (21.5 g, 150 mmol) in MeCN at 65° C. and the reaction stirred at 65° C. for 3 h under $N_2$. The cooled mixture was filtered, the filtrate concentrated in vacuo and the crude product purified by silica gel column chromatography eluting with PE/EtOAc (9:1) to give 4-bromo-3-fluoro-2-methylbenzonitrile as an orange solid (11.5 g, crude). $^1H$ NMR (400 MHz, $CDCl_3$) δ: 7.51 (dd, 1H), 7.28 (dd, 1H), 2.52 (s, 3H).

4. Synthesis of tert-butyl (4-bromo-3-fluoro-2-methylbenzyl)carbamate

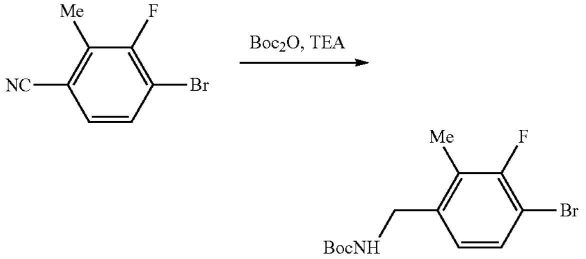

To a solution of (4-bromo-3-fluoro-2-methylphenyl)methanamine (14 g, 64 mmol) in DCM (100 mL) were added TEA (13 g, 128 mmol) and $Boc_2O$ (16.8 g, 77 mmol) and the mixture was stirred at 25° C. for 2 h. The mixture was concentrated in vacuo and the residue was purified by silica gel column chromatography PE/EtOAc (50/1) to give tert-butyl (4-bromo-3-fluoro-2-methylbenzyl)carbamate as a white solid (12.0 g, 59%). $^1H$ NMR (400 MHz, DMSO-$d_6$) δ: 7.47 (dd, 1H), 7.37 (dd, 1H), 6.96 (d, 1H), 4.07 (d, 2H), 2.19 (d, 3H), 1.37 (s, 9H).

5. Synthesis of tert-butyl (3-fluoro-2-methyl-4-(4,4,5,5-tetramethyl-1,3,2-dioxaborolan-2-yl)benzyl)carbamate

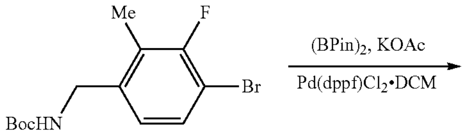

-continued

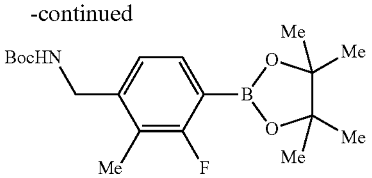

To a solution of tert-butyl (4-bromo-3-fluoro-2-methylbenzyl)carbamate (10 g, 31 mmol) in dioxane (150 mL) were added $(BPin)_2$ (9.6 g, 38 mmol) and KOAc (6.2 g, 63 mmol). $Pd(dppf)Cl_2$•DCM (2.1 g, 2.5 mmol) was added and the reaction was stirred at 80° C. for 17 h under $N_2$. The reaction mixture was concentrated in vacuo and the crude material was purified by silica-gel column chromatography eluting with PE/EtOAc (20:1) to give tert-butyl (3-fluoro-2-methyl-4-(4,4,5,5-tetramethyl-1,3,2-dioxaborolan-2-yl)benzyl)carbamate as a yellow solid (13.0 g, crude). LCMS m/z=310.1 (M-tBu+H)+

6. Synthesis of (3-fluoro-2-methyl-4-(4,4,5,5-tetramethyl-1,3,2-dioxaborolan-2-yl)phenyl)methanamine hydrochloride

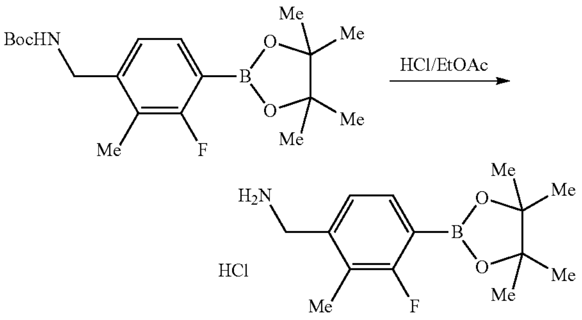

To a solution of tert-butyl (3-fluoro-2-methyl-4-(4,4,5,5-tetramethyl-1,3,2-dioxaborolan-2-yl)benzylcarbamate (7.0 g, 19.16 mmol) in EtOAc (10 mL) and MeOH (5 mL) was slowly added HCl (4 M, 13.15 mL) and the reaction stirred at 15° C. for 4 h. The mixture was evaporated under reduced pressure to give (3-fluoro-2-methyl-4-(4,4,5,5-tetramethyl-1,3,2-dioxaborolan-2-yl)phenyl)methanamine hydrochloride (6.0 g, crude) as a yellow solid.

LCMS m/z=266.2 $(M+H)^+$.

7. Synthesis of 5-(tert-butyl)-N-(3-fluoro-2-methyl-4-(4,4,5,5-tetramethyl-1,3,2-dioxaborolan-2-yl)benzyl)-1,2,4-oxadiazole-3-carboxamide

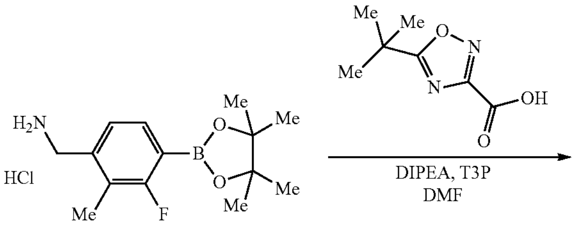

-continued

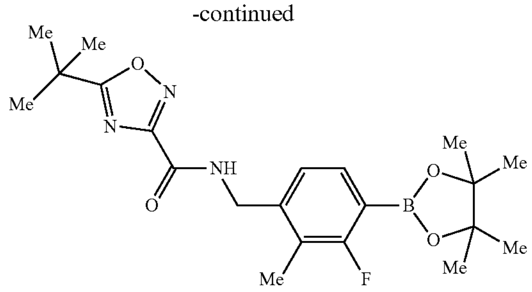

DIPEA (2.73 g, 21.15 mmol, 3.69 mL) was added to a suspension of (3-fluoro-2-methyl-4-(4,4,5,5-tetramethyl-1,3,2-dioxaborolan-2-yl)phenyl)methanamine hydrochloride (3.19 g, 10.58 mmol) and 5-(tert-butyl)-1,2,4-oxadiazole-3-carboxylic acid (1.50 g, 7.05 mmol) in anhydrous DMF (20 mL) and the mixture cooled to 0° C. T3P (5.83 g, 9.16 mmol, 50% purity) was added, the cooling bath removed and the reaction stirred at 15° C. for 2 h. The reaction was quenched with water (30 mL) and then EtOAc (30 mL) added. The layers were separated and the aqueous layer extracted with EtOAc (40 mL). The combined organic layers were washed with water (50 mL), sat. aq. solution of $NaHCO_3$ (50 mL) and brine (50 mL). The organic layer was dried over $Na_2SO_4$, filtered and concentrated in vacuo to give a beige oil. This was purified by silica gel column chromatography (PE/EtOAc, 100/0 to 65/35) to give 5-(tert-butyl)-N-(3-fluoro-2-methyl-4-(4,4,5,5-tetramethyl-1,3,2-dioxaborolan-2-yl)benzyl)-1,2,4-oxadiazole-3-carboxamide (600 mg, 20.40% yield) as a thick pale-yellow oil, which solidified upon standing. LCMS m/z=417.9 $(M+H)^+$.

Intermediate 4: N-methyl-N-(2-methyl-4-(4,4,5,5-tetramethyl-1,3,2-dioxaborolan-2-yl)benzyl)-6-(trifluoromethyl)nicotinamide 1. Synthesis of N-(4-bromo-2-methylbenzyl)-N-methyl-6-(trifluoromethyl)nicotinamide A mixture of 1-(4-bromo-2-methyl-phenyl)-N-methyl-methanamine (300 mg, 1.40 mmol), 6-(trifluoromethyl)pyridine-3-carboxylic acid (267.79 mg, 1.40 mmol), HATU (1.07 g, 2.80 mmol) and DIPEA (542.81 mg, 4.20 mmol) in DCM (5 mL) was stirred at rt for 16 h. The reaction was filtered through Celite® and washed with DCM. The filtrate was concentrated in vacuo and the residue purified by silica gel column chromatography eluting with heptanes/EtOAc (100/0 to 1/1) to give N-(4-bromo-2-methylbenzyl)-N-methyl-6-(trifluoromethyl)nicotinamide (527 mg, 92.36% yield) as a white solid. LCMS m/z=389.0 (M+H)+

2. Synthesis of N-methyl-N-(2-methyl-4-(4,4,5,5-tetramethyl-1,3,2-dioxaborolan-2-yl)benzyl)-6-(trifluoromethyl)nicotinamide A mixture of N-(4-bromo-2-methylbenzyl)-N-methyl-6-(trifluoromethyl)nicotinamide (527 mg, 1.36 mmol), $(BPin)_2$ (345.63 mg, 1.36 mmol), KOAc (400.73 mg, 4.08 mmol) and Pd(dppf)C12:DCM (111.15 mg, 136.11 μmol) in dioxane (5 mL) was degassed and heated at 95 □C for 16 h. The cooled mixture was diluted with EtOAc and filtered through Celite®. The filtrate was concentrated in vacuo and the residue purified by silica gel column chromatography eluting with heptanes/EtOAc (100/0 to 0/100) to give N-methyl-N-(2-methyl-4-(4,4,5,5-tetramethyl-1,3,2-dioxaborolan-2-yl)benzyl)-6-(trifluoromethyl)nicotinamide (523 mg, 88.55% yield) as a gel. LCMS m/z=435.2 (M+H)+

Example 31. (R)-N-(4-(3-(1-acryloylpiperidine-2-carboxamido)pyridin-4-yl)-2-methylbenzyl)-5-(tert-butyl)-1,2,4-oxadiazole-3-carboxamide

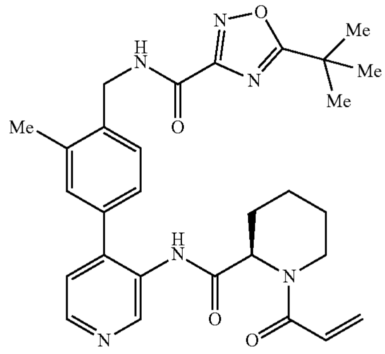 [SMILES: C=CC(=O)N1CCCC[C@@H]1C(=O)Nc1cnccc1-c1ccc(CNC(=O)c2noc(C(C)(C)C)n2)c(C)c1]

1. Synthesis of N-(4-(3-aminopyridin-4-yl)-2-methylbenzyl)-5-(tert-butyl)-1,2,4-oxadiazole-3-carboxamide

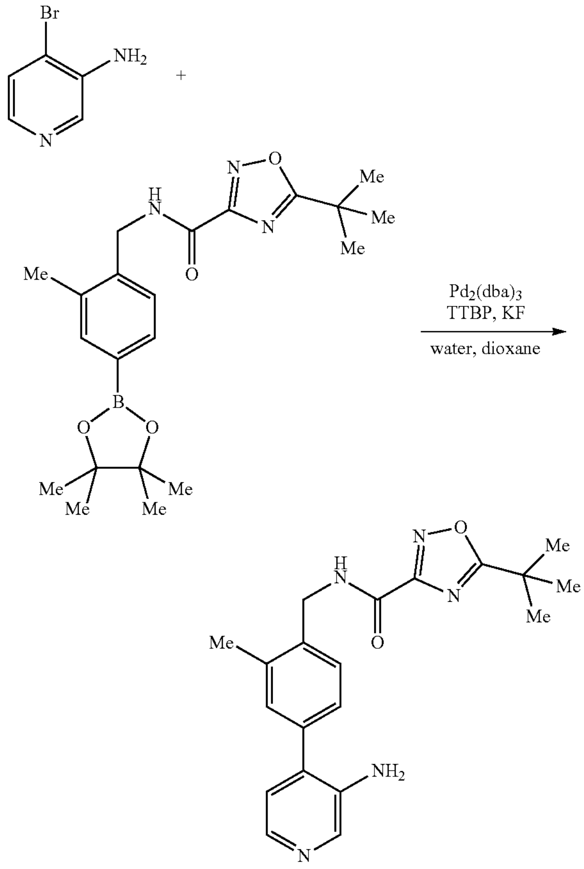

A mixture of 4-bromopyridin-3-amine (300 mg, 1.73 mmol), Intermediate 2: 5-(tert-butyl)-N-(2-methyl-4-(4,4,5,5-tetramethyl-1,3,2-dioxaborolan-2-yl)benzyl)-1,2,4-oxadiazole-3-carboxamide (1.04 g, 2.60 mmol), $Pd_2(dba)_3$ (79.21 mg, 86.50 μmol), TTBP (50.19 mg, 173.0 μmol) and KF (301.54 mg, 5.19 mmol) in water (999.53 μL) and dioxane (6 mL) was degassed with $N_2$ and heated at 100° C. for 16 h. The cooled mixture was filtered through Celite®, the filtrate concentrated in vacuo and the residue purified by column chromatography on silica gel eluting with DCM/MeOH (100/0 to 95/5) to give N-(4-(3-aminopyridin-4-yl)-2-methylbenzyl)-5-(tert-butyl)-1,2,4-oxadiazole-3-carboxamide (141 mg, 22.30% yield) LCMS m/z=366.2 (M+H)+

2. Synthesis of tert-butyl (R)-2-((4-(4-((5-(tert-butyl)-1,2,4-oxadiazole-3-carboxamido)methyl)-3-methylphenyl)pyridin-3-yl)carbamoyl)piperidine-1-carboxylate

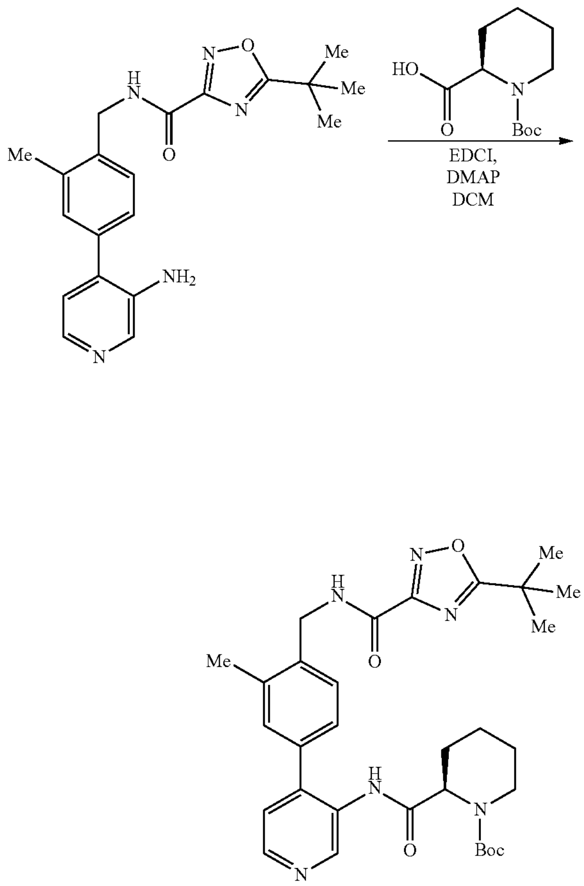 [SMILES: Cc1cc(-c2ccncc2N)ccc1CNC(=O)c1noc(C(C)(C)C)n1 ; CC(C)(C)OC(=O)N1CCCC[C@@H]1C(=O)O ; Cc1cc(-c2ccncc2NC(=O)[C@H]2CCCCN2C(=O)OC(C)(C)C)ccc1CNC(=O)c1noc(C(C)(C)C)n1]

A solution of N-(4-(3-aminopyridin-4-yl)-2-methylbenzyl)-5-(tert-butyl)-1,2,4-oxadiazole-3-carboxamide (141 mg, 385.85 μmol), (2R)-1-(tert-butoxycarbonyl)piperidine-2-carboxylic acid (88.46 mg, 385.85 μmol), DMAP (61.28 mg, 501.60 μmol) and EDC (96.16 mg, 501.60 μmol) in DCM (2 mL) was stirred at rt for 6 h. The solution was loaded onto silica gel column and washed with heptanes/EtOAc (100/0 to 0/100) to give tert-butyl (R)-2-((4-(4-((5-(tert-butyl)-1,2,4-oxadiazole-3-carboxamido)methyl)-3-methylphenyl)pyridin-3-yl)carbamoyl)piperidine-1-carboxylate (162.10 mg, 72.85% yield) as a white solid. LCMS m/z=577.4 (M+H)+

3. Synthesis of (R)-5-(tert-butyl)-N-(2-methyl-4-(3-(piperidine-2-carboxamido)pyridin-4-yl)benzyl)-1,2,4-oxadiazole-3-carboxamide hydrochloride

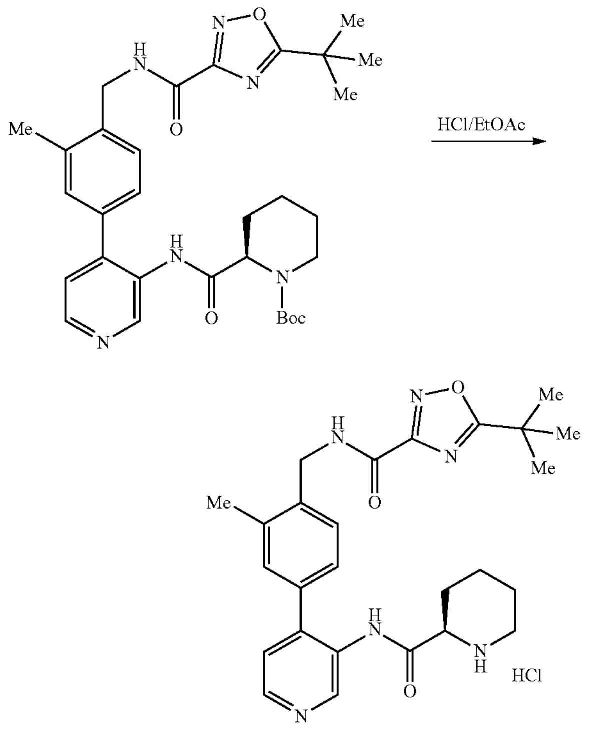

A solution of tert-butyl (R)-2-((4-(4-((5-(tert-butyl)-1,2,4-oxadiazole-3-carboxamido)methyl)-3-methylphenyl)pyridin-3-yl)carbamoyl)piperidine-1-carboxylate (161 mg, 279.18 μmol) in EtOAc (4 mL) and HCl (4 M, 697.95 μL) was stirred at rt for 16 h. The solution was evaporated under reduced pressure to give (R)-5-(tert-butyl)-N-(2-methyl-4-(3-(piperidine-2-carboxamido)pyridin-4-yl)benzyl)-1,2,4-oxadiazole-3-carboxamide hydrochloride as a light yellow solid. LCMS m/z=477.3 (M+H)+

4. Synthesis of (R)-N-(4-(3-(1-acryloylpiperidine-2-carboxamido)pyridin-4-yl)-2-methylbenzyl)-5-(tert-butyl)-1,2,4-oxadiazole-3-carboxamide

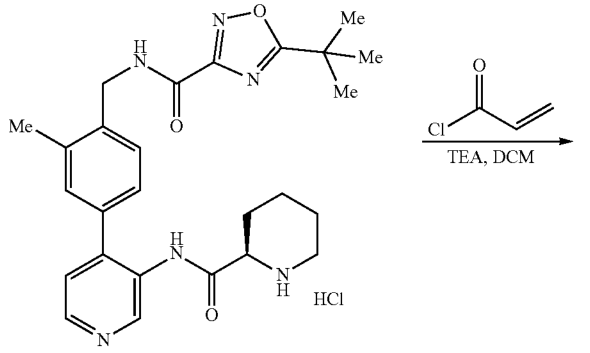

-continued

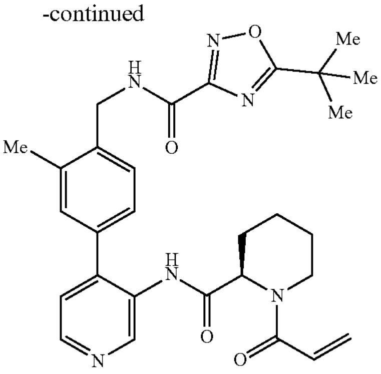

TEA (59.57 mg, 588.66 μmol) was added to (R)-5-(tert-butyl)-N-(2-methyl-4-(3-(piperidine-2-carboxamido)pyridin-4-yl)benzyl)-1,2,4-oxadiazole-3-carboxamide hydrochloride (151 mg, 294.33 μmol) in DCM (8 mL) and the mixture stirred until solution was obtained. After cooling to 0° C., acryloyl chloride (31.97 mg, 353.20 μmol) was added and the reaction stirred for 5 min. Sat. aq. $NaHCO_3$ (10 mL) was added and the mixture extracted with DCM. The combined organic extracts were dried over $Na_2SO_4$ and concentrated in vacuo. The residue was purified by silica gel column chromatography eluting with EtOAc/MeOH (100/0 to 95/5) to give (R)-N-(4-(3-(1-acryloylpiperidine-2-carboxamido)pyridin-4-yl)-2-methylbenzyl)-5-(tert-butyl)-1,2,4-oxadiazole-3-carboxamide (58.00 mg, 35.28% yield) as a colorless glass. LCMS m/z=531.4 (M+H)+. $^1$H NMR (400 MHz, $CDCl_3$) δ: 9.74-9.36 (m, 1H), 8.48-8.36 (m, 1H), 8.08-7.72 (m, 1H), 7.39 (d, 1H), 7.23-6.96 (m, 3H), 6.47-6.33 (m, 1H), 6.23-6.09 (m, 1H), 5.76-5.60 (m, 1H), 5.28-5.18 (m, 1H), 4.81-4.60 (m, 2H), 4.55-4.31 (m, 1H), 3.84-3.69 (m, 1H), 2.94-2.81 (m, 1H), 2.41 (s, 3H), 2.37-2.18 (m, 1H), 1.82-1.56 (m, 3H), 1.47 (s, 9H), 1.42-1.33 (m, 1H).

Example 32. (S)-N-(4-(3-(1-acryloylpiperidine-2-carboxamido)pyridin-4-yl)-2-methylbenzyl)-5-(tert-butyl)-1,2,4-oxadiazole-3-carboxamide

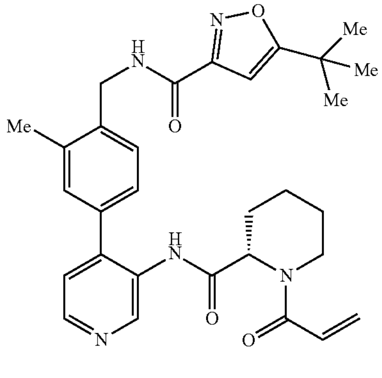 [SMILES: C=CC(=O)N1CCCC[C@H]1C(=O)Nc1cnccc1-c1ccc(CNC(=O)c2cc(C(C)(C)C)on2)c(C)c1]

(S)-N-(4-(3-(1-acryloylpiperidine-2-carboxamido)pyridin-4-yl)-2-methylbenzyl)-5-(tert-butyl)-1,2,4-oxadiazole-3-carboxamide was obtained as a colorless glass, from N-(4-(3-aminopyridin-4-yl)-2-methylbenzyl)-5-(tert-butyl)-1,2,4-oxadiazole-3-carboxamide and (2S)-1-(tert-butoxycarbonyl)piperidine-2-carboxylic acid following the steps described in Example 31, 20.5 mg, 36.2% yield. LCMS m/z=531.4 (M+H)+. 1H NMR (400 MHz, $CDCl_3$) δ: 9.78-9.37 (m, 1H), 8.51-8.37 (m, 1H), 8.12-7.69 (m, 1H), 7.44-

7.36 (m, 1H), 7.23-6.93 (m, 3H), 6.46-6.35 (m, 1H), 6.24-6.09 (m, 1H), 5.78-5.61 (m, 1H), 5.29-5.20 (m, 1H), 4.84-4.61 (m, 2H), 4.55-4.30 (m, 1H), 3.85-3.67 (m, 1H), 2.93-2.78 (m, 1H), 2.44-2.38 (m, 3H), 2.36-2.19 (m, 1H), 1.80-1.56 (m, 3H), 1.48 (s, 9H), 1.43-1.33 (m, 1H).

Example 33. N-(4-(3-((1-acryloylazetidin-3-yl)oxy)pyridin-4-yl)-2-methylbenzyl)-1-(tert-butyl)-1H-1,2,3-triazole-4-carboxamide

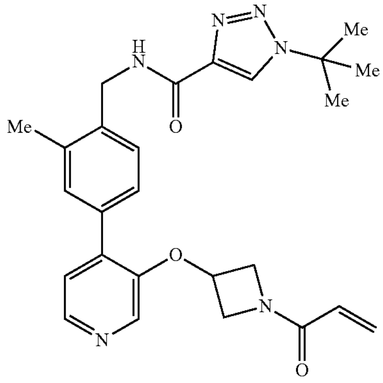 [SMILES: C=CC(=O)N1CC(Oc2cnccc2-c2ccc(CNC(=O)c3cn(C(C)(C)C)nn3)c(C)c2)C1]

1. Synthesis of tert-butyl 3-((4-chloropyridin-3-yl)oxy)azetidine-1-carboxylate

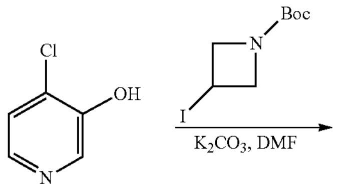

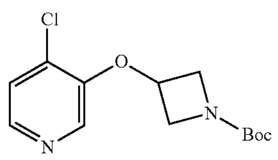

A mixture of 4-chloropyridin-3-ol (2.0 g, 15.44 mmol), tert-butyl 3-iodoazetidine-1-carboxylate (5.2 g, 18.53 mmol) and $K_2CO_3$ (4.2 g, 30.88 mmol) in DMF (20 mL) was stirred at 80° C. for 2 h. The mixture was concentrated in vacuo and the residue was purified by silica gel column chromatography eluting with EtOAc to give tert-butyl 3-((4-chloropyridin-3-yl)oxy)azetidine-1-carboxylate (3.7 g, 84.1% yield) as a yellow oil. LCMS m/z=285.1 (M+H)+

2. Synthesis of tert-butyl 3-((4-(4-((1-(tert-butyl)-1H-1,2,3-triazole-4-carboxamido)methyl)-3-methylphenyl)pyridin-3-yl)oxy)azetidine-1-carboxylate

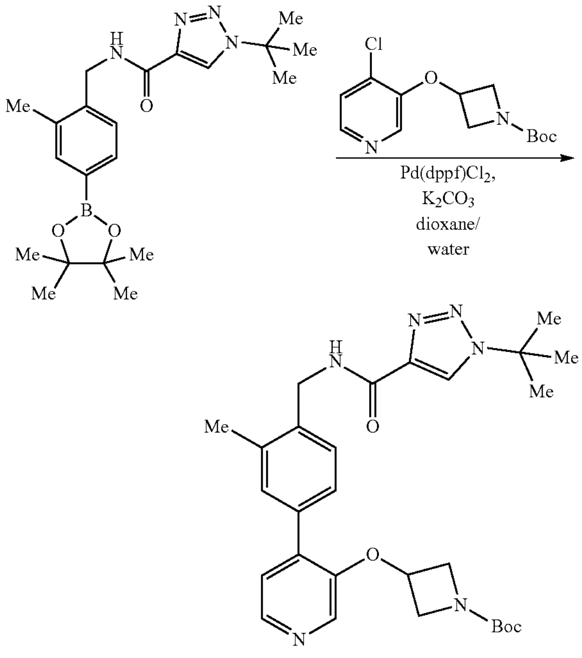

$N_2$ was bubbled through a suspension of Intermediate 1: 1-(tert-butyl)-N-(2-methyl-4-(4,4,5,5-tetramethyl-1,3,2-dioxaborolan-2-yl)benzyl)-1H-1,2,3-triazole-4-carboxamide (50.0 mg, 0.125 mmol), tert-butyl 3-((4-chloropyridin-3-yl)oxy)azetidine-1-carboxylate (42.8 mg, 0.151 mmol) and $K_2CO_3$ (43.3 mg, 0.313 mmol) in dioxane (2 mL) and water (0.5 mL). Pd(dppf)$Cl_2$ (9.19 mg, 0.012 mmol) was added and the reaction stirred at 90° C. for 16 h under $N_2$. The mixture was concentrated in vacuo and the residue was purified by silica gel column chromatography eluting with EtOAc to give tert-butyl 3-((4-(4-((1-(tert-butyl)-1H-1,2,3-triazole-4-carboxamido)methyl)-3-methylphenyl)pyridin-3-yl)oxy)azetidine-1-carboxylate (30.0 mg, 45.9% yield) as a yellow solid. LCMS m/z=521.1 (M+H)+.

3. Synthesis of N-(4-(3-(azetidin-3-yloxy)pyridin-4-yl)-2-methylbenzyl)-1-(tert-butyl)-1H-1,2,3-triazole-4-carboxamide hydrochloride

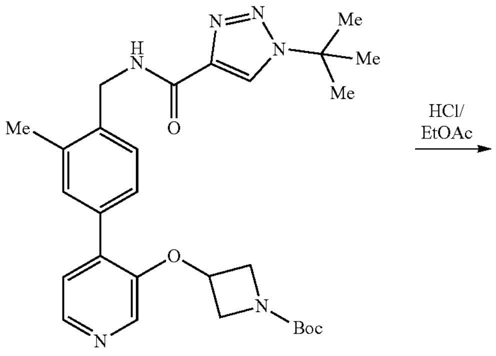

-continued

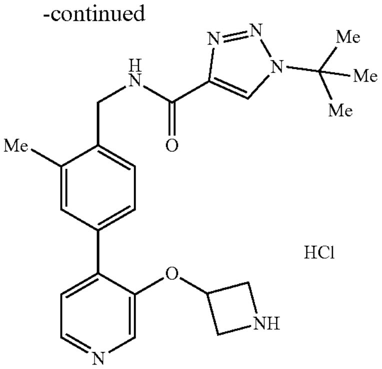

A solution of tert-butyl 3-((4-(4-((1-(tert-butyl)-1H-1,2,3-triazole-4-carboxamido)methyl)-3-methylphenyl)pyridin-3-yl)oxy)azetidine-1-carboxylate (30.0 mg, 0.057 mmol) in HCl/EtOAc (4 M, 10 mL) was stirred at 25° C. for 2 h. The mixture was evaporated under reduced pressure to give N-(4-(3-(azetidin-3-yloxy)pyridin-4-yl)-2-methylbenzyl)-1-(tert-butyl)-1H-1,2,3-triazole-4-carboxamide hydrochloride (30.0 mg, crude) as a white solid. $^1$H NMR (500 MHz, MeOD-$d_4$) δ: 8.61 (d, 1H), 8.56 (s, 1H), 8.49 (s, 1H), 8.10 (d, 1H), 7.69-7.63 (m, 2H), 7.53 (d, 1H), 5.42 (s, 1H), 4.68 (s, 2H), 4.64 (dd, 2H), 4.24 (dd, 2H), 2.51 (s, 3H), 1.72 (s, 9H).

4. Synthesis of N-(4-(3-((1-acryloylazetidin-3-yl)oxy)pyridin-4-yl)-2-methylbenzyl)-1-(tert-butyl)-1H-1,2,3-triazole-4-carboxamide

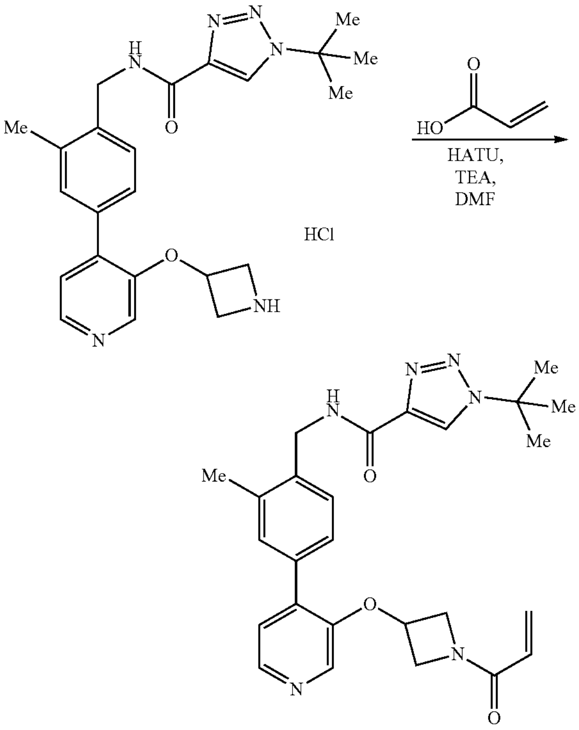

HATU (41.0 mg, 0.107 mmol) was added to a solution of N-(4-(3-(azetidin-3-yloxy)pyridin-4-yl)-2-methylbenzyl)-1-(tert-butyl)-1H-1,2,3-triazole-4-carboxamide hydrochloride (30.0 mg, 0.071 mmol), acrylic acid (5.6 mg, 0.078 mmol) and TEA (37.0 mg, 0.366 mmol) in DMF (1.0 mL) and the reaction stirred at 25° C. for 3 h. The mixture was concentrated in vacuo and the residue was purified by prep-HPLC (Method E, organic gradient 20-45%) and was further purified by prep HPLC (Method A, organic gradient 31-61%) to give N-(4-(3-((1-acryloylazetidin-3-yl)oxy)pyridin-4-yl)-2-methylbenzyl)-1-(tert-butyl)-1H-1,2,3-triazole-4-carboxamide (4.0 mg, 11.8% yield) as a white solid. LCMS m/z=475.1 (M+H)+. $^1$H NMR (500 MHz, MeOD-$d_4$) δ: 8.48 (s, 1H), 8.29 (d, 1H), 8.11 (s, 1H), 7.49-7.38 (m, 4H), 6.37-6.21 (m, 2H), 5.74 (dd, 1H), 5.19 (s, 1H), 4.73-4.69 (m, 1H), 4.65 (s, 2H), 4.47 (dd, 1H), 4.27 (d, 1H), 4.01 (d, 1H), 2.45 (s, 3H), 1.71 (s, 9H).

Example 34. N-(4-(3-((1-acryloylpyrrolidin-3-yl)oxy)pyridin-4-yl)-2-methylbenzyl)-1-(tert-butyl)-1H-1,2,3-triazole-4-carboxamide

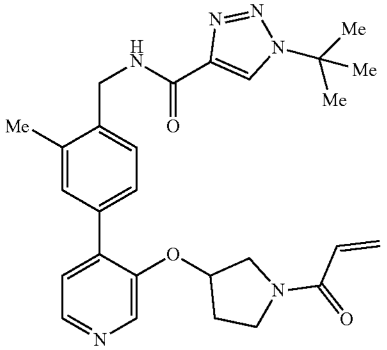 [SMILES: C=CC(=O)N1CCC(Oc2cnccc2-c2ccc(CNC(=O)c3cn(C(C)(C)C)nn3)c(C)c2)C1]

1. Synthesis of tert-butyl 3-((4-chloropyridin-3-yl)oxy)pyrrolidine-1-carboxylate

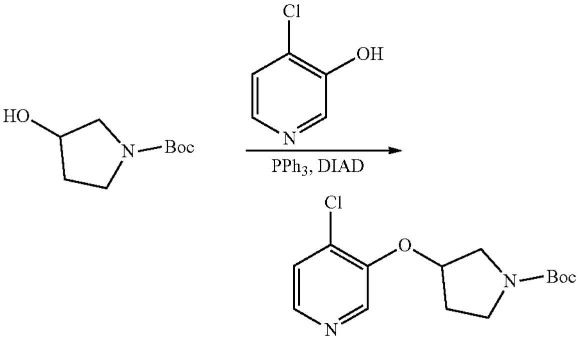

A solution of $PPh_3$ (4.0 g, 15.44 mmol) in THF (10 mL) was added dropwise to a solution of DIAD (3.1 g, 15.44 mmol) in THF (20 mL) cooled to 0° C. under $N_2$ and after complete addition the reaction was stirred at 0° C. for 10 min. This was added to a suspension of 4-chloropyridin-3-ol (1.0 g, 7.72 mmol) and tert-butyl 3-hydroxypyrrolidine-1-carboxylate (1.6 g, 8.49 mmol) in THF (10 mL) and the reaction mixture was stirred at 25° C. for 5 h under $N_2$. The mixture was concentrated in vacuo and the residue purified by silica gel column chromatography eluting with PE/EtOAc (1/1) and further purified by prep-HPLC (Method C, organic gradient 36-76%) to give tert-butyl 3-((4-chloropyridin-3-yl)oxy)pyrrolidine-1-carboxylate (1.4 g, 60.7% yield) as a white solid. LCMS m/z=242.9 (M-t-Bu)+

2. Synthesis of N-(4-(3-((1-acryloylpyrrolidin-3-yl)oxy)pyridin-4-yl)-2-methylbenzyl)-1-(tert-butyl)-1H-1,2,3-triazole-4-carboxamide

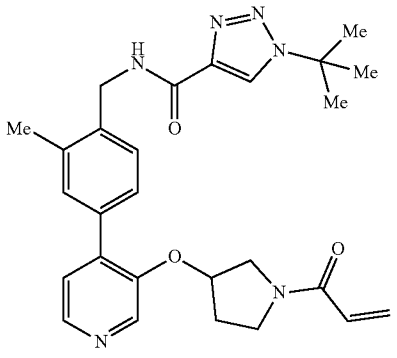 [SMILES: C=CC(=O)N1CCC(Oc2cnccc2-c2ccc(CNC(=O)c3cn(C(C)(C)C)nn3)c(C)c2)C1]

The compound was obtained from tert-butyl 3-((4-chloropyridin-3-yl)oxy)pyrrolidine-1-carboxylate and Intermediate 1: 1-(tert-butyl)-N-(2-methyl-4-(4,4,5,5-tetramethyl-1,3,2-dioxaborolan-2-yl)benzyl)-1H-1,2,3-triazole-4-carboxamide a similar procedure to that described in Example 33, steps 2 to 4. The crude was purified by prep HPLC (Method E, organic gradient 32-62%) to give N-(4-(3-((1-acryloylpyrrolidin-3-yl)oxy)pyridin-4-yl)-2-methylbenzyl)-1-(tert-butyl)-1H-1,2,3-triazole-4-carboxamide (9.0 mg, 16.0% yield) as a white solid. LCMS m/z=489.1 (M+H)+. $^{1}H$ NMR (500 MHz, MeOD-$d_4$) δ: 8.54-8.39 (m, 2H), 8.28 (t, 1H), 7.47-7.31 (m, 4H), 6.49-6.33 (m, 1H), 6.23-6.14 (m, 1H), 5.73-5.62 (m, 1H), 5.14 (br s, 1H), 4.61 (d, 2H), 3.79-3.66 (m, 2H), 3.54-3.33 (m, 2H), 2.38 (s, 3H), 2.26-2.07 (m, 2H), 1.71 (d, 9H).

Example 35 and 36. (R)-N-(4-(3-((1-acryloylpyrrolidin-3-yl)oxy)pyridin-4-yl)-2-methylbenzyl)-1-(tert-butyl)-1H-1,2,3-triazole-4-carboxamide and (S)-N-(4-(3-((1-acryloylpyrrolidin-3-yl)oxy)pyridin-4-yl)-2-methylbenzyl)-1-(tert-butyl)-1H-1,2,3-triazole-4-carboxamide

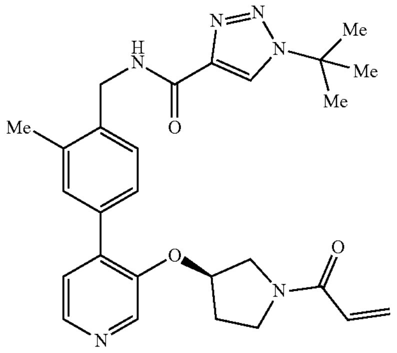

-continued

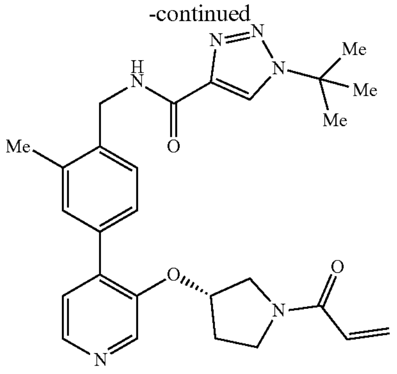

Stereochemistry Arbitrarily Assigned

Example 34, N-(4-(3-((1-acryloylpyrrolidin-3-yl)oxy)pyridin-4-yl)-2-methylbenzyl)-1-(tert-butyl)-1H-1,2,3-triazole-4-carboxamide (70.0 mg, 0.143 mmol) was separated by SFC (Method F) to give Example 35, (R)-N-(4-(3-((1-acryloylpyrrolidin-3-yl)oxy)pyridin-4-yl)-2-methylbenzyl)-1-(tert-butyl)-1H-1,2,3-triazole-4-carboxamide, (31.0 mg, 44.3% yield) as a white solid. LCMS m/z=489.1 (M+H)+. $^{1}H$ NMR (500 MHz, MeOD-$d_4$) δ: 8.54-8.41 (m, 2H), 8.28 (t, 1H), 7.47-7.32 (m, 4H), 6.49-6.34 (m, 1H), 6.24-6.15 (m, 1H), 5.70-5.67 (m, 1H), 5.14 (s, 1H), 4.64-4.58 (m, 2H), 3.78-3.39 (m, 4H), 2.38 (s, 3H), 2.26-2.09 (m, 2H), 1.71 (d, 9H).

Rf=3.062 min [Chiralpak AS-3 100×4.6 mm, 3 μm, Mobile phase: A: $CO_2$ B: EtOH (0.05% DEA), Gradient: from 5% to 40% of B in 4 min. Flow rate: 2.8 mL/min, Column temp: 35° C.]. Further elution provided Example 36, (S)-N-(4-(3-((1-acryloylpyrrolidin-3-yl)oxy)pyridin-4-yl)-2-methylbenzyl)-1-(tert-butyl)-1H-1,2,3-triazole-4-carboxamide, 31.0 mg, 44.3% yield as a white solid. LCMS m/z=489.1 (M+H)+. $^{1}H$ NMR (500 MHz, MeOD-$d_4$) δ: 8.55-8.42 (m, 2H), 8.28 (t, 1H), 7.48-7.32 (m, 4H), 6.51-6.34 (m, 1H), 6.24-6.15 (m, 1H), 5.70-5.68 (m, 1H), 5.15 (d, 1H), 4.64-4.59 (m, 2H), 3.78-3.39 (m, 4H), 2.39 (s, 3H), 2.28-2.07 (m, 2H), 1.71 (d, 9H).

Rf=3.198 min [Chiralpak AS-3 100×4.6 mm, 3 μm, Mobile phase: A: $CO_2$ B: EtOH (0.05% DEA), Gradient: from 5% to 40% of B in 4 min. Flow rate: 2.8 mL/min, Column temp: 35° C.

Example 37. N-(4-(3-((1-acryloylpiperidin-4-yl)oxy)pyridin-4-yl)-2-methylbenzyl)-1-(tert-butyl)-1H-1,2,3-triazole-4-carboxamide

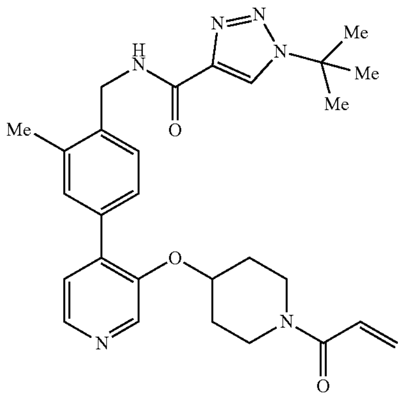 [SMILES: C=CC(=O)N1CCC(Oc2cnccc2-c2ccc(CNC(=O)c3cn(C(C)(C)C)nn3)c(C)c2)CC1]

The compound was obtained from 4-chloropyridin-3-ol, tert-butyl 4-bromopiperidine-1-carboxylate and Intermediate 1: Intermediate 1: 1-(tert-butyl)-N-(2-methyl-4-(4,4,5,5-tetramethyl-1,3,2-dioxaborolan-2-yl)benzyl)-1H-1,2,3-triazole-4-carboxamide following the steps described in Example 33. The crude final product was purified by prep-HPLC (Method E, organic gradient 25-45%) to give N-(4-(3-((1-acryloylpiperidin-4-yl)oxy)pyridin-4-yl)-2-methylbenzyl)-1-(tert-butyl)-1H-1,2,3-triazole-4-carboxamide (15.0 mg, 14.7% yield) as a white solid. LCMS m/z=503.2 (M+H)+. $^1$H NMR (500 MHz, MeOD-$d_4$) δ: 8.49-8.41 (m, 2H), 8.26 (d, 1H), 7.51-7.38 (m, 4H), 6.72 (dd, 1H), 6.16 (dd, 1H), 5.71 (dd, 1H), 4.77-4.72 (m, 1H), 4.67-4.62 (m, 2H), 3.75-3.64 (m, 1H), 3.61-3.45 (m, 3H), 2.45 (s, 3H), 2.02-1.90 (m, 2H), 1.80-1.73 (m, 2H), 1.71 (s, 9H).

Example 38. N-(4-(3-((1-acryloylpiperidin-3-yl)oxy)pyridin-4-yl)-2-methylbenzyl)-1-(tert-butyl)-1H-1,2,3-triazole-4-carboxamide

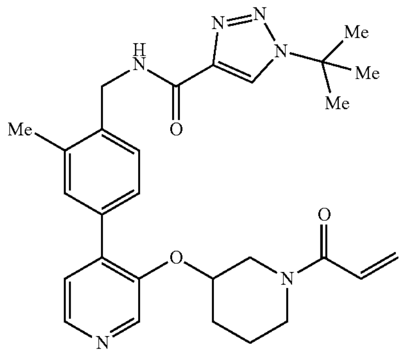

1. Synthesis of tert-butyl 3-((4-chloropyridin-3-yl)oxy)piperidine-1-carboxylate

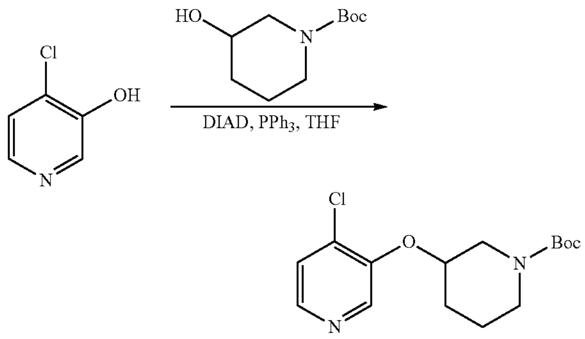

To a solution of 4-chloropyridin-3-ol (200 mg, 1.54 mmol), tert-butyl 3-hydroxypiperidine-1-carboxylate (371.93 mg, 1.85 mmol) and $PPh_3$ (525.08 mg, 2.0 mmol) in THF (20 mL) was added DIAD (622.81 mg, 3.08 mmol) dropwise under $N_2$ and the reaction was stirred at 28° C. for 16 h. Water (20 mL) was added, the mixture extracted with EtOAc (30 mL×3) and the combined organic extracts washed with brine (50 mL), dried over $Na_2SO_4$, filtered and evaporated under reduced pressure to give tert-butyl 3-((4-chloropyridin-3-yl)oxy)piperidine-1-carboxylate (400 mg, crude) as yellow oil.

2. Synthesis of N-(4-(3-((1-acryloylpiperidin-3-yl)oxy)pyridin-4-yl)-2-methylbenzyl)-1-(tert-butyl)-1H-1,2,3-triazole-4-carboxamide

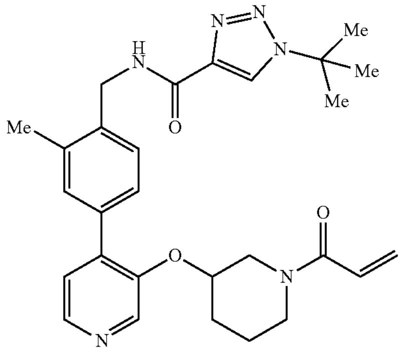 [SMILES: C=CC(=O)N1CCCC(Oc2cnccc2-c2ccc(CNC(=O)c3cn(C(C)(C)C)nn3)c(C)c2)C1]

The compound was obtained from tert-butyl 3-((4-chloropyridin-3-yl)oxy)piperidine-1-carboxylate and Intermediate 1: 1-(tert-butyl)-N-(2-methyl-4-(4,4,5,5-tetramethyl-1,3,2-dioxaborolan-2-yl)benzyl)-1H-1,2,3-triazole-4-carboxamide, following the procedure described in Example 1, steps 2 to 4. The residue was purified by Prep-HPLC (Method B, organic gradient: 35-65%) to give N-(4-(3-((1-acryloylpiperidin-3-yl)oxy)pyridin-4-yl)-2-methylbenzyl)-1-(tert-butyl)-1H-1,2,3-triazole-4-carboxamide (77.20 mg, 40.16% yield) as a white solid. LCMS m/z=503.2 (M+H)+. $^1$H NMR (500 MHz, MeOD-$d_4$) δ: 8.51-8.35 (m, 2H), 8.23-8.22 (m, 1H), 7.42-7.34 (m, 4H), 6.64-6.34 (m, 1H), 6.07-5.93 (m, 1H), 5.67-5.45 (m, 1H), 4.65 (s, 2H), 4.30-4.22 (m, 1H), 4.14-3.70 (m, 1H), 3.56-3.38 (m, 1H), 3.32-2.93 (m, 1H), 2.43 (s, 3H), 2.02-1.87 (m, 2H), 1.73 (s, 10H), 1.65-1.27 (m, 2H).

Example 39. N-(4-(5-((1-acryloylpiperidin-3-yl)oxy)pyrimidin-4-yl)-2-methylbenzyl)-1-(tert-butyl)-1H-1,2,3-triazole-4-carboxamide

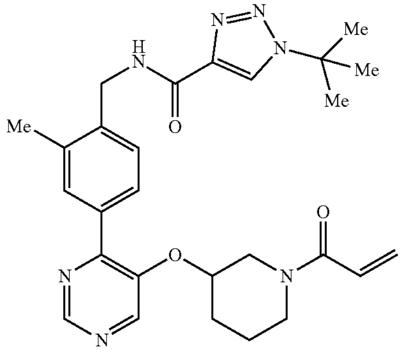 [SMILES: C=CC(=O)N1CCCC(Oc2cncnc2-c2ccc(CNC(=O)c3cn(C(C)(C)C)nn3)c(C)c2)C1]

1. Synthesis of tert-butyl 3-((4,6-dichloropyrimidin-5-yl)oxy)piperidine-1-carboxylate

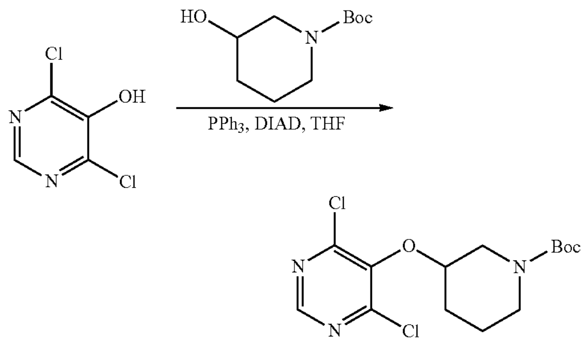

To a solution of 4,6-dichloropyrimidin-5-ol (1.0 g, 6.06 mmol) in THF (20 mL) was added tert-butyl-3-hydroxypiperidine-1-carboxylate (1.59 g, 7.88 mmol) and $PPh_3$ (2.07 g, 7.88 mmol) at 25° C. DIAD (2.45 g, 12.12 mmol) was added portion-wise and the reaction stirred at 25° C. under $N_2$ for 12 h. The mixture was filtered, the filtrate concentrated in vacuo and the residue purified by silica gel column chromatography eluting with (PE/EtOAc=I/O to 5/1) to give tert-butyl 3-((4,6-dichloropyrimidin-5-yl)oxy)piperidine-1-carboxylate (200 mg, 9.48% yield) as a yellow solid. LCMS m/z=292.2 (M+H)+

2. Synthesis of tert-butyl 3-((4-chloro-6-hydrazineylpyrimidin-5-yl)oxy)piperidine-1-carboxylate

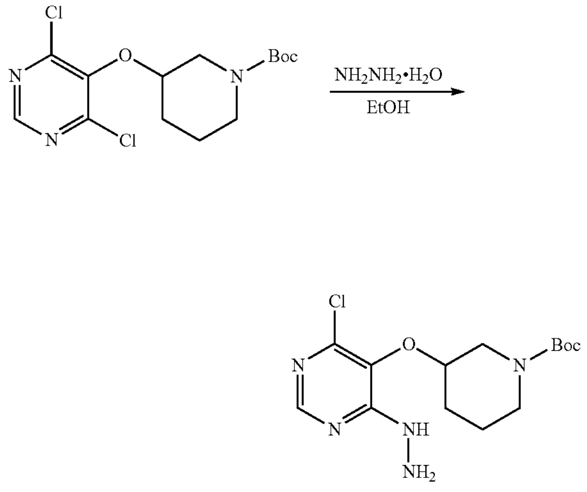

To a solution of tert-butyl 3-((4,6-dichloropyrimidin-5-yl)oxy)piperidine-1-carboxylate (200 mg, 574.35 μmol) in EtOH (10 mL) was added $NH_2NH_2 \cdot H_2O$ (500 mg, 85% purity) at 20° C. and the reaction stirred at 20° C. for 1 h. The mixture was evaporated under reduced pressure to give tert-butyl 3-((4-chloro-6-hydrazineylpyrimidin-5-yl)oxy)piperidine-1-carboxylate (200 mg, crude) as a white solid, which was used without further purification. LCMS m/z=344.3 (M+H)+

3. Synthesis of tert-butyl 3-((4-chloropyrimidin-5-yl)oxy)piperidine-1-carboxylate

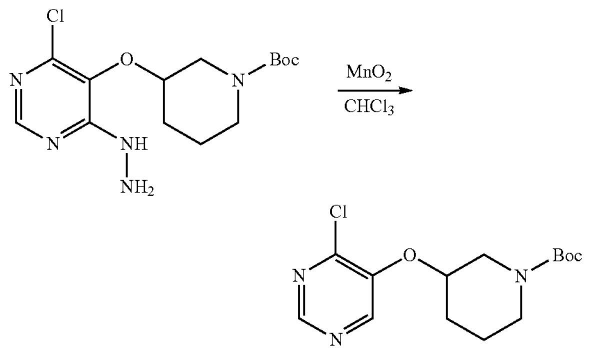

To a solution of tert-butyl 3-((4-chloro-6-hydrazineylpyrimidin-5-yl)oxy)piperidine-1-carboxylate (200 mg, 581.72 μmol) in $CHCl_3$ (20 mL) was added $MnO_2$ (202.30 mg, 2.33 mmol) and the reaction stirred at 20° C. for 1 h. The mixture was filtered and the filtrate concentrated in vacuo. The crude was purified by silica gel column chromatography eluting with PE/EtOAc (I/O to 0/1) to give tert-butyl 3-((4-chloropyrimidin-5-yl)oxy)piperidine-1-carboxylate (140 mg, 71.74% yield) as a yellow solid. LCMS m/z=314.2 (M+H)+

4. Synthesis of N-(4-(5-((1-acryloylpiperidin-3-yl)oxy)pyrimidin-4-yl)-2-methylbenzyl)-1-(tert-butyl)-1H-1,2,3-triazole-4-carboxamide

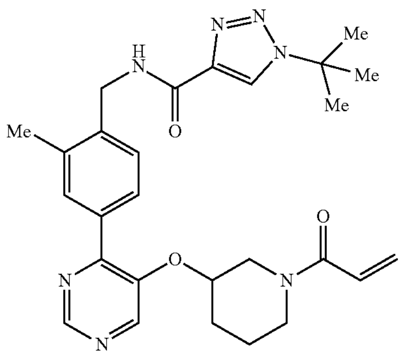

The compound was obtained from tert-butyl 3-((4-chloropyrimidin-5-yl)oxy)piperidine-1-carboxylate and Intermediate 1: 1-(tert-butyl)-N-(2-methyl-4-(4,4,5,5-tetramethyl-1,3,2-dioxaborolan-2-yl)benzyl)-1H-1,2,3-triazole-4-carboxamide, following a similar procedure to that described in Example 2, steps 2 to 4. The crude was purified by prep HPLC (Method B, organic gradient 28-58%) to give N-(4-(5-((1-acryloylpiperidin-3-yl)oxy)pyrimidin-4-yl)-2-methylbenzyl)-1-(tert-butyl)-1H-1,2,3-triazole-4-carboxamide (52 mg, 45.62% yield) as a white solid. LCMS m/z=504.2 (M+H)+. $^1H$ NMR (400 MHz, DMSO-$d_6$) δ: 8.95 (s, 1H), 8.80 (s, 1H), 8.71-8.68 (m, 2H), 7.80-7.71 (m, 2H), 7.25-7.21 (m, 1H), 6.75-6.45 (m, 1H), 5.96-5.83 (m, 1H), 5.54-5.32 (m, 1H), 4.83 (s, 1H), 4.44 (d, 2H), 4.15-3.02 (m, 4H), 2.33 (s, 3H), 1.89-1.84 (m, 2H), 1.61 (s, 9H), 1.50-1.11 (m, 2H).

Example 40. (E)-1-(tert-butyl)-N-(4-(3-((1-(4-(dimethylamino)but-2-enoyl)azetidin-3-yl)oxy)pyridin-4-yl)-2-methylbenzyl)-1H-1,2,3-triazole-4-carboxamide

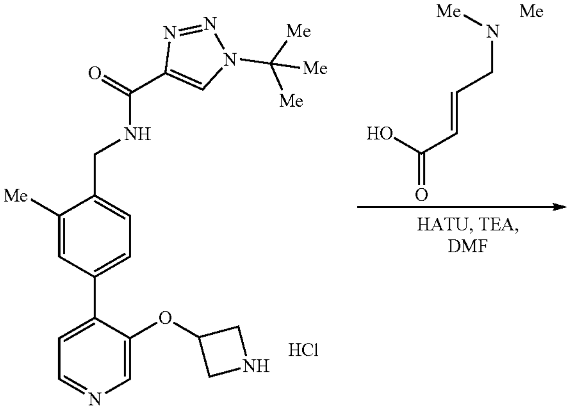

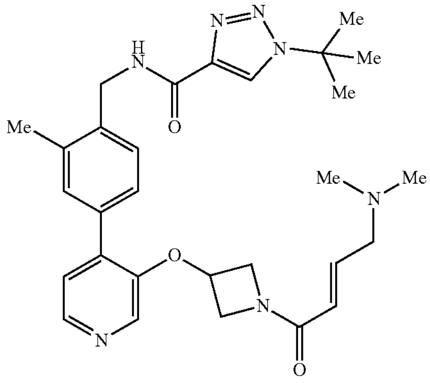

The compound was obtained from Example 33, Step 3: N-(4-(3-(azetidin-3-yloxy)pyridin-4-yl)-2-methylbenzyl)-1-(tert-butyl)-1H-1,2,3-triazole-4-carboxamide hydrochloride and (E)-4-(dimethylamino)but-2-enoic acid, following the procedure described in Example 33, Step 4. The crude was purified by prep-HPLC (Method E, organic gradient: 13-36%) to give (E)-1-(tert-butyl)-N-(4-(3-((1-(4-(dimethylamino)but-2-enoyl)azetidin-3-yl)oxy)pyridin-4-yl)-2-methylbenzyl)-1H-1,2,3-triazole-4-carboxamide (18 mg, 23.73% yield) as a brown solid. LCMS m/z=532.2 (M+H)+ $^{1}$H NMR (500 MHz, MeOD-$d_4$) δ: 8.48 (s, 1H), 8.30 (d, 1H), 8.11 (s, 1H), 7.48-7.37 (m, 4H), 6.76-6.67 (m, 1H), 6.42 (d, 1H), 5.24-5.20 (m, 1H), 4.74-4.70 (m, 1H), 4.65 (s, 2H), 4.49-4.46 (m, 1H), 4.28 (d, 1H), 4.03 (d, 1H), 3.79 (d, 2H), 2.78 (s, 6H), 2.45 (s, 3H), 1.71 (s, 9H)

Example 41. (E)-1-(tert-butyl)-N-(4-(3-((1-(4-(dimethylamino)but-2-enoyl)pyrrolidin-3-yl)oxy)pyridin-4-yl)-2-methylbenzyl)-1H-1,2,3-triazole-4-carboxamide

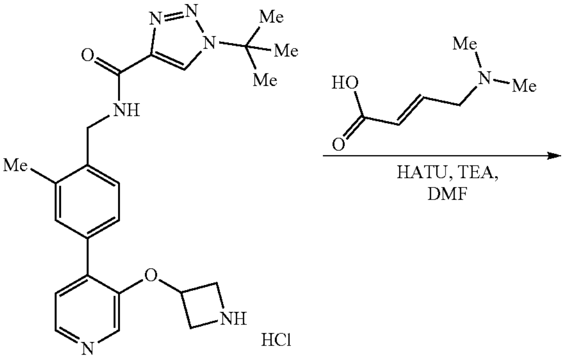

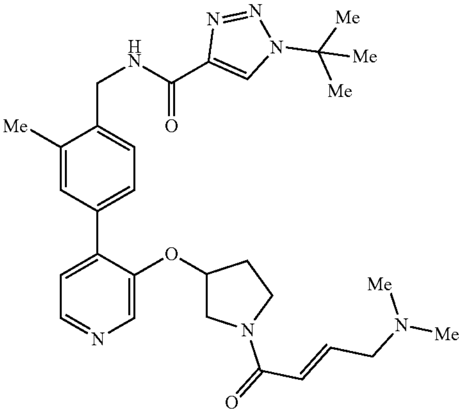

(E)-1-(tert-butyl)-N-(4-(3-((1-(4-(dimethylamino)but-2-enoyl)pyrrolidin-3-yl)oxy)pyridin-4-yl)-2-methylbenzyl)-1H-1,2,3-triazole-4-carboxamide was obtained as a brown oil, from (E)-4-(dimethylamino)but-2-enoic acid, tert-butyl 3-((4-chloropyridin-3-yl)oxy)pyrrolidine-1-carboxylate and Intermediate 1: 1-(tert-butyl)-N-(2-methyl-4-(4,4,5,5-tetramethyl-1,3,2-dioxaborolan-2-yl)benzyl)-1H-1,2,3-triazole-4-carboxamide following a similar procedure to that described in Example 33, steps 2 to 4. The crude was purified by prep HPLC (Method E, organic gradient 15-35%), 9.0 mg. LCMS m/z=546.2 (M+H)+$^{1}$H NMR (500 MHz, MeOD-$d_4$) δ: 8.51 (d, 1H), 8.43 (d, 1H), 8.28-8.26 (m, 1H), 7.45-7.42 (m, 1H), 7.39 (s, 1H), 7.34 (d, 2H), 6.80-6.69 (m, 1H), 6.46-6.31 (m, 1H), 5.16 (d, 1H), 4.63-4.58 (m, 4H), 3.80-3.68 (m, 2H), 3.47-3.38 (m, 2H), 2.49-2.38 (m, 9H), 2.27-2.11 (m, 2H), 1.72 (d, 9H).

Example 42. (E)-1-(tert-butyl)-N-(4-(3-((1-(4-(dimethylamino)but-2-enoyl)piperidin-4-yl)oxy)pyridin-4-yl)-2-methylbenzyl)-1H-1,2,3-triazole-4-carboxamide

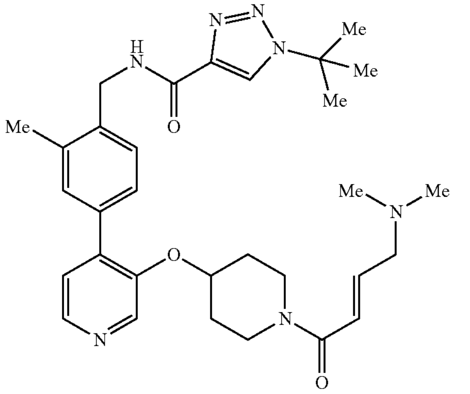 [SMILES: Cc1cc(-c2ccncc2OC2CCN(C(=O)/C=C/CN(C)C)CC2)ccc1CNC(=O)c1cn(C(C)(C)C)nn1]

(E)-1-(tert-Butyl)-N-(4-(3-((1-(4-(dimethylamino)but-2-enoyl)piperidin-4-yl)oxy)pyridin-4-yl)-2-methylbenzyl)-1H-1,2,3-triazole-4-carboxamide was obtained from tert-butyl 4-((4-chloropyridin-3-yl)oxy)piperidine-1-carboxylate, Intermediate 1:1-(tert-butyl)-N-(2-methyl-4-(4,4,5,5-tetramethyl-1,3,2-dioxaborolan-2-yl)benzyl)-1H-1,2,3-triazole-4-carboxamide and (E)-4-(dimethylamino)but-2-enoic acid following a similar procedure to that described in Example 33, steps 1 to 4. LCMS m/z=560.2 (M+H)+. $^1$H NMR (500 MHz, MeOD-$d_4$) δ: 8.47 (s, 1H), 8.41 (s, 1H), 8.24 (d, 1H), 7.51-7.37 (m, 4H), 6.72-6.64 (m, 2H), 4.75-4.70 (m, 1H), 4.65 (s, 2H), 3.73-3.64 (m, 1H), 3.60-3.45 (m, 3H), 3.40-3.39 (m, 2H), 2.52-2.42 (m, 9H), 1.96-1.84 (m, 2H), 1.80-1.73 (m, 2H), 1.71 (s, 9H).

Example 43. 1-(tert-butyl)-N-(2-methyl-4-(3-((1-propioloylpyrrolidin-3-yl)oxy)pyridin-4-yl)benzyl)-1H-1,2,3-triazole-4-carboxamide

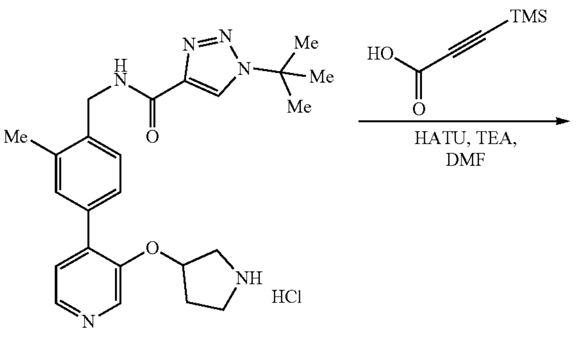

-continued

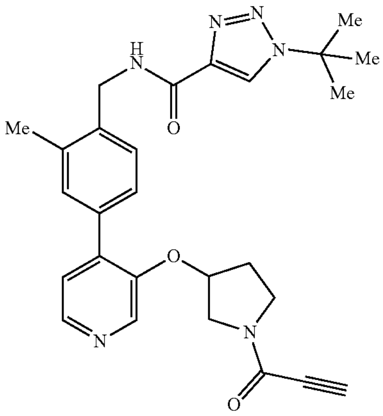

The compound was obtained as a yellow solid, from tert-butyl 4-((4-chloropyridin-3-yl)oxy)pyrrolidine-1-carboxylate, Intermediate 1:1-(tert-butyl)-N-(2-methyl-4-(4,4,5,5-tetramethyl-1,3,2-dioxaborolan-2-yl)benzyl)-1H-1,2,3-triazole-4-carboxamide and 3-(trimethylsilyl)propiolic acid following a similar procedure to that described in Example 33, steps 1 to 4. The crude was purified by prep-HPLC (Method E, organic gradient: 23-48%) to give 1-(tert-butyl)-N-(2-methyl-4-(3-((1-propioloylpyrrolidin-3-yl)oxy)pyridin-4-yl)benzyl)-1H-1,2,3-triazole-4-carboxamide (3.0 mg, 7.6% yield, 97.54% purity) as a yellow solid. LCMS m/z=487.1 (M+H)+. $^1$H NMR (500 MHz, MeOD-$d_4$) δ: 9.09-8.93 (m, 1H), 8.70 (d, 1H), 8.51 (d, 1H), 8.30 (d, 1H), 7.70-7.23 (m, 4H), 5.31-5.15 (m, 1H), 4.57-4.38 (m, 3H), 3.98-3.71 (m, 2H), 3.56-3.48 (m, 2H), 2.35 (d, 3H), 2.25-2.08 (m, 2H), 1.64 (s, 9H).

Example 44. 1-(tert-butyl)-N-(2-methyl-4-(3-((1-propioloylpiperidin-4-yl)oxy)pyridin-4-yl)benzyl)-1H-1,2,3-triazole-4-carboxamide

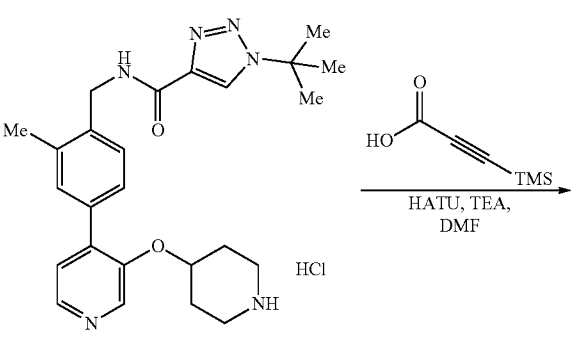

-continued

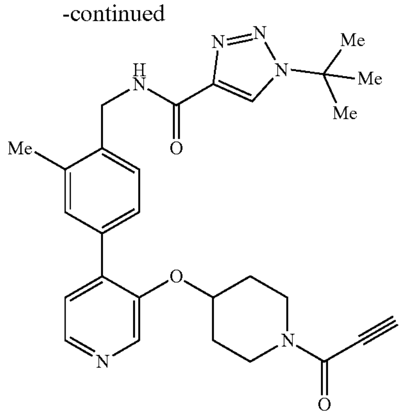

1-(tert-Butyl)-N-(2-methyl-4-(3-((1-propioloylpiperidin-4-yl)oxy)pyridin-4-yl)benzyl)-1H-1,2,3-triazole-4-carboxamide was obtained as a white solid, from tert-butyl 4-((4-chloropyridin-3-yl)oxy)piperidine-1-carboxylate, Intermediate 1:1-(tert-butyl)-N-(2-methyl-4-(4,4,5,5-tetramethyl-1,3,2-dioxaborolan-2-yl)benzyl)-1H-1,2,3-triazole-4-carboxamide and 3-(trimethylsilyl)propiolic acid, following a similar procedure to that described in Example 33, steps 1 to 4. The crude was purified by prep HPLC (Method E, organic gradient was (28-48%). 6.0 mg, 5.3%. LCMS m/z=501.2 (M+H)+. $^1$H NMR (500 MHz, MeOD-$d_4$) δ: 8.87 (br s, 0.2H), 8.47 (s, 1H), 8.42 (s, 1H), 8.25 (d, 1H), 7.48-7.41 (m, 4H), 4.77-4.59 (m, 3H), 3.96 (s, 1H), 3.87-3.77 (m, 1H), 3.71-3.65 (m, 2H), 3.47-3.38 (m, 1H), 2.46 (s, 3H), 1.95-1.74 (m, 4H), 1.72 (s, 9H).

Example 45. 1-(tert-butyl)-N-(4-(3-((1-cyanoazetidin-3-yl)oxy)pyridin-4-yl)-2-methylbenzyl)-1H-1,2,3-triazole-4-carboxamide

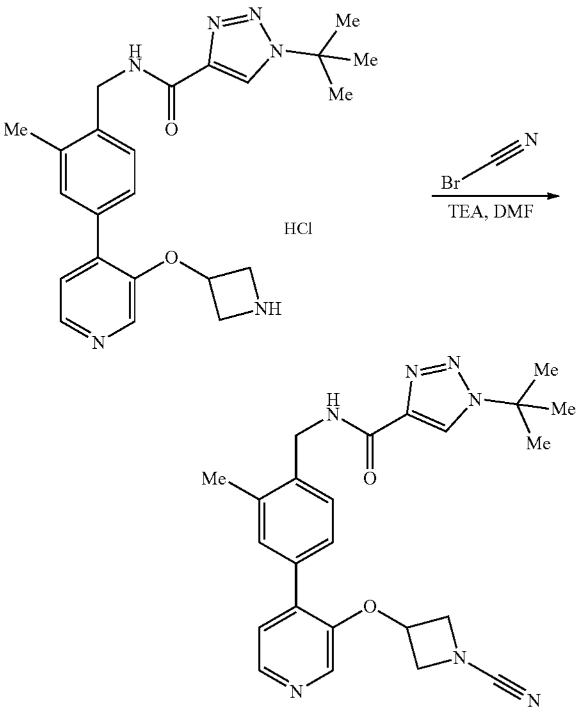

To a solution of Example 33, step 3: N-(4-(3-(azetidin-3-yloxy)pyridin-4-yl)-2-methylbenzyl)-1-(tert-butyl)-1H-1,2,3-triazole-4-carboxamide hydrochloride (200 mg, 0.48 mmol) and cyanic bromide (60.5 mg, 0.58 mmol) in DMF (6.0 mL) was added TEA (219 mg, 2.16 mmol). The reaction mixture was stirred at 25° C. for 3 h. The mixture was concentrated in vacuo and the residue was purified by silica gel column chromatography (EtOAc) and prep-HPLC (Method E, organic gradient 25-50%) to give 1-(tert-butyl)-N-(4-(3-((1-cyanoazetidin-3-yl)oxy)pyridin-4-yl)-2-methylbenzyl)-1H-1,2,3-triazole-4-carboxamide (22.0 mg, 10.09% yield) as a white solid. LCMS m/z=446.3 (M+H)+$^1$H NMR (500 MHz, MeOD-$d_4$) δ: 8.48 (s, 1H), 8.32 (d, 1H), 8.09 (s, 1H), 7.55-7.41 (m, 4H), 5.22-5.15 (m, 1H), 4.69-4.64 (m, 2H), 4.59-4.56 (m, 2H), 4.22-4.20 (m, 2H), 2.47 (s, 3H), 1.71 (s, 9H).

Example 46. 1-(tert-butyl)-N-(4-(3-((1-cyanopyrrolidin-3-yl)oxy)pyridin-4-yl)-2-methylbenzyl)-1H-1,2,3-triazole-4-carboxamide 1. Synthesis of 1-(tert-butyl)-N-(2-methyl-4-(3-(pyrrolidin-3-yloxy)pyridin-4-yl)benzyl)-1H-1,2,3-triazole-4-carboxamide

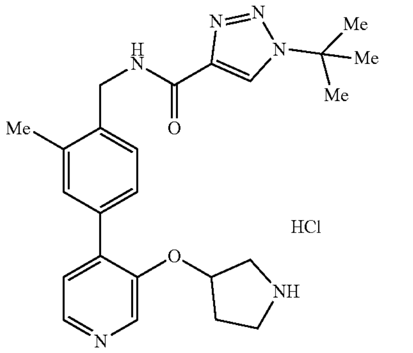 [SMILES: Cc1cc(-c2ccncc2OC2CCNC2)ccc1CNC(=O)c1cn(C(C)(C)C)nn1 ; Cl]

1-(tert-butyl)-N-(2-methyl-4-(3-(pyrrolidin-3-yloxy)pyridin-4-yl)benzyl)-1H-1,2,3-triazole-4-carboxamide was obtained from tert-butyl 4-((4-chloropyridin-3-yl)oxy)pyrrolidine-1-carboxylate and Intermediate 1:1-(tert-butyl)-N-(2-methyl-4-(4,4,5,5-tetramethyl-1,3,2-dioxaborolan-2-yl)benzyl)-1H-1,2,3-triazole-4-carboxamide, following the procedure described in Example 33, steps 1 to 3. $^1$H NMR. (500 MHz, MeOD-$d_4$) δ: 8.83 (s, 1H), 8.60 (d, 1H), 8.49 (s, 1H), 8.08 (d, 1H), 7.63-7.57 (m, 2H), 7.51 (d, 1H), 5.48-5.46 (m, 1H), 4.67 (s, 2H), 3.78-3.44 (m, 3H), 2.50 (s, 3H), 2.43-2.35 (m, 2H), 1.72 (s, 9H).

2. Synthesis of 1-(tert-butyl)-N-(4-(3-((1-cyanopyrrolidin-3-yl)oxy)pyridin-4-yl)-2-methylbenzyl)-1H-1,2,3-triazole-4-carboxamide

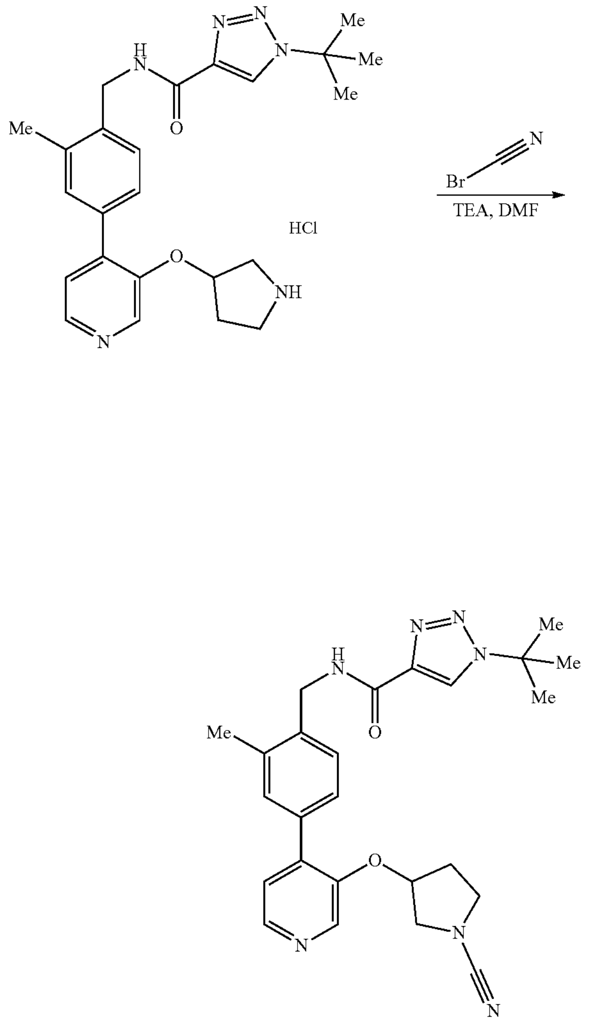

1-(tert-Butyl)-N-(4-(3-((1-cyanopyrrolidin-3-yl)oxy)pyridin-4-yl)-2-methylbenzyl)-1H-1,2,3-triazole-4-carboxamide was obtained as a white solid, from 1-(tert-butyl)-N-(2-methyl-4-(3-(pyrrolidin-3-yloxy)pyridin-4-yl)benzyl)-1H-1,2,3-triazole-4-carboxamide hydrochloride, following a similar procedure to that described in Example 61, except the HPLC organic gradient was 23-48%. LCMS m/z=460.1 (M+H)+$^1$H NMR (500 MHz, MeOD-$d_4$) δ: 8.47 (s, 1H), 8.40 (s, 1H), 8.29 (d, 1H), 7.48-7.39 (m, 4H), 5.14-5.07 (m, 1H), 4.66 (s, 2H), 3.63-3.60 (m, 1H), 3.55-3.48 (m, 2H), 3.39-3.33 (m, 1H), 2.46 (s, 3H), 2.18-2.09 (m, 2H), 1.71 (s, 9H).

Example 47. 1-(tert-butyl)-N-(4-(3-((1-cyanopiperidin-4-yl)oxy)pyridin-4-yl)-2-methylbenzyl)-1H-1,2,3-triazole-4-carboxamide 1. Synthesis of 1-(tert-butyl)-N-(2-methyl-4-(3-(piperidin-4-yloxy)pyridin-4-yl)benzyl)-1H-1,2,3-triazole-4-carboxamide hydrochloride

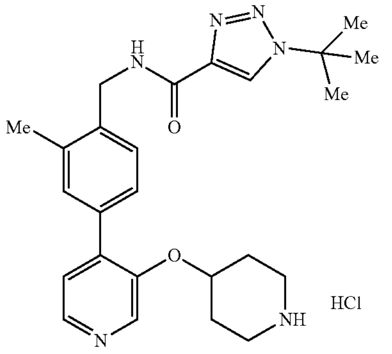 [SMILES: Cc1cc(-c2ccncc2OC2CCNCC2)ccc1CNC(=O)c1cn(C(C)(C)C)nn1 ; Cl]

1-(tert-Butyl)-N-(2-methyl-4-(3-(piperidin-4-yloxy)pyridin-4-yl)benzyl)-1H-1,2,3-triazole-4-carboxamide hydrochloride was obtained from tert-butyl 4-((4-chloropyridin-3-yl)oxy)piperidine-1-carboxylate and Intermediate 1:1-(tert-butyl)-N-(2-methyl-4-(4,4,5,5-tetramethyl-1,3,2-dioxaborolan-2-yl)benzyl)-1H-1,2,3-triazole-4-carboxamide following the steps described in Example 33, steps 1 to 3. LCMS m/z=449.2 (M+H)+

2. Synthesis of 1-(tert-butyl)-N-(4-(3-((1-cyanopiperidin-4-yl)oxy)pyridin-4-yl)-2-methylbenzyl)-1H-1,2,3-triazole-4-carboxamide

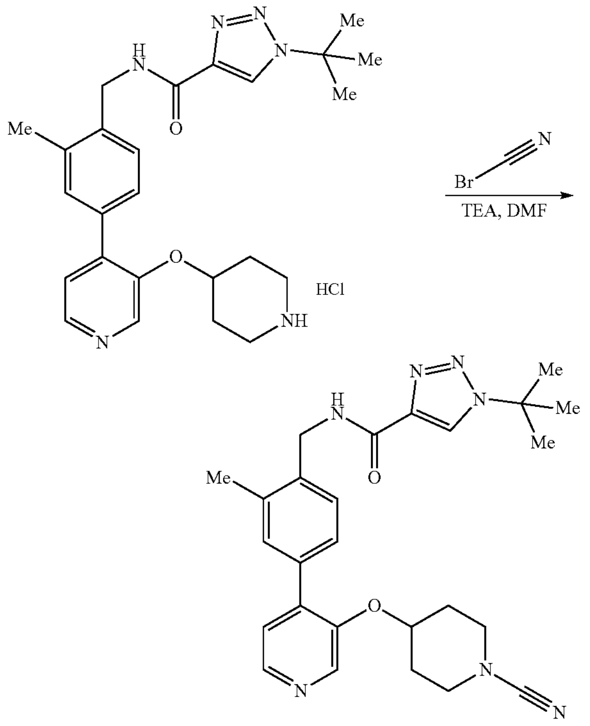

1-(tert-Butyl)-N-(4-(3-((1-cyanopiperidin-4-yl)oxy)pyridin-4-yl)-2-methylbenzyl)-1H-1,2,3-triazole-4-carboxamide was obtained as a white solid from 1-(tert-butyl)-N-(2-methyl-4-(3-(piperidin-4-yloxy)pyridin-4-yl)benzyl)-1H-1,2,3-triazole-4-carboxamide hydrochloride and cyanic bromide following a similar procedure to that described in Example 61, except the compound was purified using prep HPLC (Method E, organic gradient 28-48%) (10.0 mg, 11.8% yield). LCMS m/z=474.1 (M+H)+. $^1H$ NMR (500 MHz, MeOD-$d_4$) δ: 8.48 (s, 1H), 8.42 (s, 1H), 8.27 (d, 1H), 7.51-7.42 (m, 4H), 4.70-4.64 (m, 3H), 3.26-3.22 (m, 2H), 3.16-3.09 (m, 2H), 2.47 (s, 3H), 2.03-1.95 (m, 2H), 1.86-1.78 (m, 2H), 1.71 (s, 9H).

Example 48: 1-(tert-butyl)-N-(3-fluoro-2-methyl-4-(3-((1-propioloylpyrrolidin-2-yl)methoxy)pyridin-4-yl)benzyl)-1H-1,2,3-triazole-4-carboxamide

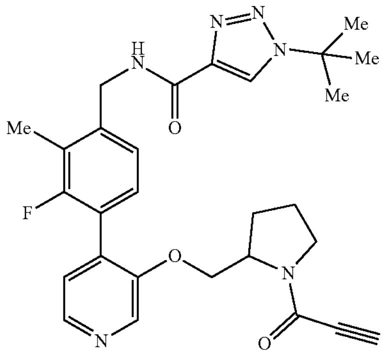 [SMILES: C#CC(=O)N1CCCC1COc1cnccc1-c1ccc(CNC(=O)c2cn(C(C)(C)C)nn2)c(C)c1F]

1. Synthesis of 4-bromo-3-(pyrrolidin-2-ylmethoxy)pyridine (100142-1527)

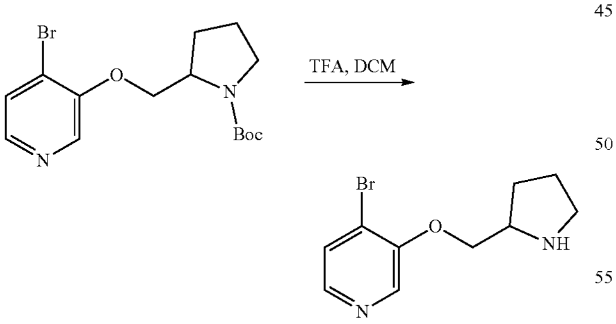

To a solution of tert-butyl 2-(((4-bromopyridin-3-yl)oxy)methyl)pyrrolidine-1-carboxylate (1.10 g, 3.08 mmol) in DCM (10 mL) was added TFA (4.71 mL, 61.58 mmol) and the reaction stirred at rt for 18 h. The mixture was diluted with MeOH and purified on an SCX column eluting with 2 M $NH_3$-MeOH to give 4-bromo-3-(pyrrolidin-2-ylmethoxy)pyridine (440 mg, 52.78% yield) as a clear viscous gum. LCMS m/z=256.9, 258.9 (M+H)+

2. Synthesis of benzyl 2-(((4-bromopyridin-3-yl)oxy)methyl)pyrrolidine-1-carboxylate

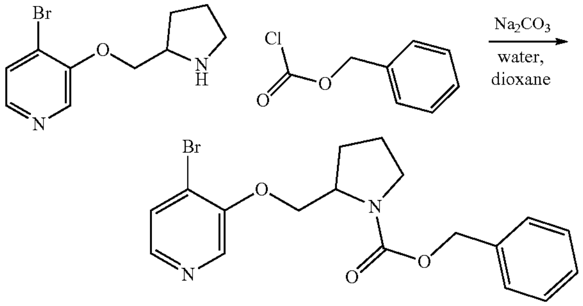

A solution of benzyl carbonochloridate (300.94 mg, 1.71 mmol) in dioxane (4 mL) was added dropwise to 4-bromo-3-(pyrrolidin-2-ylmethoxy)pyridine (440 mg, 1.71 mmol) and $Na_2CO_3$ (287.52 mg, 3.42 mmol) in water (4 mL) and the reaction stirred at rt for 3 h. The mixture was diluted with DCM and the organic phase separated, dried over $Na_2SO_4$, filtered and the filtrate concentrated in vacuo. The residue was purified by silica gel column chromatography eluting with heptanes/EtOAc (1/1) to give benzyl 2-(((4-bromopyridin-3-yl)oxy)methyl)pyrrolidine-1-carboxylate (500 mg, 67.2% yield) as a sticky white solid. LCMS m/z=390.8, 392.8 (M+H)+

3. Synthesis of benzyl 2-(((4-(4-(((tert-butoxycarbonyl)amino)methyl)-2-fluoro-3-methylphenyl)pyridin-3-yl)oxy)methyl)pyrrolidine-1-carboxylate

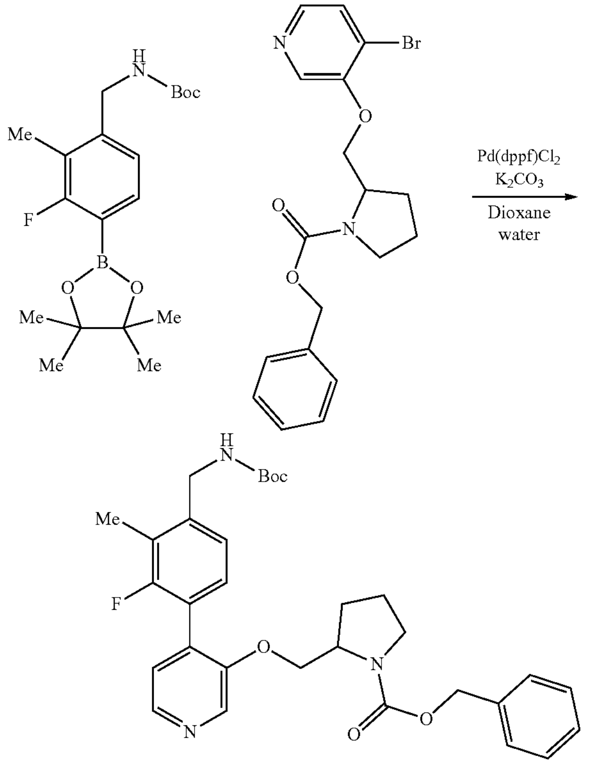

A mixture of benzyl 2-((pyridin-3-yloxy)methyl)pyrrolidine-1-carboxylate (500 mg, 1.28 mmol), Intermediate 3, step 5: tert-butyl (3-fluoro-2-methyl-4-(4,4,5,5-tetramethyl-1,3,2-dioxaborolan-2-yl)benzyl)carbamate (701.28 mg, 1.92 mmol), $K_2CO_3$ (530.73 mg, 3.84 mmol) and $Pd(dppf)Cl_2$: DCM (104.53 mg, 128.00 μmol) was purged with $N_2$. Dioxane (5 mL) and water (1.70 mL) were added via syringe and the reaction heated in a MW oven at 95° C. for 18 h. The cooled mixture was diluted with EtOAc, filtered and the filtrate concentrated in vacuo. The residue was purified by silica gel column chromatography eluting with heptanes/EtOAc (1/1) to give benzyl 2-(((4-(4-(((tert-butoxycarbonyl)amino)methyl)-2-fluoro-3-methylphenyl)pyridin-3-yl)oxy)methyl)pyrrolidine-1-carboxylate (730 mg, 93.39% yield) as a dark sticky gum. LCMS m/z=550 (M+H)+

4. Synthesis of benzyl 2-(((4-(4-(aminomethyl)-2-fluoro-3-methylphenyl)pyridin-3-yl)oxy)methyl)pyrrolidine-1-carboxylate

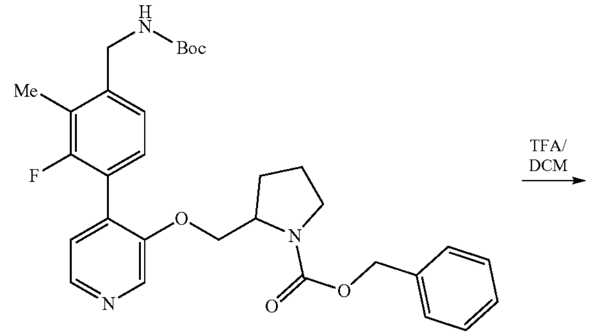

-continued

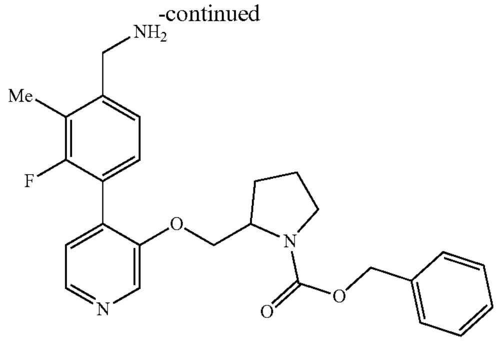

To a solution of benzyl 2-(((4-(4-(((tert-butoxycarbonyl)amino)methyl)-2-fluoro-3-methylphenyl)pyridin-3-yl)oxy)methyl)pyrrolidine-1-carboxylate (730 mg, 1.33 mmol) in DCM (5 mL) was added TFA (2.03 mL, 26.60 mmol) and the reaction stirred at rt for 18 h. The mixture was diluted with MeOH and purified on a SCX column eluting with 2 M TEA-MeOH to give benzyl 2-(((4-(4-(aminomethyl)-2-fluoro-3-methylphenyl)pyridin-3-yl)oxy)methyl)pyrrolidine-1-carboxylate (480 mg, 72.26% yield) as a viscous brown gum. LCMS m/z=450.0 (M+H)+

5. Synthesis of benzyl 2-(((4-(4-((1-(tert-butyl)-1H-1,2,3-triazole-4-carboxamido)methyl)-2-fluoro-3-methylphenyl)pyridin-3-yl)oxy)methyl)pyrrolidine-1-carboxylate

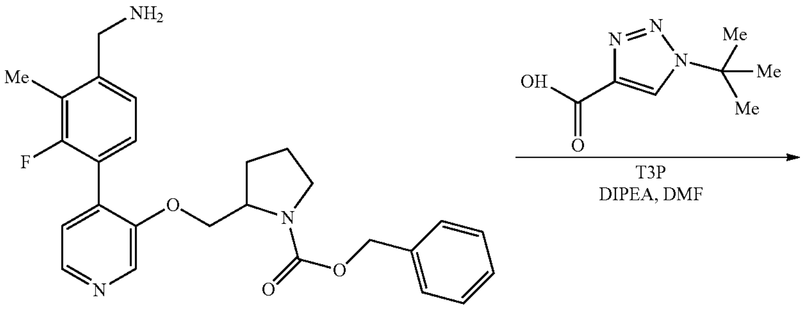

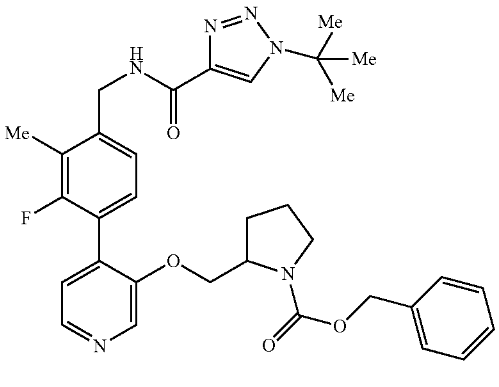

The compound was obtained from benzyl 2-(((4-(4-(aminomethyl)-2-fluoro-3-methylphenyl)pyridin-3-yl)oxy)methyl)pyrrolidine-1-carboxylate and 1-(tert-butyl)-1H-1,2,3-triazole-4-carboxylic acid following a similar procedure to that described in Example 42, step 1: tert-butyl (1-(4-(4-((1-(tert-butyl)-1H-pyrazole-4-carboxamido)methyl)-3-methylphenyl)pyridin-3-yl)piperidin-3-yl)(methyl)carbamate. The crude was purified by silica gel column chromatography eluting with EtOAc/MeOH (100/1) to give benzyl 2-(((4-(4-((1-(tert-butyl)-1H-1,2,3-triazole-4-carboxamido)methyl)-2-fluoro-3-methylphenyl)pyridin-3-yl)oxy)methyl)pyrrolidine-1-carboxylate (530 mg, 82.46% yield) as a viscous yellow gum. LCMS m/z=601.0 (M+H)+

6. Synthesis of 1-(tert-butyl)-N-(3-fluoro-2-methyl-4-(3-(pyrrolidin-2-ylmethoxy)pyridin-4-yl)benzyl)-1H-1,2,3-triazole-4-carboxamide

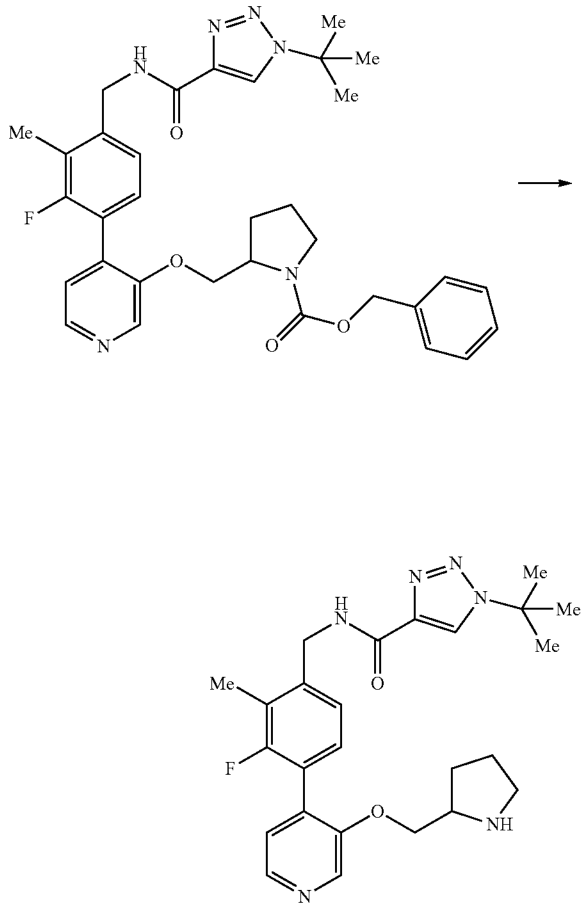

1-(tert-butyl)-N-(3-fluoro-2-methyl-4-(3-(pyrrolidin-2-ylmethoxy)pyridin-4-yl)benzyl)-1H-1,2,3-triazole-4-carboxamide was obtained as a yellow-orange gum from benzyl 2-(((4-(4-((1-(tert-butyl)-1H-1,2,3-triazole-4-carboxamido)methyl)-2-fluoro-3-methylphenyl)pyridin-3-yl)oxy)methyl)pyrrolidine-1-carboxylate, following a similar procedure to that described in Example 22, step 3: (R)-1-(tert-butyl)-N-(2-methyl-4-(3-(3-(methylamino)piperidin-1-yl)pyridin-4-yl)benzyl)-1H-1,2,3-triazole-4-carboxamide. (270 mg, 59.0%) LCMS m/z=467.0 (M+H)+

7. Synthesis of 1-(tert-butyl)-N-(3-fluoro-2-methyl-4-(3-((1-propioloylpyrrolidin-2-yl)methoxy)pyridin-4-yl)benzyl)-1H-1,2,3-triazole-4-carboxamide

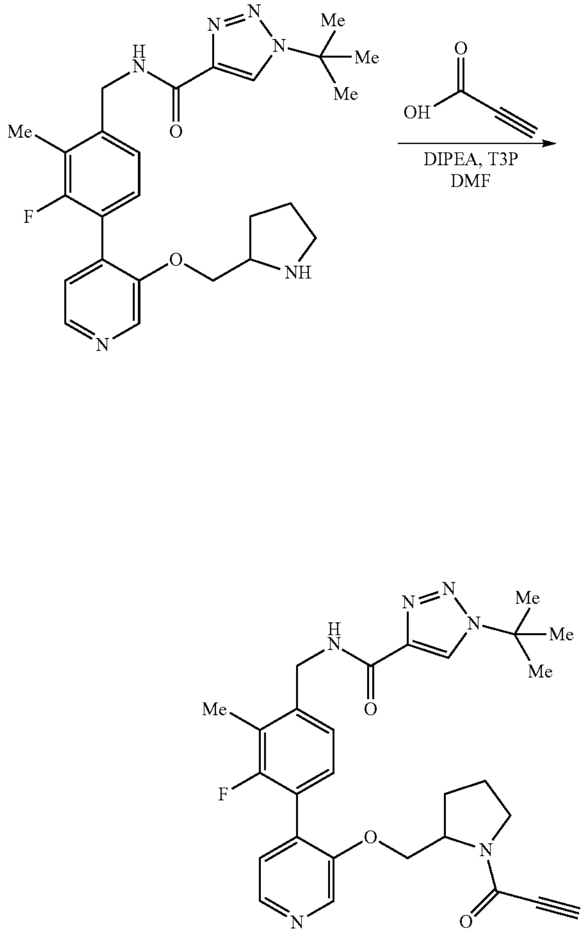

To a solution of 1-(tert-butyl)-N-(3-fluoro-2-methyl-4-(3-(pyrrolidin-2-ylmethoxy)pyridin-4-yl)benzyl)-1H-1,2,3-triazole-4-carboxamide (30 mg, 64.30 μmol) in DMF (1 mL) was added propiolic acid (9.01 mg, 128.60 μmol) followed by DIPEA (16.62 mg, 128.60 μmol) and the solution stirred for 5 mins. T3P (81.84 mg, 128.60 μmol, 50% purity) was added dropwise and after complete addition, the reaction was stirred at rt for 3 h. The mixture was diluted with EtOAc and washed with water. The organic phase was dried over $Na_2SO_4$, filtered and the filtrate evaporated under reduced pressure. The residue was purified by Prep HPLC (Method D, organic gradient 5-35%) to give 1-(tert-butyl)-N-(3-fluoro-2-methyl-4-(3-((1-propioloylpyrrolidin-2-yl)methoxy)pyridin-4-yl)benzyl)-1H-1,2,3-triazole-4-carboxamide, 1.0 mg (3%) of a yellow solid. LCMS m/z=519.2 (M+H)+

Example 49. N-(4-(3-((1-acryloylpyrrolidin-2-yl)methoxy)pyridin-4-yl)-3-fluoro-2-methylbenzyl)-1-(tert-butyl)-1H-1,2,3-triazole-4-carboxamide

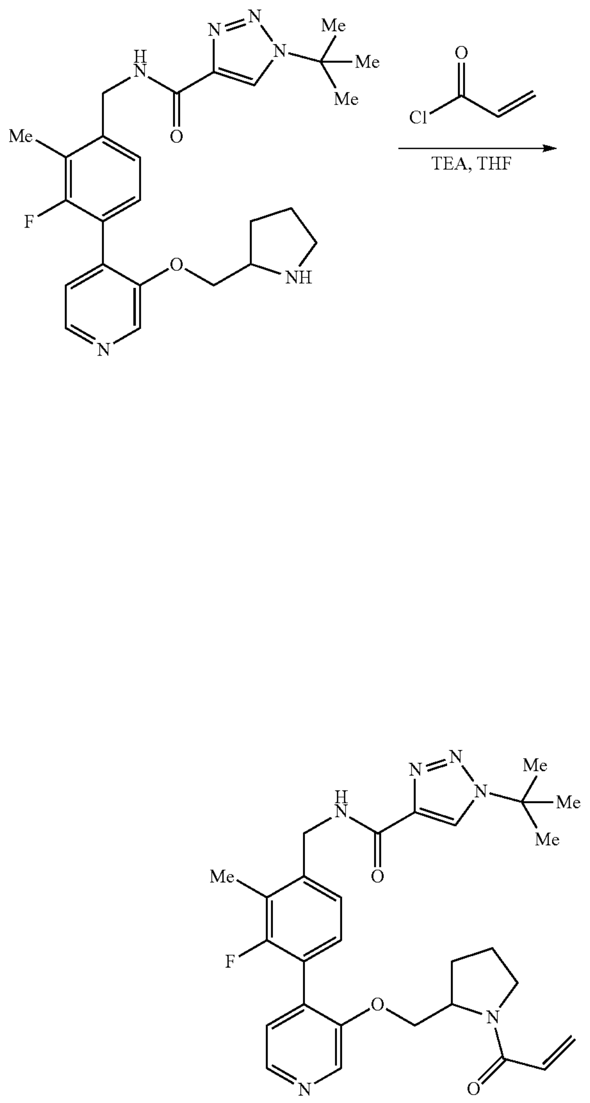

To a solution of Example 64, step 7:1-(tert-butyl)-N-(3-fluoro-2-methyl-4-(3-(pyrrolidin-2-ylmethoxy)pyridin-4-yl)benzyl)-1H-1,2,3-triazole-4-carboxamide (30 mg, 64.30 μmol) in THF (1 mL) was added acryloyl chloride (10.49 μL, 128.60 μmol), followed by TEA (17.83 μL, 128.60 μmol) and the reaction stirred at rt for 18 h. The reaction was evaporated under reduced pressure and the residue purified by Prep HPLC (Method D, organic gradient: 5-50%) to give N-(4-(3-((1-acryloylpyrrolidin-2-yl)methoxy)pyridin-4-yl)-3-fluoro-2-methylbenzyl)-1-(tert-butyl)-1H-1,2,3-triazole-4-carboxamide, 15.1 mg (43%) of an off-white solid. LCMS m/z=521.3 (M+H)+$^1$H NMR (500 MHz, DMSO-$d_6$) δ: 9.05 (t, 1H), 8.71 (s, 1H), 8.54-8.44 (m, 1H), 8.31-8.25 (m, 1H), 7.26 (d, 1H), 7.20-7.10 (m, 2H), 6.47 (dd, 1H), 6.14-5.96 (m, 1H), 5.62-5.41 (m, 1H), 4.51 (d, 2H), 4.32-4.00 (m, 4H), 3.23-3.13 (m, 1H), 2.28 (br s, 3H), 1.97-1.65 (m, 4H), 1.63 (s, 9H)

Example 50. 1-(tert-butyl)-N-(3-fluoro-2-methyl-4-(3-((1-(vinylsulfonyl)pyrrolidin-2-yl)methoxy)pyridin-4-yl)benzyl)-1H-1,2,3-triazole-4-carboxamide

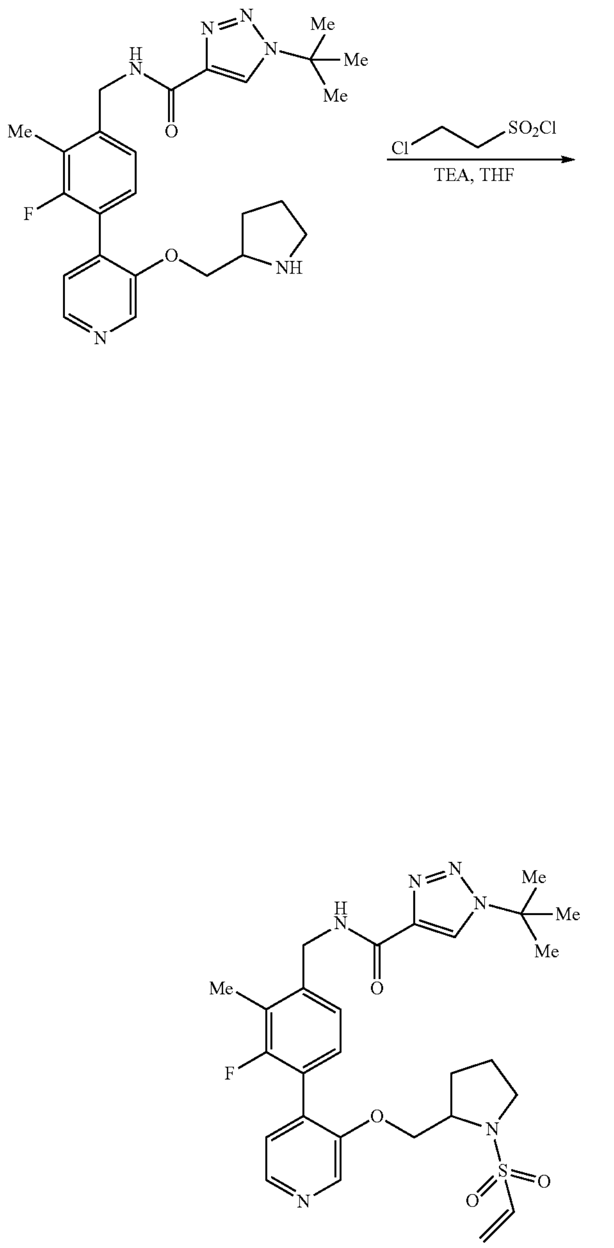

1-(tert-Butyl)-N-(3-fluoro-2-methyl-4-(3-((1-(vinylsμ-Lfonyl)pyrrolidin-2-yl)methoxy)pyridin-4-yl)benzyl)-1H-1,2,3-triazole-4-carboxamide was obtained as a yellowish solid, from Example 64, step 7:1-(tert-butyl)-N-(3-fluoro-2-methyl-4-(3-(pyrrolidin-2-ylmethoxy)pyridin-4-yl)benzyl)-1H-1,2,3-triazole-4-carboxamide and 2-chloroethanesulfonyl chloride following the procedure described in Example 49, 7.7 mg (20%). LCMS m/z=557.2 (M+H)+. $^1$H NMR (500 MHz, DMSO-$d_6$) δ: 9.04 (t, 1H), 8.70 (s, 1H), 8.46 (s, 1H), 8.29 (d, 1H), 7.28 (d, 1H), 7.20-7.16 (m, 2H), 6.87 (dd, 1H), 6.10 (s, 1H), 6.07 (d, 1H), 4.50 (d, 2H), 4.18-4.05 (m, 2H), 3.83 (br s, 1H), 3.11-2.90 (m, 2H), 2.28 (d, 3H), 1.87-1.74 (m, 2H), 1.63 (s, 9H), 1.63-1.57 (m, 2H).

Example 51. N-(4-(3-((1-acryloylpyrrolidin-3-yl) methoxy)pyridin-4-yl)-3-fluoro-2-methylbenzyl)-1-(tert-butyl)-1H-1,2,3-triazole-4-carboxamide 1. Synthesis of 1-(tert-butyl)-N-(3-fluoro-2-methyl-4-(3-(pyrrolidin-3-ylmethoxy)pyridin-4-yl)benzyl)-1H-1,2,3-triazole-4-carboxamide

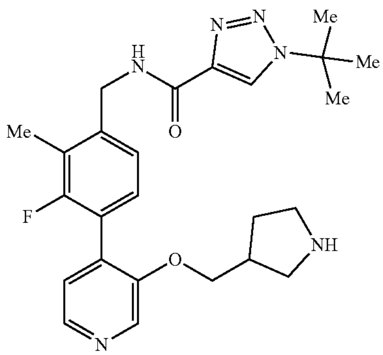 [SMILES: Cc1c(CNC(=O)c2cn(C(C)(C)C)nn2)ccc(-c2ccncc2OCC2CCNC2)c1F]

1-(tert-Butyl)-N-(3-fluoro-2-methyl-4-(3-(pyrrolidin-3-ylmethoxy)pyridin-4-yl)benzyl)-1H-1,2,3-triazole-4-carboxamide was obtained from tert-butyl 3-(((4-bromopyridin-3-yl)oxy)methyl)pyrrolidine-1-carboxylate and Intermediate 3, step 5: tert-butyl (3-fluoro-2-methyl-4-(4,4,5,5-tetramethyl-1,3,2-dioxaborolan-2-yl)benzyl)carbamate, following similar steps to that described in Example 64, steps 1 to 6.

2. Synthesis of N-(4-(3-((1-acryloylpyrrolidin-3-yl) methoxy)pyridin-4-yl)-3-fluoro-2-methylbenzyl)-1-(tert-butyl)-1H-1,2,3-triazole-4-carboxamide

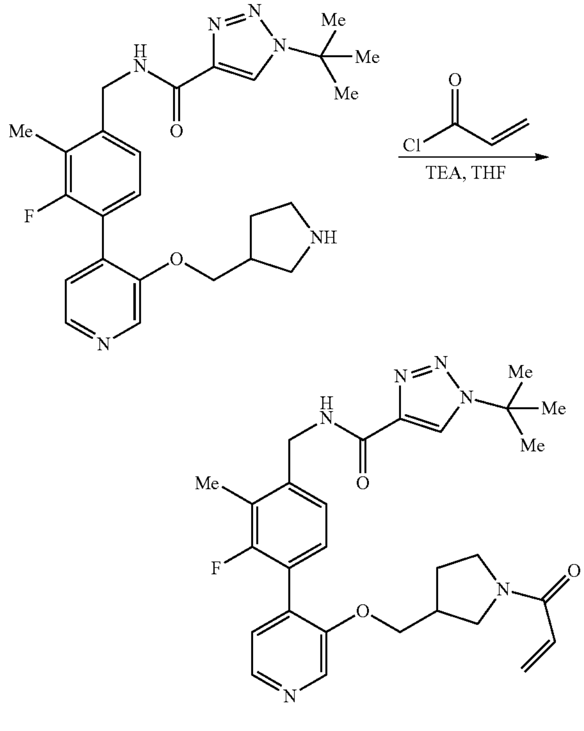

N-(4-(3-((1-Acryloylpyrrolidin-3-yl)methoxy)pyridin-4-yl)-3-fluoro-2-methylbenzyl)-1-(tert-butyl)-1H-1,2,3-triazole-4-carboxamide was obtained as an off-white solid, from 1-(tert-butyl)-N-(3-fluoro-2-methyl-4-(3-(pyrrolidin-3-ylmethoxy)pyridin-4-yl)benzyl)-1H-1,2,3-triazole-4-carboxamide and acryloyl chloride following the procedure described in Example 49, 15.1 mg, 43%. LCMS m/z=521.3 (M+H)+. $^1$H NMR (500 MHz, DMSO-$d_6$) δ: 9.04 (t, 1H), 8.71 (d, 1H), 8.48 (d, 1H), 8.28 (dd, 1H), 7.27-7.26 (m, 1H), 7.23-7.07 (m, 2H), 6.53-6.42 (m, 1H), 6.10 (ddd, 1H), 5.63 (dt, 1H), 4.51 (d, 2H), 4.24-4.00 (m, 2H), 3.65-3.41 (m, 2H), 3.16-3.12 (m, 1H), 2.69-2.56 (m, 1H), 2.28 (br s, 3H), 2.04-1.82 (m, 1H), 1.79-1.68 (m, 1H), 1.64 (s, 9H), 1.62-1.57 (m, 1H)

Example 52. (S)-N-(4-(3-((1-acryloylazetidin-2-yl) methoxy)pyridin-4-yl)-2-methylbenzyl)-6-(trifluoromethyl)nicotinamide

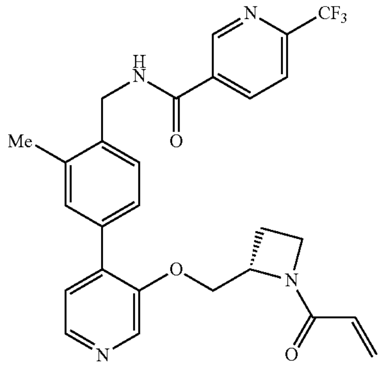 [SMILES: C=CC(=O)N1CC[C@H]1COc1cnccc1-c1ccc(CNC(=O)c2ccc(C(F)(F)F)nc2)c(C)c1]

1. Synthesis of tert-butyl (S)-2-(((4-bromopyridin-3-yl)oxy)methyl)azetidine-1-carboxylate

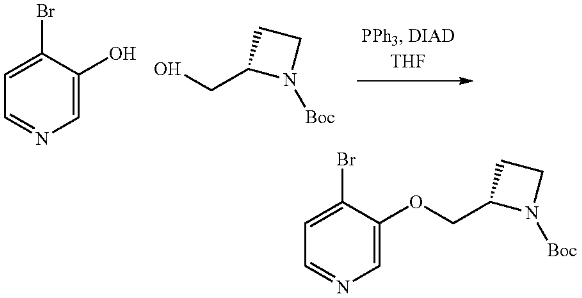

To a solution of 4-bromopyridin-3-ol (500 mg, 2.87 mmol) in THF (10 mL) was added $PPh_3$ (1.13 g, 4.31 mmol) and tert-butyl (2S)-2-(hydroxymethyl)azetidine-1-carboxylate (644.85 mg, 3.44 mmol) and the mixture was stirred at 15° C. for 6 min and then cooled to 0° C. DIAD (845.16 μL, 4.31 mmol) was added and the reaction stirred at 15° C. for 12 h. The reaction was filtered through Celite® and the filtrate concentrated in vacuo. The residue was purified by silica gel column chromatography eluting with heptanes/EtOAc (100/0 to 100/0) to give tert-butyl (S)-2-(((4-bromopyridin-3-yl)oxy)methyl)azetidine-1-carboxylate (671.80 mg, 64.79% yield). LCMS m/z=345.1 (M+H)+

2. Synthesis of (S)-3-(azetidin-2-ylmethoxy)-4-bromopyridine hydrochloride

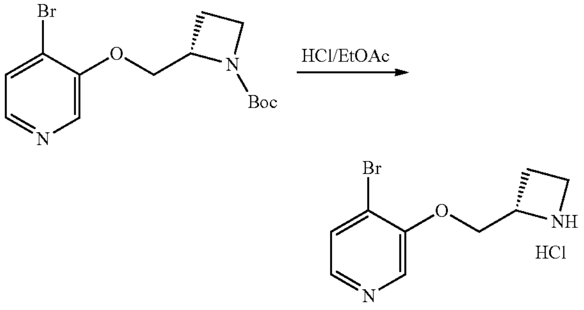

A solution of tert-butyl (S)-2-(((4-bromopyridin-3-yl)oxy)methyl)azetidine-1-carboxylate (133 mg, 387.51 μmol) in EtOAc (2 mL) and HCl (4 M, 290.63 μL) was stirred at 20° C. for 16 h. The reaction suspension was filtered and the solid dried to give (S)-3-(azetidin-2-ylmethoxy)-4-bromopyridine hydrochloride (93.50 mg, 86.31% yield). LCMS m/z=245.0 (M+H)+

3. Synthesis of (S)-1-(2-(((4-bromopyridin-3-yl)oxy)methyl)azetidin-1-yl)prop-2-en-1-one

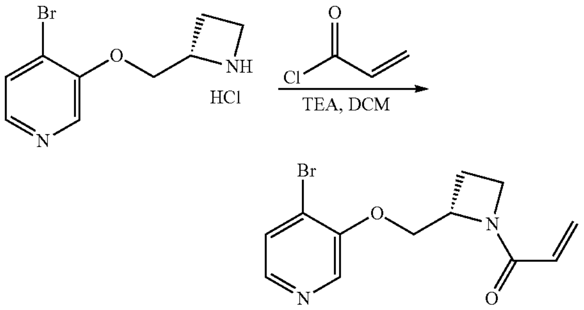

Acryloyl chloride (27.27 μL, 334.45 μmol) followed by TEA (92.73 μL, 668.90 μmol) were added dropwise to a solution of (S)-3-(azetidin-2-ylmethoxy)-4-bromopyridine hydrochloride (81.3 mg, 334.5 μmol) in DCM (2 mL) at 0° C. and the reaction then stirred at 0° C. for 2 h. The reaction was filtered and the filtrate purified directly by silica gel column chromatography eluting with DCM/MeOH (100/0 to 70/30) to give (S)-1-(2-(((4-bromopyridin-3-yl)oxy)methyl)azetidin-1-yl)prop-2-en-1-one (15 mg, 15.09% yield). LCMS m/z=297.0 (M+H)+

4. Synthesis of (S)-N-(4-(3-((1-acryloylazetidin-2-yl)methoxy)pyridin-4-yl)-2-methylbenzyl)-6-(trifluoromethyl)nicotinamide trifluoroacetate

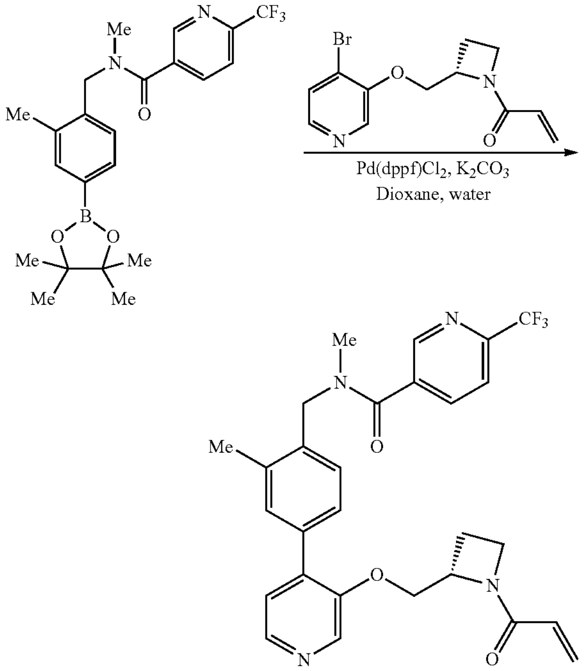

(S)-1-(2-(((4-bromopyridin-3-yl)oxy)methyl)azetidin-1-yl)prop-2-en-1-one (15 mg, 50.48 μmol), Intermediate 4: N-methyl-N-(2-methyl-4-(4,4,5,5-tetramethyl-1,3,2-dioxaborolan-2-yl)benzyl)-6-(trifluoromethyl)nicotinamide (24.11 mg, 55.53 μmol), $K_2CO_3$ (20.93 mg, 151.44 μmol) and Pd(dppf)$Cl_2$ (3.69 mg, 5.05 μmol) in dioxane (2 mL) and water (199.98 μL) was stirred at 90° C. for 2 h. The cooled solution was diluted with EtOAc, dried over $Na_2SO_4$ and concentrated in vacuo. The residue was purified by silica gel column chromatography eluting with (DCM/MeOH 100/0 to 70/30) to afford a yellow gel. This was further purified by prep HPLC (using a C18 column eluting with ($H_2O$:MeCN (with 0.1% TFA modifier), 0-70%) to afford (S)-N-(4-(3-((1-acryloylazetidin-2-yl)methoxy)pyridin-4-yl)-2-methylbenzyl)-6-(trifluoromethyl)nicotinamide trifluoroacetate (8.50 mg, 25.05% yield) as a white solid after lyophilization. LCMS m/z=525.2 (M+H)+. $^1$H NMR (400 MHz, MeOD-$d_4$) δ: 8.89 (br s, 1H), 8.74-8.66 (m, 1H), 8.53 (d, 1H), 8.28-8.09 (m, 1H), 8.04-7.85 (m, 2H), 7.71-7.54 (m, 2H), 7.47 (br d, 1H), 6.15 (d, 2H), 5.73-5.44 (m, 1H), 5.02-4.90 (m, 2H), 4.85-4.74 (m, 1H), 4.70-4.58 (m, 1H), 4.53-4.35 (m, 1H), 4.18-3.87 (m, 1H), 3.84-3.61 (m, 1H), 3.22-2.96 (m, 3H), 2.61-2.12 (m, 5H).

In Vitro BTK Kinase Assay: Btk-PolyGAT-LS Assay

The purpose of the BTK in vitro assay is to determine compound potency against BTK through the measurement of $IC_{50}$. Compound inhibition is measured after monitoring the amount of phosphorylation of a fluorescein-labeled polyGAT peptide (Invitrogen PV3611) in the presence of active BTK enzyme (Upstate 14-552), ATP, and inhibitor. The BTK kinase reaction was done in a black 96 well plate (costar 3694). For a typical assay, a 24 μL aliquot of a ATP/peptide master mix (final concentration; ATP 10 μM, polyGAT 100 nM) in kinase buffer (10 mM Tris-HCl pH 7.5, 10 mM MgCl2, 200 μM $Na_3PO_4$, 5 mM DTT, 0.01% Triton X-100, and 0.2 mg/ml casein) is added to each well. Next, I pL of a 4-fold, 40× compound titration in 100% DMSO solvent is added, followed by adding 15 μL of BTK enzyme mix in 1× kinase buffer (with a final concentration of 0.25 nM). The assay is incubated for 30 minutes before being stopped with 28 μL of a 50 mM EDTA solution. Aliquots (5 μL) of the kinase reaction are transferred to a low volume white 384 well plate (Corning 3674), and 5 pL of a 2× detection buffer (Invitrogen PV3574, with 4 nM Tb-PY20 antibody, Invitrogen PV3552) is added. The plate is covered and incubated for 45 minutes at room temperature. Time resolved fluorescence (TRF) on Molecular Devices M5 (332 nm excitation; 488 nm emission; 518 nm fluorescein emission) is measured. $IC_{50}$ values are calculated using a four parameter fit with 100% enzyme activity determined from the DMSO control and 0% activity from the EDTA control.

Table 2 shows the activity of selected compounds of this invention in the in vitro Btk kinase assay, wherein each compound number corresponds to the compound numbering set forth in Examples 1-30 described herein.

"†" represents an $IC_{50}$ of greater than 10 nM (10 nM<$IC_{50}$).

"††" represents an $IC_{50}$ of greater than 1 nM and equal to or less than 10 nM (1 nM<$IC_{50}$≤10 nM).

"†††" represents an $IC_{50}$ of equal to or less than 1 nM ($IC_{50}$≤1 nM)

TABLE 2

| $IC_{50}$ (nM) | Example No. |
|---|---|
| † | 34, 35, 38, 39, 40, 41, 45, 46, 47, 52 |
| †† | 15, 30, 33, 36, 43, 48, 49 |
| ††† | 1, 2, 3, 4, 5, 6, 7, 8, 9, 10, 11, 12, 13, 14, 16, 17, 29, 31, 32, 37, 42, 44, 50, 51 |

In Vitro Whole Blood CD69 Assay

Human heparinized venous blood from health donors was aliquoted into 96-well plate and "spiked" with serial dilutions of formula I compounds in DMSO or with DMSO without drug. The final concentration of DMSO in all wells was 0.1%. The plate was incubated at 37° C. for 30 min. Drug-containing samples were stimulated with 0.1 μg/mL mouse anti-human IgD-dextran (1A62) or 20 μg/mL polyclonal rabbit F(ab')2 anti-human IgD. Phosphate-buffered saline (PBS) was added to the negative control unstimulated sample and the plates were incubated overnight (18 to 22 hours) at 37° C. Cells were stained with fluorochrome-conjugated anti-CD19 and anti-CD69 antibodies. Lyse/fix solution was used to remove red blood cells by hypotonic lysis and to fix the remaining cells, which were then analyzed by flow cytometry. CD19+ B cells were gated and analyzed for CD69 expression. The percentage of B cells expressing CD69 was plotted versus the log 10 of the concentration of the drug and the best-fit curves (variable Hill slope) were generated to obtain the IC50 value.

Table 3 shows the activity of selected compounds of this invention in the Whole Blood CD69 inhibition assay, wherein each compound number corresponds to the compound numbering set forth in Examples 1-28 described herein.

"*" represents an $IC_{50}$ of greater than 1 μM (1 μM<$IC_{50}$).

"**" represents an $IC_{50}$ of greater than 0.1 μM and equal to or less than 1 μM (0.1 μM<$IC_{50}$≤1 μM).

"***" represents an $IC_{50}$ of equal to or less than 0.1 μM ($IC_{50}$≤0.1 μM)

TABLE 3

| $IC_{50}$ (nM) | Compound No. |
|---|---|
| * | 33, 35, 36, 37, 38, 39, 40, 41, 43, 44, 49, 50 |
| ** | 11, 12, 42, |
| *** | 1, 2, 3, 4, 5, 6, 7, 8, 9, 10, 31, 32 |

Other Embodiments

All of the features disclosed in this specification may be combined in any combination. Each feature disclosed in this specification may be replaced by an alternative feature serving the same, equivalent or similar purpose. Thus, unless expressly stated otherwise, each feature disclosed is only an example of a series of equivalent or similar features.

From the above description, one skilled in the art can easily ascertain the essential characteristics of the present invention, and without departing from the spirit and scope thereof, can make various changes and modifications of the invention to adapt it to various usage and conditions. Thus, other embodiments are also within the scope of the following claims.

What is claimed is:

1. A compound represented by Formula (I'):

(I')

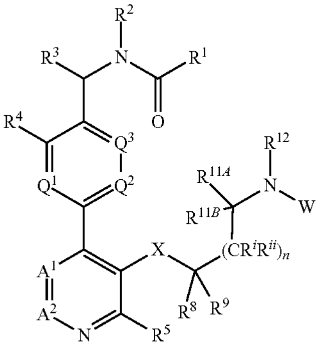

or a pharmaceutically acceptable salt thereof, wherein:

one of $A^1$ and $A^2$ is C—$R^6$, and the other of $A^1$ and $A^2$ is C—$R^6$ or N;

$Q^1$ is selected from C—$R^6$ and N;

$Q^2$ is selected from C—$R^6$ and N;

$Q^3$ is selected from C—$R^6$ and N;

wherein at most one of $Q^1$, $Q^2$, and $Q^3$ is N;

$R^1$ is a 3- to 7-membered saturated or partially unsaturated monocyclic heterocyclyl having 1-2 heteroatoms independently selected from O, N and S, or a 5- to 6-membered heteroaryl having 1-4 heteroatoms independently selected from O, N and S, wherein the 3- to 7-membered saturated or partially unsaturated monocyclic heterocyclyl and 5- to 6-membered heteroaryl represented by $R^1$ are optionally substituted with one or two $R^{10}$ $R^{10}$, for each occurrence, is independently selected from halogen, —$OR^{10a}$, —$S(O)_2R^{10a}$, —CN, $C_{1-6}$ alkyl, $C_{2-6}$ alkenyl, $C_{2-6}$ alkynyl, 3- to 7-membered saturated or partially unsaturated monocyclic carbocyclyl, and 4- to 6-membered saturated or partially unsaturated monocyclic heterocyclyl; wherein the $C_{1-6}$ alkyl, $C_{2-6}$ alkenyl, $C_{2-6}$ alkynyl, 3- to 7-membered saturated or partially unsaturated monocyclic carbocyclyl, and 4- to 6-membered saturated or partially unsaturated monocyclic heterocyclyl represented by $R^{10}$ are each optionally substituted with one or more $R^{15}$;

$R^{10a}$ is $C_{1-6}$ alkyl optionally substituted with one ore more halogen;

$R^{15}$, for each occurrence, is independently selected from halogen and —$OR^{15a}$;

$R^{15a}$ is $C_{1-6}$ alkyl;

$R^2$ is H, $C_{1-6}$ alkyl, $C_{2-6}$ alkenyl, and $C_{2-6}$ alkynyl, or $R^1$ and $R^2$, together with their intervening atoms, form a Ring B selected from 3- to 7-membered saturated or partially unsaturated monocyclic heterocyclyl, 7- to 10-membered saturated or partially unsaturated bicyclic heterocyclyl, and 7- to 10-membered bicyclic heteroaryl, wherein Ring B is optionally substituted with one or more $R^{100}$;

$R^{100}$, for each occurrence, is independently selected from $C_{1-6}$ alkyl, $C_{2-6}$ alkenyl, $C_{2-6}$ alkynyl, 3- to 7-membered saturated or partially unsaturated monocyclic carbocyclyl, 4- to 6-membered saturated or partially unsaturated monocyclic heterocyclyl and halogen; wherein the $C_{1-6}$ alkyl, $C_{2-6}$ alkenyl, $C_{2-6}$ alkynyl, 3- to 7-membered saturated or partially unsaturated monocyclic carbocyclyl, and saturated or partially unsaturated 4- to 6-membered monocyclic heterocyclyl represented by $R^{100}$ are each optionally substituted with one or more $R^{150}$;

$R^{150}$, for each occurrence, is independently selected from halogen and —$OR^{150a}$;

$R^{150a}$ is $C_{1-6}$ alkyl;

$R^3$ is selected from H, halogen, —C(O)N($R^{3a}$) 2, —C(O)$OR^{3a}$,—C(O)$R^{3a}$, $C_{1-6}$ alkyl, $C_{2-6}$ alkenyl, and $C_{2-6}$ alkynyl, wherein the $C_{1-6}$ alkyl, $C_{2-6}$ alkenyl, and $C_{2-6}$ alkynyl represented by $R^3$ are each optionally substituted with one or more substituents selected from halogen and hydroxyl;

$R^{3a}$, for each occurrence, is independently selected from H, $C_{1-6}$ alkyl, $C_{2-6}$ alkenyl, $C_{2-6}$ alkynyl, phenyl, 3- to 7-membered saturated or partially unsaturated carbocyclyl ring, 3- to 7-membered saturated or partially unsaturated monocyclic heterocyclyl, or 5- to 6-membered heteroaryl, wherein $C_{1-6}$ alkyl, $C_{2-6}$ alkenyl, $C_{2-6}$ alkynyl, phenyl, 3- to 7-membered saturated or partially unsaturated carbocyclyl ring, 3- to 7-membered saturated or partially unsaturated monocyclic heterocyclyl, and 5- to 6-membered heteroaryl are optionally substituted with one or more $R^{30}$;

or two $R^{3a}$ groups on the same nitrogen are taken together with their intervening atoms to form a ring selected from 3- to 7-membered saturated or partially unsaturated monocyclic heterocyclyl and 5- to 6-membered heteroaryl, wherein said ring is optionally substituted with one or more $R^{30}$;

$R^{30}$, for each occurrence, is independently selected from halogen, —$OR^{30a}$, —N($R^{30a}$)$_2$, —C(O)N($R^{30a}$), —C(O)$_2R^{30a}$, oxo, $C_{1-6}$ alkyl, $C_{2-6}$ alkenyl, $C_{2-6}$ alkynyl, 3- to 7-membered saturated or partially unsaturated monocyclic carbocyclyl, and 4- to 6-membered saturated or partially unsaturated monocyclic heterocyclyl;

$R^{30a}$ is H or $C_{1-6}$ alkyl;

$R^4$ is selected from H, halogen, —$NO_2$, —CN, —$OR^{4a}$, —$SR^{4a}$, —N($R^{4a}$)$_2$, —C(O)$R^{4a}$, —C(O)$OR^{4a}$, —S(O)$R^{4a}$, —S(O)$_2R^{4a}$, —C(O)N($R^{4a}$)$_2$, —$SO_2$N($R^{4a}$)$_2$, —OC(O)$R^{4a}$, —N($R^{4a}$)C(O)$R^{4a}$, —N($R^{4a}$)C(O)$OR^{4a}$, N($R^{4a}$)$SO_2R^{4a}$, —OC(O)N($R^{4a}$)$_2$, $C_{1-6}$ alkyl, $C_{2-6}$ alkenyl and $C_{2-6}$ alkynyl, wherein the $C_{1-6}$ alkyl, $C_{2-6}$ alkenyl and $C_{2-6}$ alkynyl are each optionally substituted with one ore more $R^{40}$;

$R^{4a}$ is H, $C_{1-6}$ alkyl, $C_{2-6}$ alkenyl, $C_{2-6}$alkynyl, phenyl, 3- to 8-membered saturated or partially unsaturated carbocyclyl ring, 3- to 7-membered saturated or partially unsaturated monocyclic heterocyclyl, and 5- to 6-membered heteroaryl, wherein the $C_{1-6}$ alkyl, $C_{2-6}$ alkenyl, $C_{2-6}$ alkynyl, phenyl, 3- to 8-membered saturated or partially unsaturated carbocyclyl ring, 3- to 7-membered saturated or partially unsaturated monocyclic heterocyclyl, and 5- to 6-membered heteroaryl represented by $R^{4a}$ are each optionally substituted with one or more $R^{40}$;

or two $R^{4a}$ groups on the same nitrogen are taken together with their intervening atoms to form a ring selected from 3- to 7-membered saturated or partially unsaturated monocyclic heterocyclyl and 5- to 6-membered heteroaryl, wherein said ring is optionally substituted with one or more $R^{40}$;

$R^{40}$, for each occurrence, is independently selected from halogen, —$OR^{40a}$, —N($R^{40a}$)$_2$, —C(O)N($R^{40a}$)$_2$, —C(O)$_2R^{40a}$, oxo, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl; wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{40}$ are each optionally substituted with one or more $R^{45}$;

$R^{40a}$ is H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3-to 7-membered monocyclic carbocyclyl, and 4- to 6-membered monocyclic heterocyclyl are each optionally substituted with one or more $R^{45}$;

$R^{45}$, for each occurrence, is independently selected from $C_{1-6}$ alkyl, halogen and —$OR^{45a}$;

$R^{45a}$ is H or $C_{1-6}$ alkyl;

or $R^3$ and $R^4$, together with their intervening atoms, form a Ring A, wherein Ring A is selected from 5- to 7-membered monocyclic carbocycle and 5- to 7-membered monocyclic heterocycle, wherein Ring A is optionally substituted with $R^{300}$;

$R^{300}$, for each occurrence, is independently selected from $C_{1-6}$ alkyl, $C_{2-6}$ alkenyl, $C_{2-6}$ alkynyl, 3- to 7-membered monocyclic carbocyclyl, 4- to 6-membered monocyclic heterocyclyl, halogen, —C(O)$R^{300a}$, —$OR^{300a}$, and —S(O)$_2R^{300a}$; wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{300}$ are each optionally substituted with one or more $R^{350}$;

$R^{300a}$ is selected from H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl represented by $R^{300a}$ are each optionally substituted with one or more $R^{350}$;

$R^{350}$, for each occurrence, is independently selected from $C_{1-6}$ alkyl, halogen, —CN, —C(O)$R^{350a}$, —C(O)N($R^{350a}$)$_2$, —C($R^{350a}$)$_2$N($R^{350a}$)$_2$, and —O$R^{350a}$;

$R^{350a}$, for each occurrence, is independently H or $C_{1-6}$ alkyl optionally substituted with one to three halogen;

$R^5$ is selected from H, —NH$R^7$, or —NHC(O)$R^7$;

$R^6$, for each occurrence, is independently selected from H, $C_{1-6}$ alkyl, $C_{2-6}$ alkenyl, $C_{2-6}$ alkynyl, halogen, —$NO_2$, —CN, —O$R^{6a}$, —S$R^{6a}$, —N($R^{6a}$)$_2$, —C(O)$R^{6a}$, —C(O)O$R^{6a}$, —S(O)$R^{6a}$, —S(O)$_2R^{6a}$, —C(O)N($R^{6a}$)$_2$, —$SO_2$N($R^{6a}$)$_2$, —OC(O)$R^{6a}$, —N($R^{6a}$)C(O)$R^{6a}$, —N($R^{6a}$) C(O)O$R^{6a}$, —N($R^{6a}$) $SO_2R^{6a}$, and —OC(O)N($R^{6a}$);

$R^{6a}$ is H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3- to 7-membered monocyclic carbocyclyl and 4- to 6-membered monocyclic heterocyclyl represented by $R^{6a}$ are each optionally substituted with one or more $R^{60}$;

$R^{60}$, for each occurrence, is independently selected from halogen, —O$R^{60a}$, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl; wherein the $C_{1-6}$ alkyl, $C_{2-6}$ alkenyl, $C_{2-6}$ alkynyl, 3- to 7-membered monocyclic carbocyclyl and 4- to 6-membered monocyclic heterocyclyl represented by $R^{60}$ are optionally substituted with one or more $R^{65}$;

$R^{60a}$ is H, $C_{1-6}$ alkyl, $C_{2-6}$ alkenyl, $C_{2-6}$ alkynyl, 3- to 7-membered monocyclic carbocyclyl, and 4- to 6-membered monocyclic heterocyclyl, wherein the $C_{1-6}$ alkyl, $C_{2-6}$ alkenyl, $C_{2-6}$ alkynyl, 3-to 7-membered monocyclic carbocyclyl, and 4- to 6-membered monocyclic heterocyclyl represented by $R^{60a}$ are each optionally substituted with one or more $R^{65}$;

$R^{65}$, for each occurrence, is independently selected from $C_{1-6}$ alkyl, halogen and —O$R^{65a}$, $R^{65a}$ is H or $C_{1-6}$ alkyl;

$R^7$ is H or $C_{1-6}$ alkyl;

X is $CR^{15}R^{16}$, O, $NR^{14}$, S, SO or $SO_2$;

$R^8$, $R^9$, $R^i$, $R^{ii}$, $R^{11A}$ and $R^{11B}$ are each independently H or $C_{1-6}$ alkyl optionally substituted with one or more substituents independently selected from halogen and $C_{1-6}$ alkoxy; or any two of $R^8$, $R^9$, $R^i$, $R^{ii}$, $R^{11A}$ and $R^{11B}$ together with the carbon atom to which they are bound form a 3-8 membered saturated carbocyclic ring;

or alternatively, $R^8$ and $R^9$ together with the carbon atom from which they are attached form a carbonyl —C(═O)— group;

$R^{12}$ is H or $C_{1-6}$ alkyl optionally substituted with one or more substituents independently selected from halogen and $C_{1-6}$ alkoxy;

or $R^{12}$ and any one of $R^8$, $R^9$, $R^i$, $R^{ii}$, $R^{11A}$ and $R^{11B}$ together with the atoms to which they are bound form a 4 to 8-membered azacyclic ring, which ring is optionally substituted with one or more substituents independently selected from halogen, —CN, —OH, $C_{1-6}$ alkyl and $C_{1-6}$ alkoxy;

n is 0 or 1;

W is —C(═O)—$R^{13}$, —$SO_2$—$R^{13}$, or —CN;

$R^{13}$ is $C_{2-6}$ alkenyl, $C_{2-6}$ alkynyl or $C_{2-6}$ alkylenyl oxide, wherein the $C_{2-6}$ alkenyl represented by $R^{13}$ is optionally substituted with one or more substituents independently selected from $C_{1-6}$ alkyl, $C_{1-6}$ alkoxy and —$NR^{13a}R^{13b}R^{13b}$, the $C_{2-6}$ alkynyl represented by $R^{13}$ is optionally substituted by one or more substituents independently selected from $C_{1-6}$ alkyl and $C_{1-6}$ alkoxy, and the $C_{2-6}$ alkylenyl oxide represented by $R^{13}$ is optionally substituted by one or more $C_{1-6}$ alkyl;

$R^{13a}$ and $R^{13b}$ are each independently H or $C_{1-3}$ alkyl;

$R^{14}$ is H or $C_1$-$C_6$ alkyl; and $R^{15}$ and $R^{16}$ are each independently H, $C_{1-6}$alkyl, halogen, or $C_{1-6}$alkoxy, wherein the $C_{1-6}$alkyl and $C_{1-6}$alkoxy are each optionally substituted with one or more halogen.

2. The compound of claim 1, wherein the compound is represented by Formula (I):

(I)

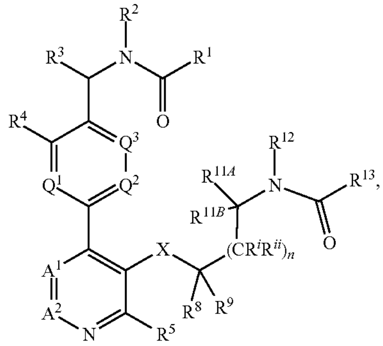

or a pharmaceutically acceptable salt thereof, wherein:

$R^8$, $R^9$, $R^i$, $R^{ii}$, $R^{11A}$ and $R^{11B}$ are each independently H or $C_{1-6}$ alkyl optionally substituted with one or more substituents independently selected from halogen and $C_{1-6}$ alkoxy; or any two of $R^8$, $R^9$, $R^i$, $R^{ii}$, $R^{11A}$ and $R^{11B}$ together with the carbon atom to which they are bound form a 3-6 membered saturated carbocyclic ring; and $R^{12}$ is H or $C_{1-6}$ alkyl optionally substituted with one or more substituents independently selected from halogen and $C_{1-6}$ alkoxy;

or $R^{12}$ and any one of $R^8$, $R^9$, $R^i$, $R^{ii}$, $R^{11A}$ and $R^{11B}$ together with the atoms to which they are bound form a 4 to 7-membered azacyclic ring, which ring is optionally substituted with one or more substituents independently selected from halogen, —CN, —OH, $C_{1-6}$ alkyl and $C_{1-6}$ alkoxy.

3. The compound of claim 2, or a pharmaceutically acceptable salt thereof, wherein (i) $Q^1$, $Q^2$ and $Q^3$ are C—$R^6$; (ii) $A^1$ is N and $A^2$ is C—$R^6$; or (iii) $A^1$ and $A^2$ are both C—$R^6$.

4. The compound of claim 2, wherein the compound is represented by Formula (II) or Formula (III):

(II)

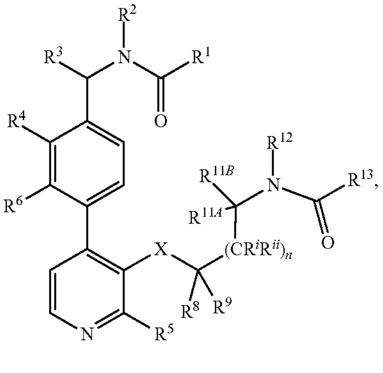

or

-continued (III)

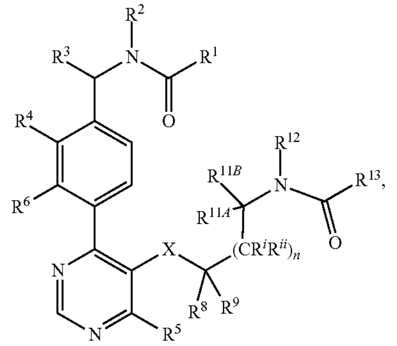

or a pharmaceutically acceptable salt thereof.

5. The compound of claim 1, or a pharmaceutically acceptable salt thereof, wherein $R^1$ is represented by the following formula:

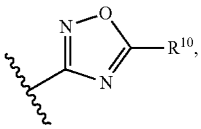,
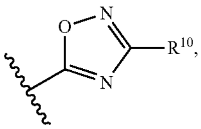,
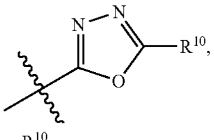,
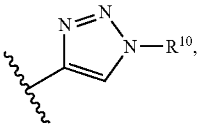,
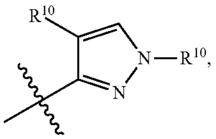,
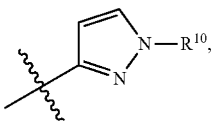,
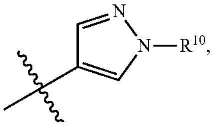,
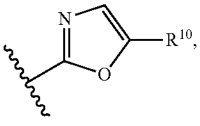,
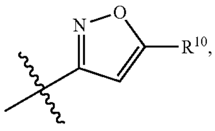,
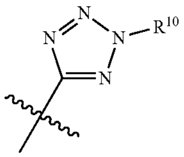,
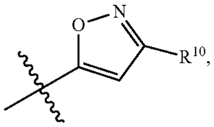,
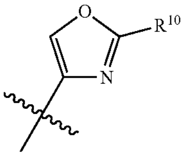 or
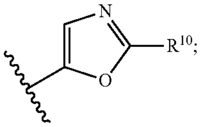;

$R^{10}$, for each occurrence, is independently selected from halogen, $-OR^{10a}$, $-S(O)_2R^{10a}$, $-CN$, $C_{1-6}$ alkyl, $C_{3-6}$ cycloalkyl, and phenyl; wherein the $C_{1-6}$ alkyl, $C_{3-6}$ cycloalkyl, and phenyl represented by $R^{10}$ are each optionally substituted with one to three $R^{15}$;

$R^{10a}$, for each occurrence, is independently selected from H and $C_{1-3}$ alkyl;

$R^{15}$, for each occurrence, is independently selected from $C_{1-6}$alkyl, halogen, $-CN$ and $-OR^{15a}$; and $R^{15a}$ is H or $C_{1-3}$ alkyl.

6. The compound of claim 4, or a pharmaceutically acceptable salt thereof, wherein $R^2$ is H or $C_{1-3}$ alkyl; and $R^3$ is H.

7. The compound of claim 4, or a pharmaceutically acceptable salt thereof, wherein $R^1$ and $R^2$, together with their intervening atoms, form a Ring B selected from 3- to 7-membered saturated or partially unsaturated monocyclic heterocyclyl having 1-2 heteroatoms independently selected from O, N and S, 5- to 6-membered heteroaryl having 1-4 heteroatoms independently selected from O, N and S, 7- to 10-membered bicyclic heterocyclyl having 1-4 heteroatoms independently selected from O, N and S, and 7- to 10-membered bicyclic heteroaryl having 1-4 heteroatoms independently selected from O, N and S, wherein Ring B is optionally substituted with one or two $R^{100}$.

8. The compound of claim 7, or a pharmaceutically acceptable salt thereof, wherein Ring B is represented by one of following formulae:

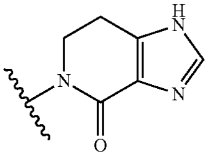,
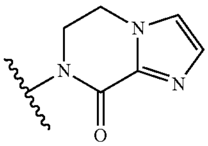,
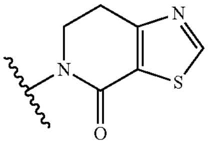,
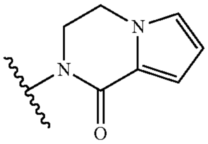,
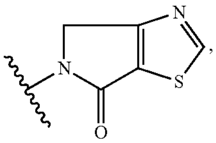,
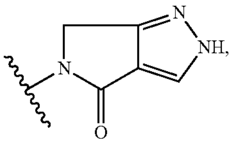
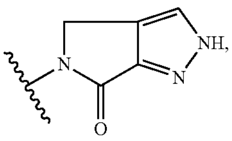
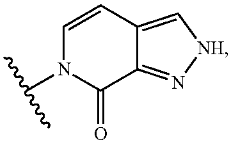
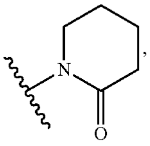,
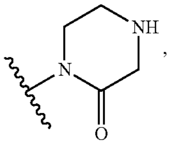,
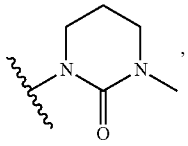,
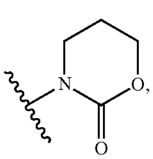
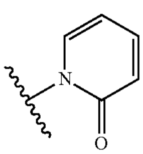,
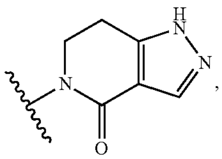,
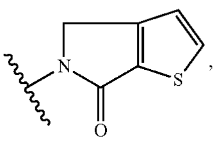,
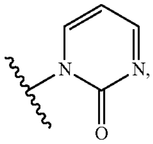 or -continued

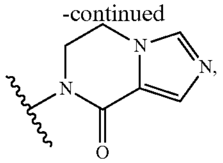

wherein Ring B is optionally substituted with one or two $R^{100}$; wherein:

$R^{100}$, for each occurrence, is independently selected from $C_{1-6}$ alkyl, $C_{3-6}$ cycloalkyl, halogen, —CN, and —$OR^{100a}$; wherein the $C_{1-6}$ alkyl and $C_{3-6}$ cycloalkyl are each optionally substituted with one to three substituents independently selected from halogen and $C_{1-3}$ alkyl; $R^{100a}$ for each occurrence, is independently selected from H, $C_{1-6}$ alkyl, $C_{3-6}$ cycloalkyl, and 4- to 6-membered monocyclic heterocyclyl.

9. The compound of claim 4, or a pharmaceutically acceptable salt thereof, wherein:

$R^4$ is selected from H, halogen, —CN, —$OR^{4a}$, $C_{1-6}$ alkyl, and $C_{3-6}$ cycloalkyl, wherein the $C_{1-6}$ alkyl and $C_{3-6}$ cycloalkyl represented by $R^4$ are each optionally substituted with one to three halogen; and $R^{4a}$ is $C_{1-4}$ alkyl optionally substituted with one to three halogen; and $R^6$ is H or halogen.

10. The compound of claim 4, or a pharmaceutically acceptable salt thereof, wherein $R^3$ and $R^4$, together with their intervening atoms, form a Ring A, wherein Ring A is selected from 5- to 7-membered monocyclic carbocycle and 5- to 7-membered monocyclic heterocycle, wherein Ring A is optionally substituted with $R^{300}$.

11. The compound of claim 4, or a pharmaceutically acceptable salt thereof, wherein $R^5$ is H or —$NHR^7$; and $R^7$ is H or $C_{1-3}$ alkyl.

12. The compound of claim 4, or a pharmaceutically acceptable salt thereof, wherein X is O or $NR^{14}$, wherein $R^{14}$ is H or methyl.

13. The compound of claim 4, or a pharmaceutically acceptable salt thereof, wherein n is O; and $R^8$, $R^9$, $R^{11A}$ and $R^{11B}$ are each independently H or $C_{1-3}$ alkyl, $R^{12}$ is H or $C_{1-3}$ alkyl; and $R^{13}$ is $C_{2-6}$ alkenyl optionally substituted with $C_{1-6}$ alkyl, $C_{1-6}$ alkoxy or —$NR^{13a}R^{13b}$ and $R^{13a}$ and $R^{13b}$ are each independently H or $C_{1-3}$ alkyl.

14. The compound of claim 4, or a pharmaceutically acceptable salt thereof, wherein:

(i) $R^{12}$ and any one of $R^{11A}$ and $R^{11B}$ together with the atoms to which they are bound form a 4 to 8-membered azacyclic ring, wherein the 4 to 8-membered azacyclic ring is optionally substituted with one to three substituents independently selected from halogen, —CN, —OH, $C_{1-6}$ alkyl and $C_{1-6}$ alkoxy;

(ii) $R^{12}$ and any one of $R^i$ and $R^{ii}$ together with the atoms to which they are bound form a 4 to 7-membered azacyclic ring, wherein the 4 to 7-membered azacyclic ring is optionally substituted with one to three substituents independently selected from halogen, —CN, —OH, $C_{1-6}$ alkyl and $C_{1-6}$ alkoxy; or (iii) $R^{12}$ and any one of $R^8$ and $R^9$ together with the atoms to which they are bound form a 4 to 7-membered azacyclic ring, which ring is optionally substituted with one to three substituents independently selected from halogen, —CN, —OH, $C_{1-6}$ alkyl and $C_{1-6}$ alkoxy.

15. The compound of claim 2, wherein the compound is represented by the following formula:

(IIA)

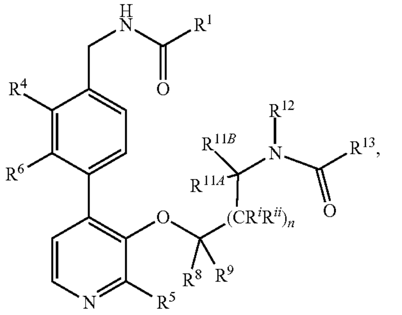

or (IIIA)

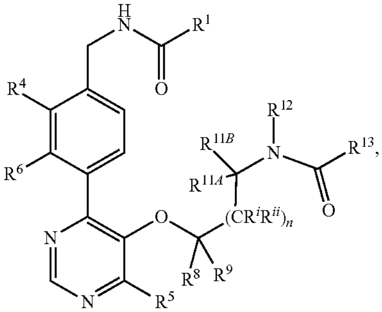

or a pharmaceutically acceptable salt thereof, wherein:

$R^1$ is represented by the following formula:

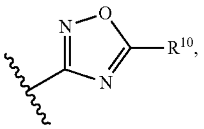
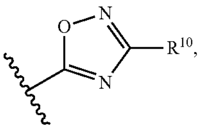
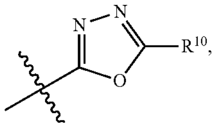
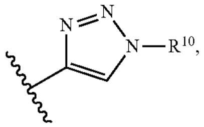
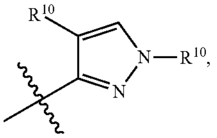
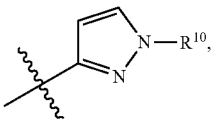
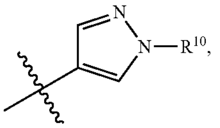
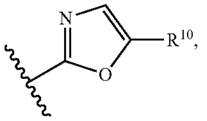
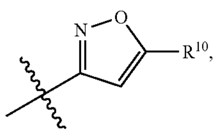
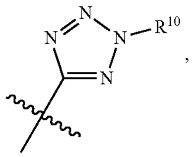
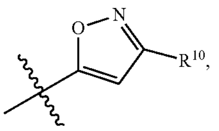
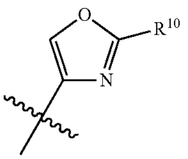

or

-continued

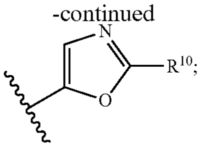

$R^{10}$, for each occurrence, is independently $C_{1-6}$ alkyl optionally substituted with one to three halogen;

$R^4$ is selected from H, halogen, —$OR^{4a}$ and $C_{1-6}$ alkyl optionally substituted with one or three halogen;

$R^{4a}$ is $C_{1-4}$ alkyl optionally substituted with one or three halogen;

$R^5$ is H or —$NH_2$;

$R^6$ is H or halogen;

$R^8$, $R^9$, $R^i$, $R^{ii}$, $R^{11A}$ and $R^{11B}$ are each independently H or $C_{1-3}$ alkyl;

$R^{12}$ is $C_{1-3}$ alkyl;

or $R^{12}$ and any one of $R^8$ and $R^9$ together with the atoms to which they are bound form a 4 to 7-membered azacyclic ring, which ring is optionally substituted with one or more substituents independently selected from halogen, —CN, —OH, $C_{1-6}$ alkyl and $C_{1-6}$ alkoxy; and $R^{13}$ is $C_{2-6}$ alkenyl optionally substituted with $C_{1-6}$ alkyl, $C_{1-6}$ alkoxy or —$NR^{13a}R^{13b}$, and $R^{13a}$ and $R^{13b}$ are each independently H or $C_{1-3}$ alkyl.

16. The compound of claim 1, wherein the compound is represented by the following formula:

(IIB)

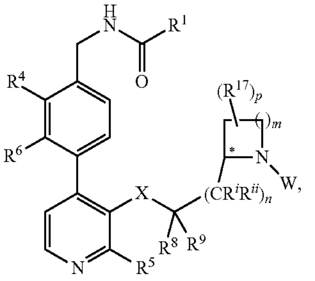

(IIIB)

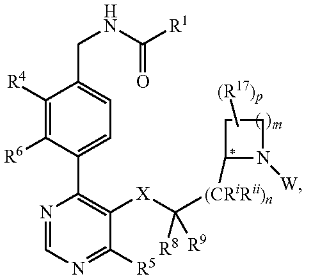

(IIC)

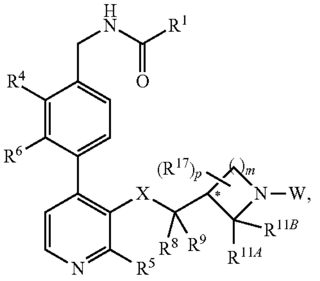

-continued (IIIC)

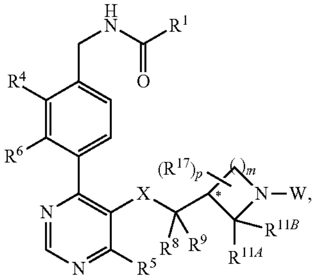

(IID)

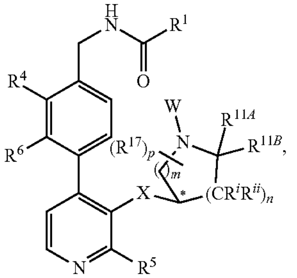

or (IIID)

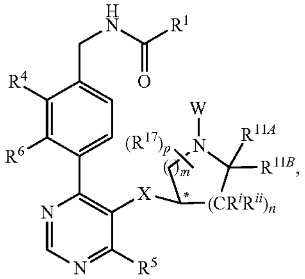

or a pharmaceutically acceptable salt thereof, wherein:

$R^1$ is represented by the following formula:

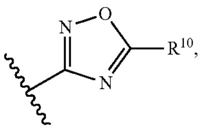
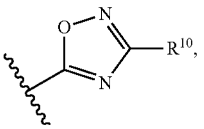
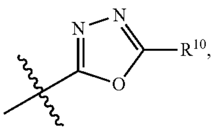
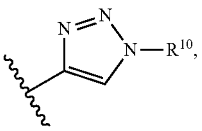
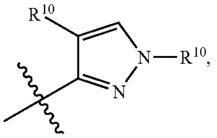
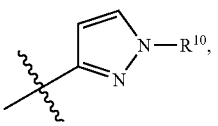
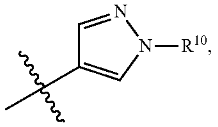
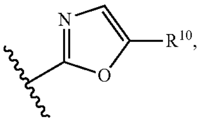

-continued

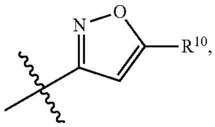 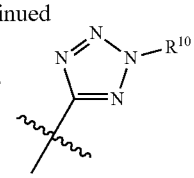 ,

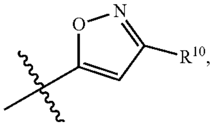 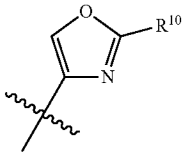 ,

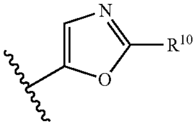 or 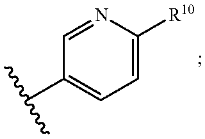 ;

$R^4$ is selected from H, halogen, —$OR^{4a}$ and $C_{1-6}$ alkyl optionally substituted with one or three halogen;

$R^{4a}$ is $C_{1-4}$ alkyl optionally substituted with one or three halogen;

$R^5$ is H or —$NH_2$;

$R^6$ is H or halogen;

$R^8$, $R^9$, $R^i$, $R^{ii}$, $R^{11A}$ and $R^{11B}$ are each independently H or $C_{1-3}$ alkyl;

or alternatively, $R^8$ and $R^9$ together with the carbon atom from which they are attached form a carbonyl —C(═O)— group;

$R^{10}$, for each occurrence, is independently $C_{1-6}$ alkyl optionally substituted with one to three halogen;

$R^{13}$ is $C_{2-6}$ alkenyl or $C_{2-6}$ alkynyl, wherein each of the $C_{2-6}$ alkenyl or the $C_{2-6}$ alkynyl represented by $R^{13}$ is optionally substituted with $C_{1-6}$ alkyl, $C_{1-6}$ alkoxy or —$NR^{13a}R^{13b}$;

$R^{13a}$ and $R^{13b}$ are each independently H or $C_{1-3}$ alkyl;

$R^{17}$ is halogen, —CN, —OH, $C_{1-6}$ alkyl or $C_{1-6}$ alkoxy;

X is $CR^{15}R^{16}$, O, $NR^{14}$, S, SO or $SO_2$;

W is —C(═O)—$R^{13}$, —$SO_2$—$R^{13}$, or —CN;

m is 1, 2, 3 or 4;

n is 0 or 1; and p is 0, 1, 2 or 3.

17. The compound of claim 16, or a pharmaceutically acceptable salt thereof, wherein:

the compound is represented by the formula IIB, IIIB, IIC, IIIC, IID or IIID and the absolute stereochemistry at the carbon atom marked by "*" is S, or the compound is represented by the formula IIB, IIIB, IIC, IIIC, IID or IIID and the absolute stereochemistry at the carbon atom marked by "*" is R.

18. The compound of claim 17, or a pharmaceutically acceptable salt thereof, wherein:

when the compound is represented by the formula IIB or IIIB, m is 1, 2 or 3 and n is 0;

when the compound is represented by the formula IIC or IIIC, m is 2; and when the compound is represented by the formula IID or IIID, m is 1, 2 or 3 and n is 0 or 1.

19. The compound of claim 2, wherein the compound is represented by the following formula:

(IV)

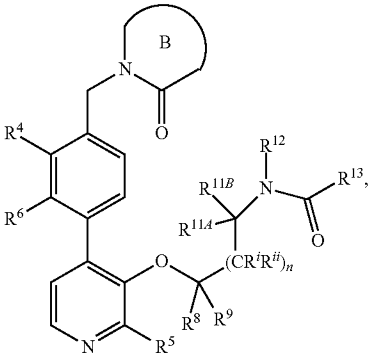

or (V)

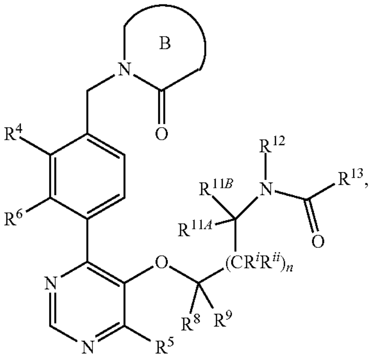

or a pharmaceutically acceptable salt thereof, wherein:

Ring B is represented by one of following formulae:

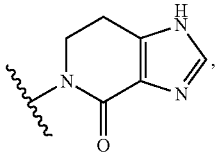 , 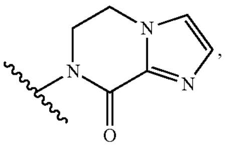 ,

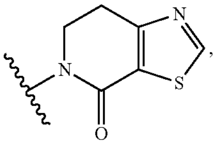 , 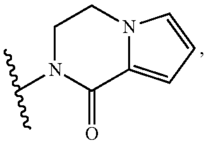 ,

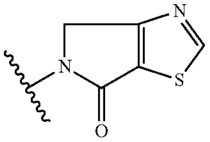 , 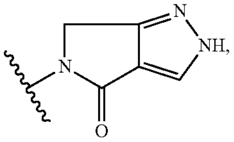

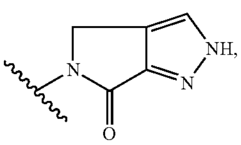 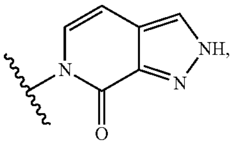

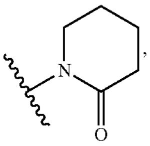 , 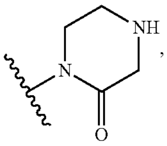 , 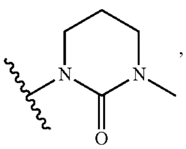 ,

-continued

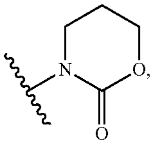
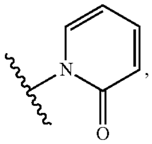
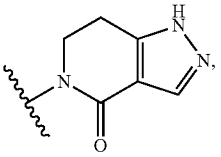
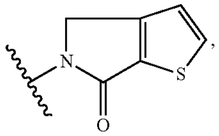
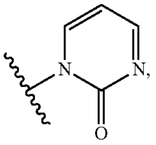
or
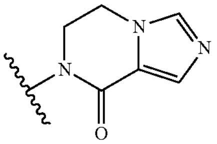

wherein Ring B is optionally substituted with one or two $R^{100}$;

$R^{100}$ is $C_{1-6}$ alkyl or $C_{3-6}$ cycloalkyl;

$R^4$ is selected from H, halogen, —$OR^{4a}$ and $C_{1-6}$ alkyl optionally substituted with one or three halogen;

$R^{4a}$ is $C_{1-4}$ alkyl optionally substituted with one or three halogen;

$R^5$ is H or —$NH_2$;

$R^6$ is H or halogen;

$R^8$, $R^9$, $R^i$, $R^{ii}$, $R^{11A}$ and $R^{11B}$ are each independently H or $C_{1-3}$ alkyl;

$R^{12}$ is $C_{1-3}$ alkyl;

or $R^{12}$ and any one of $R^8$ and $R^9$ together with the atoms to which they are bound forms a 4 to 7-membered azacyclic ring, which ring is optionally substituted with one or more substituents independently selected from halogen, —CN, —OH, $C_{1-6}$ alkyl and $C_{1-6}$ alkoxy;

$R^{13}$ is $C_{2-6}$ alkenyl optionally substituted with $C_{1-6}$ alkyl, $C_{1-6}$ alkoxy or —$NR^{13a}R^{13b}$, and $R^{13a}$ and $R^{13b}$ are each independently H or $C_{1-3}$ alkyl.

20. The compound of claim 19, wherein Ring B is represented by one of the following formulae:

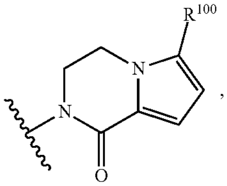
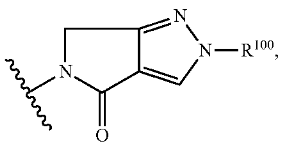
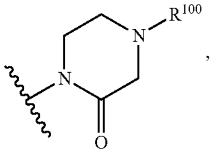
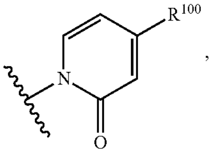
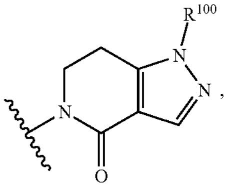
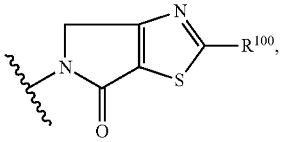
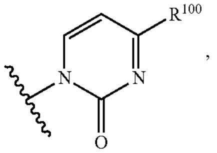
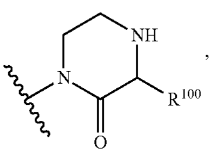
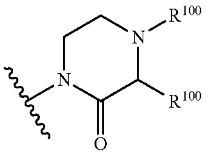
or
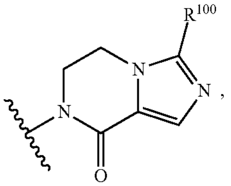

wherein any one of which is optionally substituted with one or two $R^{100}$.

21. A pharmaceutical composition comprising a compound of claim 1 or a pharmaceutically acceptable salt thereof, and a pharmaceutically acceptable excipient.

22. A method of treating a disorder responsive to inhibition of Bruton's tyrosine kinase in a subject comprising administering to the subject an effective amount of the compound according to claim 1, wherein the disorder is pemphiqus vulgaris, rheumatoid arthritis, Sjögren's syndrome, leukemia, or lymphoma.

* * * * *